(12) United States Patent
Corbeil et al.

(10) Patent No.: US 9,358,283 B2
(45) Date of Patent: Jun. 7, 2016

(54) DIATOM-BASED VACCINES

(71) Applicants: The Regents of the University of California, Oakland, CA (US); Synaptic Research, LLC, Baltimore, MD (US)

(72) Inventors: Lynette B. Corbeil, San Diego, CA (US); Mark Hildebrand, La Jolla, CA (US); Roshan Shrestha, San Diego, CA (US); Aubrey Davis, Lakeside, CA (US); Rachel Schrier, Del Mar, CA (US); George A. Oyler, Lincoln, NE (US); Julian N. Rosenberg, Naugatuck, CT (US)

(73) Assignees: The Regents of the University of California, Oakland, CA (US); Synaptic Research, LLC, Baltimore, MD (US)

( * ) Notice: Subject to any disclaimer, the term of this patent is extended or adjusted under 35 U.S.C. 154(b) by 59 days.

(21) Appl. No.: 14/353,721

(22) PCT Filed: Oct. 26, 2012

(86) PCT No.: PCT/US2012/062112
§ 371 (c)(1),
(2) Date: Apr. 23, 2014

(87) PCT Pub. No.: WO2013/063388
PCT Pub. Date: May 2, 2013

(65) Prior Publication Data
US 2015/0037370 A1 Feb. 5, 2015

Related U.S. Application Data

(60) Provisional application No. 61/553,139, filed on Oct. 28, 2011.

(51) Int. Cl.
| | | |
|---|---|---|
| *A61K 39/00* | (2006.01) | |
| *A61K 39/38* | (2006.01) | |
| *A61K 39/395* | (2006.01) | |
| *A61K 39/295* | (2006.01) | |
| *C12N 1/12* | (2006.01) | |
| *C12N 15/79* | (2006.01) | |
| *A61K 39/02* | (2006.01) | |
| *A61K 36/06* | (2006.01) | |
| *A61K 39/102* | (2006.01) | |
| *C12N 7/00* | (2006.01) | |

(52) U.S. Cl.
CPC ............ *A61K 39/295* (2013.01); *A61K 36/06* (2013.01); *A61K 39/00* (2013.01); *A61K 39/102* (2013.01); *A61K 39/107* (2013.01); *C12N 1/12* (2013.01); *C12N 7/00* (2013.01); *C12N 15/79* (2013.01); *A61K 2039/51* (2013.01); *A61K 2039/517* (2013.01); *A61K 2039/523* (2013.01); *A61K 2039/541* (2013.01); *A61K 2039/542* (2013.01); *A61K 2039/57* (2013.01); *C12N 2760/18534* (2013.01)

(58) Field of Classification Search
CPC ..... A61K 39/395; A61K 36/00; A61K 36/02; A61K 39/00
USPC ..................... 424/130.1, 134.1, 184.1, 185.1; 435/257.1; 536/23.1, 23.7
See application file for complete search history.

(56) References Cited

U.S. PATENT DOCUMENTS

2009/0098149 A1 4/2009 Sayre et al.

FOREIGN PATENT DOCUMENTS

| EP | 0532090 A2 | 3/1993 |
|---|---|---|
| EP | 1645633 A2 | 4/2006 |
| EP | 2006/078880 A2 | 7/2006 |
| KR | 10-2012-0101572 | 9/2012 |
| WO | 2011/090708 | 9/2011 |

OTHER PUBLICATIONS

WO patent application No. PCT/US2012/062112, International Search Report mailed Feb. 1, 2013.
WO patent application No. PCT/US2012/062112, Written Opinion mailed Feb. 1, 2013.
WO patent application No. PCT/US2012/062112, International Preliminary Report on Patentability mailed May 8, 2014.
Berzofsky, Jay A., "A push-pull vaccine strategy using Toll-like receptor ligands, IL-15, and blockage of negative regulation to improve the quality and quantity of T cell immune responses," Vaccine, Jun. 19, 2012; 30(29): 4323-4327, published online Nov. 21, 2011.
Fujita, Y. et al., "Overview and outlook of Toll-like receptor ligand-antigen conjugate vaccines," Ther Deliv. Jun. 2012;3(6):749-60, abstract.
Hempel, Franziska et al., "Algae as protein factories: expression of a human antibody and respective antigen in the diatom *Phaeodactylum tricornutum*," PLoS One, Dec. 2011, vol. 6, Issue 12, pp. 1-7.
Kundu, J. et al., "Intranasal immunization with recombinant toxin-coregulated pilus and cholera toxin B subunit protects rabbits against Vibrio cholera O1 challenge," FEMS Immunol Med Microbiol. Jul. 2009;56(2):179-84, first published online Jul. 1, 2009.
Lahiri, A. et al., "Engagement of TLR signaling as adjuvant: towards smarter vaccine and beyond," Vaccine Dec. 9, 2008:26(52):6777-83, Epub Oct. 7, 2008, abstract.
Ma, X. et al., "The effects of GM-CSF and IL-5 as molecular adjuvants on immune responses and contraception induced by mZP3 DNA vaccination," Am J Reprod Immunol. Dec. 2012;68(6):476-85. Epub Aug. 31, 2012, abstract.
Muse, M. et al., "A one dose experimental cholera vaccine," FEMS Immunol Med Microbiol. Oct. 2012 ;66(1):98-115, first published online Oct. 1, 2012.
Price, Gregory A. et al., "Evaluation of TcpF-A2-CTB chimera and evidence of additive protective efficacy of immunizing with TcpF and CTB in the suckling mouse model of cholera," PLoS One 7(8): e42434, Aug. 7, 2012.
Thompson, Afton L. et al., "Cytokines: the future of intranasal vaccine adjuvants," Hindawi Publishing Corporation, Clinical and Developmental Immunology, vol. 2011, Article ID 289597, May 22, 2011, 17 pages.

*Primary Examiner* — Rodney P Swartz
(74) *Attorney, Agent, or Firm* — Weaver Austin Villeneuve & Sampson LLP

(57) ABSTRACT

This invention provides diatom-based vaccines.

33 Claims, 19 Drawing Sheets

AGCTTGCGCTTTTTCCGAGAACTCCCCATAAGTCAACGGCTCCAATCAAGAATGTATCCGA
CAACGGCGAGCATAGCAACACGTCCGTCTTTGGAGTAGAATCATCATGTTGTGGATGAATA
CACAGATGAATGACATTAAAAGCATGAACATGTTAGAGAGTAGGAGGTAGAGATTGATATG
GTAGCATTGCGATGTTTGTTTTGGTCAGCATATGATGAGTGGATACCAATATGATGAAAG
TTGAATCTCGCGTTTGAGCTCAGCGGTACGTTATTGATCGAAAGTAGCCTGATCAAAATCC
TTGGAGAGTACAAGAGGATCAAAGAATCCAGTGGGGCGATAACTCCAAGCTCGTTCTCAA
AGAGGCAATGGAGGTAGAAACTCATCCCAGTTGAGAAGAAGTGAAGGCAGTGGCGGTGGCG
AAAGCAGAGGCAACGAGGACAGACTTCCTGTGGGTTGATGCAACGAATATTTCCAGAAGGA
GAAGTTTAGAGAGTTGAACCGCTACCTACAATGACAAAGTATCGTATCGATTTTGATGTTG
GTTGGTTATGAATTCAAACTGTAAGTTGGATTGTGAGAAGATCAGAAGTTGAACGAACACA
TCTTTCCGATCATTCACCTCCACACTGCAACAACACGGTACTTCTTCCGCGGCAGGTCTCT
GTCGCCATTCTCTTGTCCTGTTGTTGGCTGTGAGACGAGGAAAGCAACGACAAGTTTCACA
AAAGGGAGTTCCTTTAACGAGATATGTTTTTATAAAGAGTCCCAATAGAAAGACAAATTG
ATTCCTCCGTGCAAACGCGCAAATAAACACCACGTCCATTATATCCATATCTTTCAGAGTA
TCCAACAAGTGTTGAAGGACAGGTAGTTGAAGTAACGTATCTTCCCCCTCGACTGGATCCA
TCAACAAGGCGAACAAATCCATTCAACCTCTCATAAATTATCTGATTTACCAAACCGATAT
CAACAAGTTTGTACAAAAAAGCTGAACGAGAAACGTAAAATGATATAAATATCAATATATT
AAATTAGATTTTGCATAAAAAACAGACTACATAATACTGTAAAACACAACATATCCAGTCA
CTATGGCGGCCGCATTAGGCACCCCAGGCTTTACACTTTATGCTTCCGGCTCGTATAATGT
GTGGATTTTGAGTTAGGATCCGTCGAGATTTTCAGGAGCTAAGGAAGCTAAAATGGAGAAA
AAAATCACTGGATATACCACCGTTGATATATCCCAATGGCATCGTAAAGAACATTTTGAGG
CATTTCAGTCAGTTGCTCAATGTACCTATAACCAGACCGTTCAGCTGGATATTACGGCCTT
TTTAAAGACCGTAAAGAAAATAAGCACAAGTTTTATCCGGCCTTTATTCACATTCTTGCC
CGCCTGATGAATGCTCATCCGGAATTCCGTATGGCAATGAAAGACGGTGAGCTGGTGATAT
GGGATAGTGTTCACCCTTGTTACACCGTTTTCCATGAGCAAACTGAAACGTTTTCATCGCT
CTGGAGTGAATACCACGACGATTTCCGGCAGTTTCTACACATATATTCGCAAGATGTGGCG
TGTTACGGTGAAAACCTGGCCTATTTCCCTAAAGGGTTTATTGAGAATATGTTTTTCGTCT
CAGCCAATCCCTGGGTGAGTTTCACCAGTTTTGATTTAAACGTGGCCAATATGGACAACTT
CTTCGCCCCCGTTTTCACCATGGGCAAATATTATACGCAAGGCGACAAGGTGCTGATGCCG

*Fig. 8A*

CTGGCGATTCAGGTTCATCATGCCGTTTGTGATGGCTTCCATGTCGGCAGAATGCTTAATG
AATTACAACAGTACTGCGATGAGTGGCAGGGCGGGGCGTAAAGATCTGGATCCGGCTTACT
AAAAGCCAGATAACAGTATGCGTATTTGCGCGCTGATTTTTGCGGTATAAGAATATATACT
GATATGTATACCCGAAGTATGTCAAAAAGAGGTATGCTATGAAGCAGCGTATTACAGTGAC
AGTTGACAGCGACAGCTATCAGTTGCTCAAGGCATATATGATGTCAATATCTCCGGTCTGG
TAAGCACAACCATGCAGAATGAAGCCCGTCGTCTGCGTGCCGAACGCTGGAAAGCGGAAAA
TCAGGAAGGGATGGCTGAGGTCGCCCGGTTTATTGAAATGAACGGCTCTTTTGCTGACGAG
AACAGGGGCTGGTGAAATGCAGTTTAAGGTTTACACCTATAAAAGAGAGAGCCGTTATCGT
CTGTTTGTGGATGTACAGAGTGATATTATTGACACGCCCGGGCGACGGATGGTGATCCCCC
TGGCCAGTGCACGTCTGCTGTCAGATAAAGTCTCCCGTGAACTTTACCCGGTGGTGCATAT
CGGGGATGAAAGCTGGCGCATGATGACCACCGATATGGCCAGTGTGCCGGTCTCCGTTATC
GGGGAAGAAGTGGCTGATCTCAGCCACCGCGAAAATGACATCAAAAACGCCATTAACCTGA
TGTTCTGGGGAATATAAATGTCAGGCTCCCTTATACACAGCCAGTCTGCAGGTCGACCATA
GTGACTGGATATGTTGTGTTTTACAGTATTATGTAGTCTGTTTTTTATGCAAAATCTAATT
TAATATATTGATATTTATATCATTTTACGTTTCTCGTTCAGCTTTCTTGTACAAAGTGGTT
GATATCGCATGCGGTACCGGCGGA*ATGGTGAGCAAGGGCGAGGAGCTGTTCACCGGGGTGG*
*TGCCCATCCTGGTCGAGCTGGACGGCGACGTAAACGGCCACAAGTTCAGCGTGTCCGGCGA*
*GGGCGAGGGCGATGCCACCTACGGCAAGCTGACCCTGAAGTTCATCTGCACCACCGGCAAG*
*CTGCCCGTGCCCTGGCCCACCCTCGTGACCACCCTGACCTACGGCGTGCAGTGCTTCAGCC*
*GCTACCCCGACCACATGAAGCAGCACGACTTCTTCAAGTCCGCCATGCCCGAAGGCTACGT*
*CCAGGAGCGCACCATCTTCTTCAAGGACGACGGCAACTACAAGACCCGCGCCGAGGTGAAG*
*TTCGAGGGCGACACCCTGGTGAACCGCATCGAGCTGAAGGGCATCGACTTCAAGGAGGACG*
*GCAACATCCTGGGGCACAAGCTGGAGTACAACTACAACAGCCACAACGTCTATATCATGGC*
*CGACAAGCAGAAGAACGGCATCAAGGTGAACTTCAAGATCCGCCACAACATCGAGGACGGC*
*AGCGTGCAGCTCGCCGACCACTACCAGCAGAACACCCCCATCGGCGACGGCCCCGTGCTGC*
*TGCCCGACAACCACTACCTGAGCACCCAGTCCGCCCTGAGCAAAGACCCCAACGAGAAGCG*
*CGATCACATGGTCCTGCTGGAGTTCGTGACCGCCGCCGGGATCACTCTCGGCATGGACGAG*
*CTGTACAAG*TAAGCGGCCGCATACTGGATTGGTGAATCAATGAGCCGTAGCACAATGGTTA

*Fig. 8B*

```
CATTCGGCTAGCTAAGATCCAATGGCAAGGACCAAGTGCTGGAACTTGTTTTGCTTTAGCA
GATCTTAGCGTGAGAGGTATTTGTCCTCTGTCAGGAGTAGATAGTAGATGTTCTTTTTAAA
CTAAAATGCTAACTGTTCCGAATTCCTCATCGCAGCTAATCCGTACATCAAAAGACAAAAT
GCTAGGTATGTGTACTACATCTCCTGTTGCTAGATAAGACATATGATAGGAAACACACCAT
CAATAGTCATTGTAGCTTTACTTATACTACGCATTTGCACTTTCCCCTGAGTGGCAGAGGC
GCATTGAGAAAATCGATCTCAACATAGTTTATGTAGCATCCCCTAGATCCATTACTTTAAG
TCTCCTTCGTCTTTGGTGTAGGCATGTTGGACACAACGAGGTAAAACACAACACAAACAAT
GTGTCCAGCAAAGTAGTAGCTGCTCCAGTTCTCCCGGGGGATCCACTAGTTCTAGAGCGGC
CGGCCGCCACCGCGGTGGAGCTCCAGCTTTTGTTCCCTTTAGTGAGGGTTAATTGCGCGCT
TGGCGTAATCATGGTCATAGCTGTTTCCTGTGTGAAATTGTTATCCGCTCACAATTCCACA
CAACATACGAGCCGGAAGCATAAAGTGTAAAGCCTGGGGTGCCTAATGAGTGAGCTAACTC
ACATTAATTGCGTTGCGCTCACTGCCCGCTTTCCAGTCGGGAAACCTGTCGTGCCAGCTGC
ATTAATGAATCGGCCAACGCGCGGGGAGAGGCGGTTTGCGTATTGGGCGCTCTTCCGCTTC
CTCGCTCACTGACTCGCTGCGCTCGGTCGTTCGGCTGCGGCGAGCGGTATCAGCTCACTCA
AAGGCGGTAATACGGTTATCCACAGAATCAGGGGATAACGCAGGAAAGAACATGTGAGCAA
AAGGCCAGCAAAAGGCCAGGAACCGTAAAAAGGCCGCGTTGCTGGCGTTTTTCCATAGGCT
CCGCCCCCTGACGAGCATCACAAAAATCGACGCTCAAGTCAGAGGTGGCGAAACCCGACA
GGACTATAAAGATACCAGGCGTTTCCCCCTGGAAGCTCCCTCGTGCGCTCTCCTGTTCCGA
CCCTGCCGCTTACCGGATACCTGTCCGCCTTTCTCCCTTCGGGAAGCGTGGCGCTTTCTCA
TAGCTCACGCTGTAGGTATCTCAGTTCGGTGTAGGTCGTTCGCTCCAAGCTGGGCTGTGTG
CACGAACCCCCCGTTCAGCCCGACCGCTGCGCCTTATCCGGTAACTATCGTCTTGAGTCCA
ACCCGGTAAGACACGACTTATCGCCACTGGCAGCAGCCACTGGTAACAGGATTAGCAGAGC
GAGGTATGTAGGCGGTGCTACAGAGTTCTTGAAGTGGTGGCCTAACTACGGCTACACTAGA
AGGACAGTATTTGGTATCTGCGCTCTGCTGAAGCCAGTTACCTTCGGAAAAAGAGTTGGTA
GCTCTTGATCCGGCAAACAAACCACCGCTGGTAGCGGTGGTTTTTTTGTTTGCAAGCAGCA
GATTACGCGCAGAAAAAAGGATCTCAAGAAGATCCTTTGATCTTTTCTACGGGGTCTGAC
GCTCAGTGGAACGAAAACTCACGTTAAGGGATTTTGGTCATGAGATTATCAAAAGGATCT
TCACCTAGATCCTTTTAAATTAAAAATGAAGTTTTAAATCAATCTAAAGTATATATGAGTA
AACTTGGTCTGACAGTTACCAATGCTTAATCAGTGAGGCACCTATCTCAGCGATCTGTCTA
```

*Fig. 8C*

TTTCGTTCATCCATAGTTGCCTGACTCCCCGTCGTGTAGATAACTACGATACGGGAGGGCT
TACCATCTGGCCCCAGTGCTGCAATGATACCGCGAGACCCACGCTCACCGGCTCCAGATTT
ATCAGCAATAAACCAGCCAGCCGGAAGGGCCGAGCGCAGAAGTGGTCCTGCAACTTTATCC
GCCTCCATCCAGTCTATTAATTGTTGCCGGGAAGCTAGAGTAAGTAGTTCGCCAGTTAATA
GTTTGCGCAACGTTGTTGCCATTGCTACAGGCATCGTGGTGTCACGCTCGTCGTTTGGTAT
GGCTTCATTCAGCTCCGGTTCCCAACGATCAAGGCGAGTTACATGATCCCCATGTTGTGC
AAAAAAGCGGTTAGCTCCTTCGGTCCTCCGATCGTTGTCAGAAGTAAGTTGGCCGCAGTGT
TATCACTCATGGTTATGGCAGCACTGCATAATTCTCTTACTGTCATGCCATCCGTAAGATG
CTTTTCTGTGACTGGTGAGTACTCAACCAAGTCATTCTGAGAATAGTGTATGCGGCGACCG
AGTTGCTCTTGCCCGGCGTCAATACGGGATAATACCGCGCCACATAGCAGAACTTTAAAAG
TGCTCATCATTGGAAAACGTTCTTCGGGGCGAAAACTCTCAAGGATCTTACCGCTGTTGAG
ATCCAGTTCGATGTAACCCACTCGTGCACCCAACTGATCTTCAGCATCTTTTACTTTCACC
AGCGTTTCTGGGTGAGCAAAAACAGGAAGGCAAAATGCCGCAAAAAAGGGAATAAGGGCGA
CACGGAAATGTTGAATACTCATACTCTTCCTTTTTCAATATTATTGAAGCATTTATCAGGG
TTATTGTCTCATGAGCGGATACATATTTGAATGTATTTAGAAAAATAAACAAATAGGGGTT
CCGCGCACATTTCCCCGAAAAGTGCCACCTAAATTGTAAGCGTTAATATTTTGTTAAAATT
CGCGTTAAATTTTTGTTAAATCAGCTCATTTTTTAACCAATAGGCCGAAATCGGCAAAATC
CCTTATAAATCAAAAGAATAGACCGAGATAGGGTTGAGTGTTGTTCCAGTTTGGAACAAGA
GTCCACTATTAAAGAACGTGGACTCCAACGTCAAAGGGCGAAAAACCGTCTATCAGGGCGA
TGGCCCACTACGTGAACCATCACCCTAATCAAGTTTTTTGGGGTCGAGGTGCCGTAAAGCA
CTAAATCGGAACCCTAAAGGGAGCCCCCGATTTAGAGCTTGACGGGGAAAGCCGGCGAACG
TGGCGAGAAAGGAAGGGAAGAAAGCGAAAGGAGCGGGCGCTAGGGCGCTGGCAAGTGTAGC
GGTCACGCTGCGCGTAACCACCACACCCGCCGCGCTTAATGCGCCGCTACAGGGCGCGTCC
CATTCGCCATTCAGGCTGCGCAACTGTTGGGAAGGGCGATCGGTGCGGGCCTCTTCGCTAT
TACGCCAGCTGGCGAAAGGGGGATGTGCTGCAAGGCGATTAAGTTGGGTAACGCCAGGGTT
TTCCCAGTCACGACGTTGTAAAACGACGGCCAGTGAGCGCGCGTAATACGACTCACTATAG
GGCGAATTGGGTACGTACCGGGCCCCCCTCGAGGTCGACGGTATCGATA
(SEQ ID NO:8)

<u>Underlined = FCP promoter and terminator</u>
Bold = Gateway B fragment
*Italic = eGFP*

*Fig. 8D*

AGCTTGCGCTTTTTCCGAGAACTCCCCATAAGTCAACGGCTCCAATCAAGAATGTATCCGA
CAACGGCGAGCATAGCAACACGTCCGTCTTTGGAGTAGAATCATCATGTTGTGGATGAATA
CACAGATGAATGACATTAAAAGCATGAACATGTTAGAGAGTAGGAGGTAGAGATTGATATG
GTAGCATTGCGATGTTTGTTTTTGGTCAGCATATGATGAGTGGATACCAATATGATGAAAG
TTGAATCTCGCGTTTGAGCTCAGCGGTACGTTATTGATCGAAAGTAGCCTGATCAAAATCC
TTGGAGAGTACAAGAGGATCAAAGAATCCAGTGGGGGCGATAACTCCAAGCTCGTTCTCAA
AGAGGCAATGGAGGTAGAAACTCATCCCAGTTGAGAAGAAGTGAAGGCAGTGGCGGTGGCG
AAAGCAGAGGCAACGAGGACAGACTTCCTGTGGGTTGATGCAACGAATATTCCAGAAGGA
GAAGTTTAGAGAGTTGAACCGCTACCTACAATGACAAAGTATCGTATCGATTTTGATGTTG
GTTGGTTATGAATTCAAACTGTAAGTTGGATTGTGAGAAGATCAGAAGTTGAACGAACACA
TCTTTCCGATCATTCACCTCCACACTGCAACAACACGGTACTTCTTCCGCGGCAGGTCTCT
GTCGCCATTCTCTTGTCCTGTTGTTGGCTGTGAGACGAGGAAAGCAACGACAAGTTTCACA
AAAGGGAGTTCCTTTAACGAGATATGTTTTTTATAAAGAGTCCCAATAGAAAGACAAATTG
ATTCCTCCGTGCAAACGCGCAAATAAACACCACGTCCATTATATCCATATCTTTCAGAGTA
TCCAACAAGTGTTGAAGGACAGGTAGTTGAAGTAACGTATCTTCCCCCTCGACTGGATCCA
TCAACAAGGCGAACAAATCCATTCAACCTCTCATAAATTATCTGATTTACCAAACCGATAT
CAACAAGTTTGTACAAAAAAGCATGTCTGTAAATGAAGTTGCACCGTTGTCATCTGTACCA
GCAGAACTAAAAGATGCTGCTGGAGGAAATAAAAAAGCGGCAGAGAAATCAGAGGGTGCTA
CGGGTGTAGAAAAGAAAAAACCACACTTTTCCAACGAGTGAAACAATTTTTCACCGGAAG
TAAGAGCGGTGCGAAACCTGTAGCGGGAGATGAGACAGCGAATAAAGTCAATTATCAAGAT
TTGGAAGATAATTTGAACTTAAAAGGATTAATTTCTTTAGAAGATGATCGAAATGCTAATT
TTGAAAGTAATGTATTGAAAAATGAGAAATTTTTAGATGAAGCAAGAGAGATTTCGAAGAA
ATCAATTCCTGAAGCGACAGTTAAGCAAATGTCTCATTTACCTGAATTTGATGATATTCTC
ACCGAGGGAGCTAAGAAAGTAGAAAGTCGTATTAATAAGGCAATCACATTCCGCCCTTCTG
TTGAGGAGTTTTCAGAAATTCAAGATTTGGTGAAAACGTTACCGAAAACAAAGGTTATAGA
GGATCTTTCAACAAAAACAAATGAAATCACAGAAGCTTTAGCTGCGACATCGAAAACCATT
CAACGTACACCGGAGTTGAAAGAACAGTTGAAGACAGCAATAGAGGATTTCTTACAAAACA
GTCAAGGCAAACCTTTGACAGTGCAGATGATCGAGAATCTTAATCACGGATTACGTCCGGA

*Fig. 9A*

TGAGGGAGAAGGTCGTTTACTTTATAAAAAGAGAATTTAACCAAAGAAAATGCGGTATTT
TCTAGTCCCGAAGCGGCAAAAATTCAATTAGCGGAACGGTTGATTTTATCAATCGAGCGA
AAAATGAAGGGATTGAGCCGAGTGTGGTTGGGGCATTAGTTTATCAGCGATTGATTGCTTA
TCACCCATTTGCAGAAGGTAATGGACGTATGGCGAGAGTCATAGTAAATAAAATTTTACTT
GATGCAGGTTATCCGGCATTTACCAAATTTAGTGATGAGTTTGAACCGCAGATTATTCCTC
AAACGAAAGCATCAACTAAATCCGCAACGAGCAGTGAAGTGGTAGTTGAGTTTTTAAAAGA
GTTGGCAAAAAAGGAAGCAAGGAAGATAACGAGCAGAATTTAGAAAAAACTGACCGCACT
TCTACGGACTTGACAGAAAGTGCGGTAGAAAATTCGGCTGCTTTGAGTTTACCCAGCTTTC
TTGTACAAAGTGGTTGATATCGCATGCGGTACCGGCGGA_ATGGTGAGCAAGGGCGAGGAGC_
_TGTTCACCGGGGTGGTGCCCATCCTGGTCGAGCTGGACGGCGACGTAAACGGCCACAAGTT_
_CAGCGTGTCCGGCGAGGGCGAGGGCGATGCCACCTACGGCAAGCTGACCCTGAAGTTCATC_
_TGCACCACCGGCAAGCTGCCCGTGCCCTGGCCCACCCTCGTGACCACCCTGACCTACGGCG_
_TGCAGTGCTTCAGCCGCTACCCCGACCACATGAAGCAGCACGACTTCTTCAAGTCCGCCAT_
_GCCCGAAGGCTACGTCCAGGAGCGCACCATCTTCTTCAAGGACGACGGCAACTACAAGACC_
_CGCGCCGAGGTGAAGTTCGAGGGCGACACCCTGGTGAACCGCATCGAGCTGAAGGGCATCG_
_ACTTCAAGGAGGACGGCAACATCCTGGGGCACAAGCTGGAGTACAACTACAACAGCCACAA_
_CGTCTATATCATGGCCGACAAGCAGAAGAACGGCATCAAGGTGAACTTCAAGATCCGCCAC_
_AACATCGAGGACGGCAGCGTGCAGCTCGCCGACCACTACCAGCAGAACACCCCCATCGGCG_
_ACGGCCCCGTGCTGCTGCCCGACAACCACTACCTGAGCACCCAGTCCGCCCTGAGCAAAGA_
_CCCCAACGAGAAGCGCGATCACATGGTCCTGCTGGAGTTCGTGACCGCCGCCGGGATCACT_
_CTCGGCATGGACGAGCTGTACAAGTAAGCGGCCGCATACTGGATTGGTGAATCAATGAGCC_
GTAGCACAATGGTTACATTCGGCTAGCTAAGATCCAATGGCAAGGACCAAGTGCTGGAACT
TGTTTTGCTTTAGCAGATCTTAGCGTGAGAGGTATTTGTCCTCTGTCAGGAGTAGATAGTA
GATGTTCTTTTTAAACTAAATGCTAACTGTTCCGAATTCCTCATCGCAGCTAATCCGTAC
ATCAAAAGACAAAATGCTAGGTATGTGTACTACATCTCCTGTTGCTAGATAAGACATATGA
TAGGAAACACACCATCAATAGTCATTGTAGCTTTACTTATACTACGCATTTGCACTTTCCC
CTGAGTGGCAGAGGCGCATTGAGAAAATCGATCTCAACATAGTTTATGTAGCATCCCTAG
ATCCATTACTTTAAGTCTCCTTCGTCTTTGGTGTAGGCATGTTGGACACAACGAGGTAAAA
CACAACACAAACAATGTGTCCAGCAAAGTAGTAGCTGCTCCAGTTCTCCCGGGGGATCCAC

*Fig. 9B*

```
TAGTTCTAGAGCGGCCGGCCGCCACCGCGGTGGAGCTCCAGCTTTTGTTCCCTTTAGTGAG
GGTTAATTGCGCGCTTGGCGTAATCATGGTCATAGCTGTTTCCTGTGTGAAATTGTTATCC
GCTCACAATTCCACACAACATACGAGCCGGAAGCATAAAGTGTAAAGCCTGGGGTGCCTAA
TGAGTGAGCTAACTCACATTAATTGCGTTGCGCTCACTGCCCGCTTTCCAGTCGGGAAACC
TGTCGTGCCAGCTGCATTAATGAATCGGCCAACGCGCGGGGAGAGGCGGTTTGCGTATTGG
GCGCTCTTCCGCTTCCTCGCTCACTGACTCGCTGCGCTCGGTCGTTCGGCTGCGGCGAGCG
GTATCAGCTCACTCAAAGGCGGTAATACGGTTATCCACAGAATCAGGGGATAACGCAGGAA
AGAACATGTGAGCAAAAGGCCAGCAAAAGGCCAGGAACCGTAAAAAGGCCGCGTTGCTGGC
GTTTTTCCATAGGCTCCGCCCCCTGACGAGCATCACAAAAATCGACGCTCAAGTCAGAGG
TGGCGAAACCCGACAGGACTATAAAGATACCAGGCGTTTCCCCCTGGAAGCTCCCTCGTGC
GCTCTCCTGTTCCGACCCTGCCGCTTACCGGATACCTGTCCGCCTTTCTCCCTTCGGGAAG
CGTGGCGCTTTCTCATAGCTCACGCTGTAGGTATCTCAGTTCGGTGTAGGTCGTTCGCTCC
AAGCTGGGCTGTGTGCACGAACCCCCCGTTCAGCCCGACCGCTGCGCCTTATCCGGTAACT
ATCGTCTTGAGTCCAACCCGGTAAGACACGACTTATCGCCACTGGCAGCAGCCACTGGTAA
CAGGATTAGCAGAGCGAGGTATGTAGGCGGTGCTACAGAGTTCTTGAAGTGGTGGCCTAAC
TACGGCTACACTAGAAGGACAGTATTTGGTATCTGCGCTCTGCTGAAGCCAGTTACCTTCG
GAAAAAGAGTTGGTAGCTCTTGATCCGGCAAACAAACCACCGCTGGTAGCGGTGGTTTTTT
TGTTTGCAAGCAGCAGATTACGCGCAGAAAAAAAGGATCTCAAGAAGATCCTTTGATCTTT
TCTACGGGGTCTGACGCTCAGTGGAACGAAAACTCACGTTAAGGGATTTTGGTCATGAGAT
TATCAAAAAGGATCTTCACCTAGATCCTTTTAAATTAAAAATGAAGTTTTAAATCAATCTA
AAGTATATATGAGTAAACTTGGTCTGACAGTTACCAATGCTTAATCAGTGAGGCACCTATC
TCAGCGATCTGTCTATTTCGTTCATCCATAGTTGCCTGACTCCCCGTCGTGTAGATAACTA
CGATACGGGAGGGCTTACCATCTGGCCCCAGTGCTGCAATGATACCGCGAGACCCACGCTC
ACCGGCTCCAGATTTATCAGCAATAAACCAGCCAGCCGGAAGGGCCGAGCGCAGAAGTGGT
CCTGCAACTTTATCCGCCTCCATCCAGTCTATTAATTGTTGCCGGGAAGCTAGAGTAAGTA
GTTCGCCAGTTAATAGTTTGCGCAACGTTGTTGCCATTGCTACAGGCATCGTGGTGTCACG
CTCGTCGTTTGGTATGGCTTCATTCAGCTCCGGTTCCCAACGATCAAGGCGAGTTACATGA
TCCCCCATGTTGTGCAAAAAGCGGTTAGCTCCTTCGGTCCTCCGATCGTTGTCAGAAGTA
AGTTGGCCGCAGTGTTATCACTCATGGTTATGGCAGCACTGCATAATTCTCTTACTGTCAT
```

*Fig. 9C*

GCCATCCGTAAGATGCTTTTCTGTGACTGGTGAGTACTCAACCAAGTCATTCTGAGAATAG
TGTATGCGGCGACCGAGTTGCTCTTGCCCGGCGTCAATACGGGATAATACCGCGCCACATA
GCAGAACTTTAAAAGTGCTCATCATTGGAAAACGTTCTTCGGGGCGAAAACTCTCAAGGAT
CTTACCGCTGTTGAGATCCAGTTCGATGTAACCCACTCGTGCACCCAACTGATCTTCAGCA
TCTTTTACTTTCACCAGCGTTTCTGGGTGAGCAAAAACAGGAAGGCAAAATGCCGCAAAAA
AGGGAATAAGGGCGACACGGAAATGTTGAATACTCATACTCTTCCTTTTTCAATATTATTG
AAGCATTTATCAGGGTTATTGTCTCATGAGCGGATACATATTTGAATGTATTTAGAAAAAT
AAACAAATAGGGGTTCCGCGCACATTTCCCCGAAAAGTGCCACCTAAATTGTAAGCGTTAA
TATTTTGTTAAAATTCGCGTTAAATTTTGTTAAATCAGCTCATTTTTTAACCAATAGGCC
GAAATCGGCAAAATCCCTTATAAATCAAAAGAATAGACCGAGATAGGGTTGAGTGTTGTTC
CAGTTTGGAACAAGAGTCCACTATTAAAGAACGTGGACTCCAACGTCAAAGGGCGAAAAAC
CGTCTATCAGGGCGATGGCCCACTACGTGAACCATCACCCTAATCAAGTTTTTTGGGGTCG
AGGTGCCGTAAAGCACTAAATCGGAACCCTAAAGGGAGCCCCCGATTTAGAGCTTGACGGG
GAAAGCCGGCGAACGTGGCGAGAAAGGAAGGGAAGAAAGCGAAAGGAGCGGGCGCTAGGGC
GCTGGCAAGTGTAGCGGTCACGCTGCGCGTAACCACCACACCCGCCGCGCTTAATGCGCCG
CTACAGGGCGCGTCCCATTCGCCATTCAGGCTGCGCAACTGTTGGGAAGGGCGATCGGTGC
GGGCCTCTTCGCTATTACGCCAGCTGGCGAAAGGGGGATGTGCTGCAAGGCGATTAAGTTG
GGTAACGCCAGGGTTTTCCCAGTCACGACGTTGTAAAACGACGGCCAGTGAGCGCGCGTAA
TACGACTCACTATAGGGCGAATTGGGTACGTACCGGGCCCCCCCTCGAGGTCGACGGTATC
GATA (SEQ ID NO:9)

Underlined = FCP promoter and terminator
Bold = Gateway B fragment
Double Underlined = DR2 domain with start codon added
*Italic = eGFP*

*Fig. 9D*

AGCTTGCGCTTTTTCCGAGAACTCCCCATAAGTCAACGGCTCCAATCAAGAATGTATCCGA
CAACGGCGAGCATAGCAACACGTCCGTCTTTGGAGTAGAATCATCATGTTGTGGATGAATA
CACAGATGAATGACATTAAAAGCATGAACATGTTAGAGAGTAGGAGGTAGAGATTGATATG
GTAGCATTGCGATGTTTGTTTTTGGTCAGCATATGATGAGTGGATACCAATATGATGAAAG
TTGAATCTCGCGTTTGAGCTCAGCGGTACGTTATTGATCGAAAGTAGCCTGATCAAAATCC
TTGGAGAGTACAAGAGGATCAAAGAATCCAGTGGGGCGATAACTCCAAGCTCGTTCTCAA
AGAGGCAATGGAGGTAGAAACTCATCCCAGTTGAGAAGAAGTGAAGGCAGTGGCGGTGGCG
AAAGCAGAGGCAACGAGGACAGACTTCCTGTGGGTTGATGCAACGAATATTTCCAGAAGGA
GAAGTTTAGAGAGTTGAACCGCTACCTACAATGACAAAGTATCGTATCGATTTTGATGTTG
GTTGGTTATGAATTCAAACTGTAAGTTGGATTGTGAGAAGATCAGAAGTTGAACGAACACA
TCTTTCCGATCATTCACCTCCACACTGCAACAACACGGTACTTCTTCCGCGGCAGGTCTCT
GTCGCCATTCTCTTGTCCTGTTGTTGGCTGTGAGACGAGGAAAGCAACGACAAGTTTCACA
AAAGGGAGTTCCTTTAACGAGATATGTTTTTTATAAAGAGTCCCAATAGAAAGACAAATTG
ATTCCTCCGTGCAAACGCGCAAATAAACACCACGTCCATTATATCCATATCTTTCAGAGTA
TCCAACAAGTGTTGAAGGACAGGTAGTTGAAGTAACGTATCTTCCCCCTCGACTGGATCCA
TCAACAAGGCGAACAAATCCATTCAACCTCTCATAAATTATCTGATTTACCAAACCGATA**T
CAACAAGTTTGTACAAAAAAGC**ATGTCTGTGAACGAGGTGGCTCCACTCTCTTCTGTGCCA
GCTGAGCTCAAGGATGCTGCTGGAGGAAACAAGAAGGCTGCTGAGAAGTCTGAGGGAGCTA
CCGGAGTGGAGAAGGAGAAGACCACCCTCTTCCAACGTGTGAAGCAATTCTTCACCGGATC
TAAGTCTGGAGCTAAGCCAGTGGCTGGAGATGAGACCGCTAACAAGGTGAACTACCAAGAT
CTCGAGGATAACCTCAACCTCAAGGGACTCATCTCTCTCGAGGATGATCGTAACGCTAACT
TCGAGTCTAACGTGCTCAAGAACGAGAAGTTCCTCGATGAGGCTCGTGAGATCTCTAAGAA
GTCTATCCCAGAGGCTACCGTGAAGCAAATGTCTCACCTCCCAGAGTTCGATGATATCCTC
ACCGAGGGAGCTAAGAAGGTGGAGTCTCGTATCAACAAGGCTATCACCTTCCGTCCATCTG
TGGAGGAGTTCTCTGAGATCCAAGATCTCGTGAAGACCCTCCCAAAGACCAAGGTGATCGA
GGATCTCTCTACCAAGACCAACGAGATCACCGAGGCTCTCGCTGCTACCTCTAAGACCATC
CAACGTACCCCAGAGCTCAAGGAGCAACTCAAGACCGCTATCGAGGATTTCCTCCAAAACT
CTCAAGGAAAGCCACTCACCGTGCAAATGATCGAGAACCTCAACCACGGACTCCGTCCAGA

*Fig. 10A*

TGAGGGAGAGGGACGTCTCCTCTACAAGAAGGAGAACCTCACCAAGGAGAACGCTGTGTTC
TCTTCTCCAGAGGCTGCTAAGATCCAACTCGCTGAGACCGTGGATTTCATCAACCGTGCTA
AGAACGAGGGAATCGAGCCATCTGTGGTGGGAGCTCTCGTGTACCAACGTCTCATCGCTTA
CCACCCATTCGCTGAGGGAAACGGACGTATGGCTCGTGTGATCGTGAACAAGATCCTCCTC
GATGCTGGATACCCAGCTTTCACCAAGTTCTCTGATGAGTTCGAGCCACAAATCATCCCAC
AAACCAAGGCTTCTACCAAGTCTGCTACCTCTTCTGAGGTGGTGGTGGAGTTCCTCAAGGA
GCTCGCTAAGAAGGGATCTAAGGAGGATAACGAGCAAAACCTCGAGAAGACCGATCGTACC
TCTACCGATCTCACCGAGTCTGCTGTGGAGAACTCTGCTGCTCTCTCTTACCCAGCTTTCT
TGTACAAAGTGGTTGATATCGCATGCGGTACCGGCGGA*ATGGTGAGCAAGGGCGAGGAGCT*
*GTTCACCGGGGTGGTGCCCATCCTGGTCGAGCTGGACGGCGACGTAAACGGCCACAAGTTC*
*AGCGTGTCCGGCGAGGGCGAGGGCGATGCCACCTACGGCAAGCTGACCCTGAAGTTCATCT*
*GCACCACCGGCAAGCTGCCCGTGCCCTGGCCCACCCTCGTGACCACCCTGACCTACGGCGT*
*GCAGTGCTTCAGCCGCTACCCCGACCACATGAAGCAGCACGACTTCTTCAAGTCCGCCATG*
*CCCGAAGGCTACGTCCAGGAGCGCACCATCTTCTTCAAGGACGACGGCAACTACAAGACCC*
*GCGCCGAGGTGAAGTTCGAGGGCGACACCCTGGTGAACCGCATCGAGCTGAAGGGCATCGA*
*CTTCAAGGAGGACGGCAACATCCTGGGGCACAAGCTGGAGTACAACTACAACAGCCACAAC*
*GTCTATATCATGGCCGACAAGCAGAAGAACGGCATCAAGGTGAACTTCAAGATCCGCCACA*
*ACATCGAGGACGGCAGCGTGCAGCTCGCCGACCACTACCAGCAGAACACCCCCATCGGCGA*
*CGGCCCCGTGCTGCTGCCCGACAACCACTACCTGAGCACCCAGTCCGCCCTGAGCAAAGAC*
*CCCAACGAGAAGCGCGATCACATGGTCCTGCTGGAGTTCGTGACCGCCGCCGGGATCACTC*
*TCGGCATGGACGAGCTGTACAAGTAAGCGGCCGCATACTGGATTGGTGAATCAATGAGCCG*
TAGCACAATGGTTACATTCGGCTAGCTAAGATCCAATGGCAAGGACCAAGTGCTGGAACTT
GTTTTGCTTTAGCAGATCTTAGCGTGAGAGGTATTTGTCCTCTGTCAGGAGTAGATAGTAG
ATGTTCTTTTTAAACTAAAATGCTAACTGTTCCGAATTCCTCATCGCAGCTAATCCGTACA
TCAAAAGACAAAATGCTAGGTATGTGTACTACATCTCCTGTTGCTAGATAAGACATATGAT
AGGAAACACACCATCAATAGTCATTGTAGCTTTACTTATACTACGCATTTGCACTTTCCCC
TGAGTGGCAGAGGCGCATTGAGAAAATCGATCTCAACATAGTTTATGTAGCATCCCCTAGA
TCCATTACTTTAAGTCTCCTTCGTCTTTGGTGTAGGCATGTTGGACACAACGAGGTAAAAC
ACAACACAAACAATGTGTCCAGCAAAGTAGTAGCTGCTCCAGTTCTCCCGGGGGATCCACT

*Fig. 10B*

```
AGTTCTAGAGCGGCCGGCCGCCACCGCGGTGGAGCTCCAGCTTTTGTTCCCTTTAGTGAGG
GTTAATTGCGCGCTTGGCGTAATCATGGTCATAGCTGTTTCCTGTGTGAAATTGTTATCCG
CTCACAATTCCACACAACATACGAGCCGGAAGCATAAAGTGTAAAGCCTGGGGTGCCTAAT
GAGTGAGCTAACTCACATTAATTGCGTTGCGCTCACTGCCCGCTTTCCAGTCGGGAAACCT
GTCGTGCCAGCTGCATTAATGAATCGGCCAACGCGCGGGGAGAGGCGGTTTGCGTATTGGG
CGCTCTTCCGCTTCCTCGCTCACTGACTCGCTGCGCTCGGTCGTTCGGCTGCGGCGAGCGG
TATCAGCTCACTCAAAGGCGGTAATACGGTTATCCACAGAATCAGGGGATAACGCAGGAAA
GAACATGTGAGCAAAAGGCCAGCAAAAGGCCAGGAACCGTAAAAAGGCCGCGTTGCTGGCG
TTTTTCCATAGGCTCCGCCCCCTGACGAGCATCACAAAAATCGACGCTCAAGTCAGAGGT
GGCGAAACCCGACAGGACTATAAAGATACCAGGCGTTTCCCCCTGGAAGCTCCCTCGTGCG
CTCTCCTGTTCCGACCCTGCCGCTTACCGGATACCTGTCCGCCTTTCTCCCTTCGGGAAGC
GTGGCGCTTTCTCATAGCTCACGCTGTAGGTATCTCAGTTCGGTGTAGGTCGTTCGCTCCA
AGCTGGGCTGTGTGCACGAACCCCCCGTTCAGCCCGACCGCTGCGCCTTATCCGGTAACTA
TCGTCTTGAGTCCAACCCGGTAAGACACGACTTATCGCCACTGGCAGCAGCCACTGGTAAC
AGGATTAGCAGAGCGAGGTATGTAGGCGGTGCTACAGAGTTCTTGAAGTGGTGGCCTAACT
ACGGCTACACTAGAAGGACAGTATTTGGTATCTGCGCTCTGCTGAAGCCAGTTACCTTCGG
AAAAAGAGTTGGTAGCTCTTGATCCGGCAAACAAACCACCGCTGGTAGCGGTGGTTTTTTT
GTTTGCAAGCAGCAGATTACGCGCAGAAAAAAAGGATCTCAAGAAGATCCTTTGATCTTTT
CTACGGGGTCTGACGCTCAGTGGAACGAAAACTCACGTTAAGGGATTTTGGTCATGAGATT
ATCAAAAGGATCTTCACCTAGATCCTTTTAAATTAAAAATGAAGTTTTAAATCAATCTAA
AGTATATATGAGTAAACTTGGTCTGACAGTTACCAATGCTTAATCAGTGAGGCACCTATCT
CAGCGATCTGTCTATTTCGTTCATCCATAGTTGCCTGACTCCCCGTCGTGTAGATAACTAC
GATACGGGAGGGCTTACCATCTGGCCCCAGTGCTGCAATGATACCGCGAGACCCACGCTCA
CCGGCTCCAGATTTATCAGCAATAAACCAGCCAGCCGGAAGGGCCGAGCGCAGAAGTGGTC
CTGCAACTTTATCCGCCTCCATCCAGTCTATTAATTGTTGCCGGGAAGCTAGAGTAAGTAG
TTCGCCAGTTAATAGTTTGCGCAACGTTGTTGCCATTGCTACAGGCATCGTGGTGTCACGC
TCGTCGTTTGGTATGGCTTCATTCAGCTCCGGTTCCCAACGATCAAGGCGAGTTACATGAT
CCCCCATGTTGTGCAAAAAAGCGGTTAGCTCCTTCGGTCCTCCGATCGTTGTCAGAAGTAA
```

*Fig. 10C*

```
GTTGGCCGCAGTGTTATCACTCATGGTTATGGCAGCACTGCATAATTCTCTTACTGTCATG
CCATCCGTAAGATGCTTTTCTGTGACTGGTGAGTACTCAACCAAGTCATTCTGAGAATAGT
GTATGCGGCGACCGAGTTGCTCTTGCCCGGCGTCAATACGGGATAATACCGCGCCACATAG
CAGAACTTTAAAAGTGCTCATCATTGGAAAACGTTCTTCGGGGCGAAAACTCTCAAGGATC
TTACCGCTGTTGAGATCCAGTTCGATGTAACCCACTCGTGCACCCAACTGATCTTCAGCAT
CTTTTACTTTCACCAGCGTTTCTGGGTGAGCAAAACAGGAAGGCAAATGCCGCAAAAAA
GGGAATAAGGGCGACACGGAAATGTTGAATACTCATACTCTTCCTTTTTCAATATTATTGA
AGCATTTATCAGGGTTATTGTCTCATGAGCGGATACATATTTGAATGTATTTAGAAAAATA
AACAAATAGGGGTTCCGCGCACATTTCCCCGAAAAGTGCCACCTAAATTGTAAGCGTTAAT
ATTTTGTTAAAATTCGCGTTAAATTTTTGTTAAATCAGCTCATTTTTTAACCAATAGGCCG
AAATCGGCAAAATCCCTTATAAATCAAAAGAATAGACCGAGATAGGGTTGAGTGTTGTTCC
AGTTTGGAACAAGAGTCCACTATTAAAGAACGTGGACTCCAACGTCAAAGGGCGAAAAACC
GTCTATCAGGGCGATGGCCCACTACGTGAACCATCACCCTAATCAAGTTTTTTGGGGTCGA
GGTGCCGTAAAGCACTAAATCGGAACCCTAAAGGGAGCCCCCGATTTAGAGCTTGACGGGG
AAAGCCGGCGAACGTGGCGAGAAAGGAAGGGAAGAAAGCGAAAGGAGCGGGCGCTAGGGCG
CTGGCAAGTGTAGCGGTCACGCTGCGCGTAACCACCACACCCGCCGCGCTTAATGCGCCGC
TACAGGGCGCGTCCCATTCGCCATTCAGGCTGCGCAACTGTTGGGAAGGGCGATCGGTGCG
GGCCTCTTCGCTATTACGCCAGCTGGCGAAAGGGGGATGTGCTGCAAGGCGATTAAGTTGG
GTAACGCCAGGGTTTTCCCAGTCACGACGTTGTAAAACGACGGCCAGTGAGCGCGCGTAAT
ACGACTCACTATAGGGCGAATTGGGTACGTACCGGGCCCCCCCTCGAGGTCGACGGTATCG
ATA
(SEQ ID NO:10)
```

Underlined = FCP promoter and terminator
Bold = GWB fragment
Double Underlined = DR2 domain with start codon added (codon biased for expression in a diatom)
*Italic = eGFP*

*Fig. 10D*

SEQUENCE LISTING

<160> NUMBER OF SEQ ID NOS: 24

<210> SEQ ID NO 1
<211> LENGTH: 966
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1

```
gcgcttttc cgagaactcc ccataagtca acggctccaa tcaagaatgt atccgacaac       60
ggcgagcata gcaacacgtc cgtctttgga gtagaatcat catgttgtgg atgaatacac     120
agatgaatga cattaaaagc atgaacatgt tagagagtag gaggtagaga ttgatatggt     180
agcattgcga tgtttgtttt tggtcagcat atgatgagtg gataccaata tgatgaaagt     240
tgaatctcgc gtttgagctc agcggtacgt tattgatcga aagtagcctg atcaaaatcc     300
ttggagagta caagaggatc aaagaatcca gtgggggcga taactccaag ctcgttctca     360
aagaggcaat ggaggtagaa actcatccca gttgagaaga agtgaaggca gtggcggtgg     420
cgaaagcaga ggcaacgagg acagacttcc tgtgggttga tgcaacgaat atttccagaa     480
ggagaagttt agagagttga accgctacct acaatgacaa agtatcgtat cgattttgat     540
gttggttggt tatgaattca aactgtaagt tggattgtga aagatcaga agttaacga       600
acacatcttt ccgatcattc acctccacac tgcaacaaca cggtacttct tccgcggcag     660
gtctctgtcg ccattctctt gtcctgttgt tggctgtgag acgaggaaag caacgacaag     720
tttcacaaaa gggagttcct ttaacgagat atgttttta taaagagtcc aatagaaag      780
acaaattgat tcctccgtgc aaacgcgcaa ataaacacca cgtccattat atccatatct     840
ttcagagtat ccaacaagtg ttgaaggaca ggtagttgaa gtaacgtatc ttccccctcg     900
actggatcca tcaacaaggc gaacaaatcc attcaacctc tcataaatta tctgatttac     960
caaacc                                                                966
```

<210> SEQ ID NO 2
<211> LENGTH: 508
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

```
gcggccgcat actggattgg tgaatcaatg agccgtagca caatggttac attcggctag       60
ctaagatcca atggcaagga ccaagtgctg gaacttgttt tgctttagca gatcttagcg     120
tgagaggtat ttgtcctctg tcaggagtag atagtgatg ttcttttaa actaaaatgc       180
taactgttcc gaattcctca tcgcagctaa tccgtacatc aaaagacaaa atgctaggta     240
tgtgtactac atctcctgtt gctagataag acatatgata ggaaacacac catcaatagt     300
cattgtagct ttacttatac tacgcatttg cactttcccc tgagtggcag aggcgcattg     360
agaaaatcga tctcaacata gtttatgtag catcccctag atccattact ttaagtctcc     420
ttcgtctttg gtgtaggcat gttggacaca acgaggtaaa acacaacaca aacaatgtgt     480
ccagcaaagt agtagctgct ccagttct                                        508
```

<210> SEQ ID NO 3
<211> LENGTH: 1186

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
atgtctgtaa atgaagttgc accgttgtca tctgtaccag cagaactaaa agatgctgct      60
ggaggaaata aaaaagcggc agagaaatca gagggtgcta cgggtgtaga aaagaaaaa     120
accacacttt tccaacgagt gaaacaattt ttcaccggaa gtaagagcgg tgcgaaacct    180
gtagcgggag atgagacagc gaataaagtc aattatcaag atttggaaga taatttgaac    240
ttaaaaggat taatttcttt agaagatgat cgaaatgcta attttgaaag taatgtattg    300
aaaaatgaga aatttttaga tgaagcaaga gagatttcga agaaatcaat tcctgaagcg    360
acagttaagc aaatgtctca tttacctgaa tttgatgata ttctcaccga gggagctaag    420
aaagtagaaa gtcgtattaa taaggcaatc acattccgcc cttctgttga ggagttttca    480
gaaattcaag atttggtgaa aacgttaccg aaaacaaagg ttatagagga tctttcaaca    540
aaaacaaatg aaatcacaga agctttagct gcgacatcga aaaccattca acgtacaccg    600
gagttgaaag aacagttgaa gacagcaata gaggatttct acaaaacag tcaaggcaaa    660
cctttgacag tgcagatgat cgagaatctt aatcacggat acgtccgga tgagggagaa    720
ggtcgtttac tttataaaaa agagaattta accaaagaaa atgcggtatt ttctagtccc    780
gaagcggcaa aaattcaatt agcggaaacg gttgatttta tcaatcgagc gaaaaatgaa    840
gggattgagc cgagtgtggt tggggcatta gtttatcagc gattgattgc ttatcaccca    900
tttgcagaag gtaatggacg tatggcgaga gtcatagtaa ataaaatttt acttgatgca    960
ggttatccgg catttaccaa atttagtgat gagtttgaac cgcagattat tcctcaaacg    1020
aaagcatcaa ctaaatccgc aacgagcagt gaagtggtag ttgagttttt aaaagagttg   1080
gcaaaaaaag gaagcaagga agataacgag cagaatttag aaaaaactga ccgcacttct   1140
acggacttga cagaaagtgc ggtagaaaat tcggctgctt tgagtt                  1186
```

<210> SEQ ID NO 4
<211> LENGTH: 1185
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

```
atgtctgtga acgaggtggc tccactctct tctgtgccag ctgagctcaa ggatgctgct      60
ggaggaaaca agaaggctgc tgagaagtct gagggagcta ccggagtgga aaggagaag     120
accacccctct tccaacgtgt gaagcaattc ttcaccggat ctaagtctgg agctaagcca   180
gtggctggag atgagaccgc taacaaggtg aactaccaag atctcgagga taacctcaac   240
ctcaagggac tcatctctct cgaggatgat cgtaacgcta acttcgagtc taacgtgctc   300
aagaacgaga gttcctcga tgaggctcgt gagatctcta agagtctat cccagaggct    360
accgtgaagc aaatgtctca cctcccagag ttcgatgata tcctcaccga gggagctaag    420
aaggtggagt ctcgtatcaa caaggctatc accttccgtc catctgtgga ggagttctct   480
gagatccaag atctcgtgaa gaccctccca aagaccaagg tgatcgagga tctctctacc   540
aagaccaacg agatcaccga ggctctcgct gctacctcta gaccatcca acgtaccccca   600
```

```
gagctcaagg agcaactcaa gaccgctatc gaggatttcc tccaaaactc tcaaggaaag    660
ccactcaccg tgcaaatgat cgagaacctc aaccacggac tccgtccaga tgagggagag    720
ggacgtctcc tctacaagaa ggagaacctc accaaggaga acgctgtgtt ctcttctcca    780
gaggctgcta agatccaact cgctgagacc gtggatttca tcaaccgtgc taagaacgag    840
ggaatcgagc atctgtggt gggagctctc gtgtaccaac gtctcatcgc ttaccaccca    900
ttcgctgagg gaaacggacg tatggctcgt gtgatcgtga acaagatcct cctcgatgct    960
ggatacccag ctttcaccaa gttctctgat gagttcgagc acaaatcat cccacaaacc    1020 aaggcttcta ccaagtctgc tacctcttct gaggtggtgg tggagttcct caaggagctc    1080
gctaagaagg gatctaagga ggataacgag caaaacctcg agaagaccga tcgtacctct    1140
accgatctca ccgagtctgc tgtggagaac tctgctgctc tctct                   1185
```

<210> SEQ ID NO 5
<211> LENGTH: 395
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Met Ser Val Asn Glu Val Ala Pro Leu Ser Ser Val Pro Ala Glu Leu
1               5                   10                  15

Lys Asp Ala Ala Gly Gly Asn Lys Lys Ala Glu Lys Ser Glu Gly
            20                  25                  30

Ala Thr Gly Val Glu Lys Glu Lys Thr Thr Leu Phe Gln Arg Val Lys
        35                  40                  45

Gln Phe Phe Thr Gly Ser Lys Ser Gly Ala Lys Pro Val Ala Gly Asp
    50                  55                  60

Glu Thr Ala Asn Lys Val Asn Tyr Gln Asp Leu Glu Asp Asn Leu Asn
65                  70                  75                  80

Leu Lys Gly Leu Ile Ser Leu Glu Asp Asp Arg Asn Ala Asn Phe Glu
                85                  90                  95

Ser Asn Val Leu Lys Asn Glu Lys Phe Leu Asp Glu Ala Arg Glu Ile
            100                 105                 110

Ser Lys Lys Ser Ile Pro Glu Ala Thr Val Lys Gln Met Ser His Leu
        115                 120                 125

Pro Glu Phe Asp Asp Ile Leu Thr Glu Gly Ala Lys Lys Val Glu Ser
    130                 135                 140

Arg Ile Asn Lys Ala Ile Thr Phe Arg Pro Ser Val Glu Glu Phe Ser
145                 150                 155                 160

Glu Ile Gln Asp Leu Val Lys Thr Leu Pro Lys Thr Lys Val Ile Glu
                165                 170                 175

Asp Leu Ser Thr Lys Thr Asn Glu Ile Thr Glu Ala Leu Ala Ala Thr
            180                 185                 190

Ser Lys Thr Ile Gln Arg Thr Pro Glu Leu Lys Glu Gln Leu Lys Thr
        195                 200                 205

Ala Ile Glu Asp Phe Leu Gln Asn Ser Gln Gly Lys Pro Leu Thr Val
    210                 215                 220

Gln Met Ile Glu Asn Leu Asn His Gly Leu Arg Pro Asp Glu Gly Glu
225                 230                 235                 240

Gly Arg Leu Leu Tyr Lys Lys Glu Asn Leu Thr Lys Glu Asn Ala Val
                245                 250                 255
```

```
Phe Ser Ser Pro Glu Ala Ala Lys Ile Gln Leu Ala Glu Thr Val Asp
                260                 265                 270

Phe Ile Asn Arg Ala Lys Asn Glu Gly Ile Glu Pro Ser Val Val Gly
            275                 280                 285

Ala Leu Val Tyr Gln Arg Leu Ile Ala Tyr His Pro Phe Ala Glu Gly
        290                 295                 300

Asn Gly Arg Met Ala Arg Val Ile Val Asn Lys Ile Leu Leu Asp Ala
305                 310                 315                 320

Gly Tyr Pro Ala Phe Thr Lys Phe Ser Asp Glu Phe Glu Pro Gln Ile
            325                 330                 335

Ile Pro Gln Thr Lys Ala Ser Thr Lys Ser Ala Thr Ser Ser Glu Val
            340                 345                 350

Val Val Glu Phe Leu Lys Glu Leu Ala Lys Lys Gly Ser Lys Glu Asp
        355                 360                 365

Asn Glu Gln Asn Leu Glu Lys Thr Asp Arg Thr Ser Thr Asp Leu Thr
370                 375                 380

Glu Ser Ala Val Glu Asn Ser Ala Ala Leu Ser
385                 390                 395

<210> SEQ ID NO 6
<211> LENGTH: 397
<212> TYPE: PRT
<213> ORGANISM: Thalassiosira pseudonana

<400> SEQUENCE: 6

Cys Thr Gly Asp Cys Asp Ser Asp Thr Asp Cys Leu Pro Thr Leu Lys
1               5                   10                  15

Cys Phe Lys Arg Gly Asp Gly Glu Ser Thr Gln Val Pro Gly Cys Gly
            20                  25                  30

Thr Gly Gly Val Gly Asp Ile Pro Gly Ala Asp Tyr Cys Tyr Asp Pro
        35                  40                  45

Ser Asn Gly Asp Val Ser Arg Val Asn Gly Cys Thr Pro Ser Thr Gln
50                  55                  60

Cys Asn Ile Cys Ser Gly Asp Cys Asp Asn Asp Glu Asp Cys Ile Gly
65                  70                  75                  80

Asp Tyr Leu Cys Phe Lys Arg Ala Asp Gly Met Lys Asn Gln Val Pro
            85                  90                  95

Gly Cys Glu Ile Gly Gly Ile Gly Asp Ile Ser Gly Ala Asp Tyr Cys
        100                 105                 110

Tyr Asp Pro Ser Gly Gly Gly Leu Ser Pro Thr Gly Ser Pro Ser Val
        115                 120                 125

Gly Gly Val Met Thr Asp Ala Pro Gln Val Ala Thr Leu Asn Pro Ser
130                 135                 140

Val Ser Pro Thr Phe Ala Leu Pro Ser Lys Val Ser Pro Leu Pro Thr
145                 150                 155                 160

Asp Ile Asn Leu Leu Val Gly Asn Pro Phe Ala Thr Pro Ser Ala Ala
            165                 170                 175

Pro Thr Ser Ser Leu Pro Ser Leu Arg Tyr His Gly Arg Asn Met Cys
        180                 185                 190

Thr Ala Asp Ser Pro Cys Gly Ala Cys Ser Gly Asp Cys Asp Gly Asp
        195                 200                 205

Ser Gly Cys Gln Thr Gly Leu Met Cys Phe Gln Arg Ala Arg Asp Glu
        210                 215                 220

Thr Ser Gln Val Pro Gly Cys Ala Val Gly Gly Thr Glu Asp Ile Pro
225                 230                 235                 240
```

```
Gly Ala Asp Tyr Cys Tyr Asp Pro Thr Ser Glu Ser Pro Pro Leu Val
                245                 250                 255

Trp Leu Gly Glu Asp Gly Cys Ser Glu Asp Gln Pro Cys Asn Arg Cys
            260                 265                 270

Ala Gly Ser Cys Ser Asn Asp Glu Asp Cys Lys Gly Asn Leu Glu Cys
        275                 280                 285

Phe Val Arg Ile Asp Gly Glu Ser Thr Ser Val Pro Gly Cys Ser Ser
    290                 295                 300

Gly Gly Ile Gly Asp Val Leu Glu Asp Tyr Cys Tyr Asp Pro Asp Ala
305                 310                 315                 320

Ala Phe Thr Pro Ser Pro Thr Arg Thr Pro Ser Ser Leu Pro Thr Leu
                325                 330                 335

Arg Trp Arg Gly Ser Glu Gly Cys Ser Pro Asp Ser Pro Cys Pro Ser
            340                 345                 350

Cys Thr Gly Asp Cys Asp Asn Asp Asn Asp Cys Asp Ser Thr Leu Lys
        355                 360                 365

Cys Phe Lys Arg Phe Ala Gly Asp Arg Thr Gln Val Pro Gly Cys Ala
    370                 375                 380

Thr Gly Gly Leu Gly Asp Ile Pro Gly Gly Asp Tyr Cys
385                 390                 395

<210> SEQ ID NO 7
<211> LENGTH: 134
<212> TYPE: PRT
<213> ORGANISM: Thalassiosira pseudonana

<400> SEQUENCE: 7

Cys Gln Gly Asp Cys Asn Ser Asp Ala Asp Cys Ala Gly Gly Leu Met
1               5                  10                  15

Cys Phe Ser Arg Gly Thr Gly Glu Val Thr Ser Val Pro Gly Cys Val
            20                  25                  30

Ser Gly Gly Glu Gly Asp Leu Pro Gly Met Asp Tyr Cys Tyr Thr Pro
        35                  40                  45

Phe Pro Pro Glu Thr Thr Thr Ala Thr Thr Ser Thr Thr Thr Thr Thr
    50                  55                  60

Thr Ser Thr Thr Thr Ala Thr Ala Pro Asp Leu Asn Phe Val Arg Glu
65                  70                  75                  80

Cys Thr Ala Glu Asp Pro Cys Asn Ala Cys Glu Gly Asp Cys Asp Asp
                85                  90                  95

His Thr His Cys Ala Gly Ser Leu Glu Cys Phe Ser Arg Asp Gln Gly
            100                 105                 110

Ser Val Asp Leu Val Pro Gly Cys Asn Gly Leu Gly Val Ala Gly Met
        115                 120                 125

Asp Tyr Cys Tyr Asp Pro
    130

<210> SEQ ID NO 8
<211> LENGTH: 6882
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
agcttgcgct ttttccgaga actccccata agtcaacggc tccaatcaag aatgtatccg    60
```

```
acaacggcga gcatagcaac acgtccgtct ttggagtaga atcatcatgt tgtggatgaa    120
tacacagatg aatgcacatta aaagcatgaa catgttagag agtaggaggt agagattgat    180
atggtagcat tgcgatgttt gttttggtc agcatatgat gagtggatac caatatgatg     240
aaagttgaat ctcgcgtttg agctcagcgg tacgttattg atcgaaagta gcctgatcaa    300
aatccttgga gagtacaaga ggatcaaaga atccagtggg ggcgataact ccaagctcgt    360
tctcaaagag gcaatggagg tagaaactca tcccagttga gaagaagtga aggcagtggc    420
ggtggcgaaa gcagaggcaa cgaggacaga cttcctgtgg gttgatgcaa cgaatatttc    480
cagaaggaga agtttagaga gttgaaccgc tacctacaat gacaaagtat cgtatcgatt    540
ttgatgttgg ttggttatga attcaaactg taagttggat tgtgagaaga tcagaagttg    600
aacgaacaca tctttccgat cattcacctc cacactgcaa caacacggta cttcttccgc    660
ggcaggtctc tgtcgccatt ctcttgtcct gttgttggct gtgagacgag gaaagcaacg    720
acaagtttca caaagggag ttcctttaac gagatatgtt ttttataaag agtcccaata     780
gaaagacaaa ttgattcctc cgtgcaaacg cgcaaataaa caccacgtcc attatatcca    840
tatctttcag agtatccaac aagtgttgaa ggacaggtag ttgaagtaac gtatcttccc    900
cctcgactgg atccatcaac aaggcgaaca aatccattca acctctcata aattatctga    960
tttaccaaac cgatatcaac aagtttgtac aaaaagctg aacgagaaac gtaaaatgat     1020
ataaatatca atatattaaa ttagattttg cataaaaaac agactacata atactgtaaa    1080
acacaacata tccagtcact atggcggccg cattaggcac cccaggcttt acactttatg    1140
cttccggctc gtataatgtg tggattttga gttaggatcc gtcagatttt tcaggagcta    1200
aggaagctaa aatggagaaa aaaatcactg gatataccac cgttgatata tcccaatggc    1260
atcgtaaaga acattttgag gcatttcagt cagttgctca atgtacctat aaccagaccg    1320
ttcagctgga tattacggcc ttttttaaaga ccgtaaagaa aaataagcac aagttttatc    1380
cggcctttat tcacattctt gcccgcctga tgaatgctca tccggaattc cgtatggcaa    1440
tgaaagacgg tgagctggtg atatgggata gtgttcaccc ttgttacacc gttttccatg    1500
agcaaactga aacgttttca tcgctctgga gtgaatacca cgacgatttc cggcagtttc    1560
tacacatata ttcgcaagat gtggcgtgtt acggtgaaaa cctggcctat ttccctaaag    1620
ggtttattga gaatatgttt ttcgtctcag ccaatccctg ggtgagtttc accagttttg    1680
atttaaacgt ggccaatatg gacaacttct tcgccccgt tttcaccatg ggcaaatatt     1740
atacgcaagg cgacaaggtg ctgatgccgc tggcgattca ggttcatcat gccgtttgtg    1800
atggcttcca tgtcggcaga atgcttaatg aattacaaca gtactgcgat gagtggcagg    1860
gcggggcgta aagatctgga tccggcttac taaaagccag ataacagtat gcgtatttgc    1920
gcgctgattt ttgcggtata agaatatata ctgatatgta tacccgaagt atgtcaaaaa    1980
gaggtatgct atgaagcagc gtattacagt gacagttgac agcgacagct atcagttgct    2040
caaggcatat atgatgtcaa tatctccggt ctggtaagca caaccatgca gaatgaagcc    2100
cgtcgtctgc gtgccgaacg ctggaaagcg gaaaatcagg aagggatggc tgaggtcgcc    2160
cggtttattg aaatgaacgg ctcttttgct gacgagaaca ggggctggtg aaatgcagtt    2220
taaggtttac acctataaaa gagagagccg ttatcgtctg tttgtggatg tacagagtga    2280
tattattgac acgcccgggc gacggatggt gatcccctg ccagtgcac gtctgctgtc     2340 agataaagtc tcccgtgaac tttacccggt ggtgcatatc ggggatgaaa gctggcgcat    2400
gatgaccacc gatatggcca gtgtgccggt ctccgttatc ggggaagaag tggctgatct    2460
```

```
cagccaccgc gaaaatgaca tcaaaaacgc cattaacctg atgttctggg gaatataaat    2520
gtcaggctcc cttatacaca gccagtctgc aggtcgacca tagtgactgg atatgttgtg    2580
ttttacagta ttatgtagtc tgttttttat gcaaaatcta atttaatata ttgatattta    2640
tatcatttta cgtttctcgt tcagcttcct tgtacaaagt ggttgatatc gcatgcggta    2700
ccggcggaat ggtgagcaag ggcgaggagc tgttcaccgg ggtggtgccc atcctggtcg    2760
agctggacgg cgacgtaaac ggccacaagt tcagcgtgtc cggcgagggc gagggcgatg    2820
ccacctacgg caagctgacc ctgaagttca tctgcaccac cggcaagctg cccgtgccct    2880
ggcccaccct cgtgaccacc ctgacctacg gcgtgcagtg cttcagccgc taccccgacc    2940
acatgaagca gcacgacttc ttcaagtccg ccatgcccga aggctacgtc caggagcgca    3000
ccatcttctt caaggacgac ggcaactaca agacccgcgc cgaggtgaag ttcgagggcg    3060
acaccctggt gaaccgcatc gagctgaagg gcatcgactt caaggaggac ggcaacatcc    3120
tggggcacaa gctggagtac aactacaaca gccacaacgt ctatatcatg gccgacaagc    3180
agaagaacgg catcaaggtg aacttcaaga tccgccacaa catcgaggac ggcagcgtgc    3240
agctcgccga ccactaccag cagaacaccc ccatcggcga cggccccgtg ctgctgcccg    3300
acaaccacta cctgagcacc cagtccgccc tgagcaaaga ccccaacgag aagcgcgatc    3360
acatggtcct gctggagttc gtgaccgccg ccgggatcac tctcggcatg gacgagctgt    3420
acaagtaagc ggccgcatac tggattggtg aatcaatgag ccgtagcaca atggttacat    3480
tcggctagct aagatccaat ggcaaggacc aagtgctgga acttgttttg ctttagcaga    3540
tcttagcgtg agaggtattt gtcctctgtc aggagtagat agtagatgtt cttttttaaac   3600 taaaatgcta actgttccga attcctcatc gcagctaatc cgtacatcaa agacaaaat    3660 gctaggtatg tgtactacat ctcctgttgc tagataagac atatgatagg aaacacacca    3720
tcaatagtca ttgtagcttt acttatacta cgcatttgca cttttccctg agtggcagag    3780
gcgcattgag aaaatcgatc tcaacatagt ttatgtagca tcccctagat ccattacttt    3840
aagtctcctt cgtctttggt gtaggcatgt tggacacaac gaggtaaaac acaacacaaa    3900
caatgtgtcc agcaaagtag tagctgctcc agttctcccg ggggatccac tagttctaga    3960
gcggccggcc gccaccgcgg tggagctcca gcttttgttc cctttagtga gggttaattg    4020
cgcgcttggc gtaatcatgg tcatagctgt ttcctgtgtg aaattgttat ccgctcacaa    4080
ttccacacaa catacgagcc ggaagcataa agtgtaaagc ctggggtgcc taatgagtga    4140
gctaactcac attaattgcg ttgcgctcac tgcccgcttt ccagtcggga aacctgtcgt    4200
gccagctgca ttaatgaatc ggccaacgcg cggggagagg cggtttgcgt attgggcgct    4260
cttccgcttc ctcgctcact gactcgctgc gctcggtcgt tcggctgcgg cgagcggtat    4320
cagctcactc aaaggcggta atacggttat ccacagaatc aggggataac gcaggaaaga    4380
acatgtgagc aaaaggccag caaaaggcca ggaaccgtaa aaaggccgcg ttgctggcgt    4440
ttttccatag gctccgcccc cctgacgagc atcacaaaaa tcgacgctca agtcagaggt    4500
ggcgaaaccc gacaggacta taaagatacc aggcgtttcc ccctggaagc tccctcgtgc    4560
gctctcctgt tccgaccctg ccgcttaccg gatacctgtc cgcctttctc ccttcgggaa    4620
gcgtggcgct ttctcatagc tcacgctgta ggtatctcag ttcggtgtag gtcgttcgct    4680
ccaagctggg ctgtgtgcac gaaccccccg ttcagcccga ccgctgcgcc ttatccggta    4740
actatcgtct tgagtccaac ccggtaagac acgacttatc gccactggca gcagccactg    4800
```

```
gtaacaggat tagcagagcg aggtatgtag gcggtgctac agagttcttg aagtggtggc    4860
ctaactacgg ctacactaga aggacagtat ttggtatctg cgctctgctg aagccagtta    4920
ccttcggaaa aagagttggt agctcttgat ccggcaaaca accaccgct ggtagcggtg     4980 gttttttgt ttgcaagcag cagattacgc gcagaaaaaa aggatctcaa gaagatcctt    5040 tgatctttc tacggggtct gacgctcagt ggaacgaaaa ctcacgttaa gggattttgg    5100
tcatgagatt atcaaaaagg atcttcacct agatcctttt aaattaaaaa tgaagtttta    5160
aatcaatcta agtatatat gagtaaactt ggtctgacag ttaccaatgc ttaatcagtg     5220
aggcacctat ctcagcgatc tgtctatttc gttcatccat agttgcctga ctccccgtcg    5280
tgtagataac tacgatacgg gagggcttac catctggccc cagtgctgca atgataccgc    5340
gagacccacg ctcaccggct ccagatttat cagcaataaa ccagccagcc ggaagggccg    5400
agcgcagaag tggtcctgca actttatccg cctccatcca gtctattaat tgttgccggg    5460
aagctagagt aagtagttcg ccagttaata gtttgcgcaa cgttgttgcc attgctacag    5520
gcatcgtggt gtcacgctcg tcgtttggta tggcttcatt cagctccggt tcccaacgat    5580
caaggcgagt tacatgatcc cccatgttgt gcaaaaaagc ggttagctcc ttcggtcctc    5640
cgatcgttgt cagaagtaag ttggccgcag tgttatcact catggttatg gcagcactgc    5700
ataattctct tactgtcatg ccatccgtaa gatgcttttc tgtgactggt gagtactcaa    5760
ccaagtcatt ctgagaatag tgtatgcggc gaccgagttg ctcttgcccg gcgtcaatac    5820
gggataatac cgcgccacat agcagaactt taaaagtgct catcattgga aaacgttctt    5880
cggggcgaaa actctcaagg atcttaccgc tgttgagatc cagttcgatg taacccactc    5940
gtgcacccaa ctgatcttca gcatctttta ctttcaccag cgtttctggg tgagcaaaaa    6000
caggaaggca aaatgccgca aaaaagggaa taagggcgac acggaaatgt tgaatactca    6060
tactcttcct ttttcaatat tattgaagca tttatcaggg ttattgtctc atgagcggat    6120
acatatttga atgtatttag aaaaataaac aaataggggt tccgcgcaca tttccccgaa    6180
aagtgccacc taaattgtaa gcgttaatat tttgttaaaa ttcgcgttaa attttgtta    6240 aatcagctca tttttaacc aataggccga atcggcaaa atcccttata atcaaaaga     6300 atagaccgag ataggggttga gtgttgttcc agtttggaac aagagtccac tattaaagaa    6360
cgtggactcc aacgtcaaag ggcgaaaaac cgtctatcag ggcgatggcc cactacgtga    6420
accatcaccc taatcaagtt ttttggggtc gaggtgccgt aaagcactaa atcggaaccc    6480
taaagggagc ccccgattta gagcttgacg ggggaaagccg gcgaacgtgg cgagaaagga    6540
agggaagaaa gcgaaaggag cgggcgctag gcgctggca agtgtagcgg tcacgctgcg    6600
cgtaaccacc acaccccgccg cgcttaatgc gccgctacag ggcgcgtccc attcgccatt    6660
caggctgcgc aactgttggg aagggcgatc ggtgcgggcc tcttcgctat tacgccagct    6720
ggcgaaaggg ggatgtgctg caaggcgatt aagttgggta acgccagggt tttcccagtc    6780
acgacgttgt aaaacgacgg ccagtgagcg cgcgtaatac gactcactat agggcgaatt    6840
gggtacgtac cgggccccccc ctcgaggtcg acggtatcga ta                       6882
```

<210> SEQ ID NO 9
<211> LENGTH: 6409
<212> TYPE: DNA
<213> ORGANISM: Artificial Sequence
<220> FEATURE:
<223> OTHER INFORMATION: Description of Artificial Sequence: Synthetic polynucleotide

```
<400> SEQUENCE: 9
agcttgcgct ttttccgaga actccccata agtcaacggc tccaatcaag aatgtatccg      60
acaacggcga gcatagcaac acgtccgtct ttggagtaga atcatcatgt tgtggatgaa     120
tacacagatg aatgcatta aaagcatgaa catgttagag agtaggaggt agagattgat      180
atggtagcat tgcgatgttt gttttggtc agcatatgat gagtggatac caatatgatg     240
aaagttgaat ctcgcgtttg agctcagcgg tacgttattg atcgaaagta gcctgatcaa     300
aatccttgga gagtacaaga ggatcaaaga atccagtggg ggcgataact ccaagctcgt     360
tctcaaagag gcaatggagg tagaaactca tcccagttga gaagaagtga aggcagtggc     420
ggtggcgaaa gcagaggcaa cgaggacaga cttcctgtgg gttgatgcaa cgaatatttc     480
cagaaggaga agtttagaga gttgaaccgc tacctacaat gacaaagtat cgtatcgatt     540
ttgatgttgg ttggttatga attcaaactg taagttggat tgtgagaaga tcagaagttg     600
aacgaacaca tctttccgat cattcacctc cacactgcaa caacacggta cttcttccgc     660
ggcaggtctc tgtcgccatt ctcttgtcct gttgttggct gtgagacgag gaaagcaacg     720
acaagtttca caaagggag ttcctttaac gagatatgtt ttttataaag agtcccaata     780
gaaagacaaa ttgattcctc cgtgcaaacg cgcaaataaa caccacgtcc attatatcca     840
tatctttcag agtatccaac aagtgttgaa ggacaggtag ttgaagtaac gtatcttccc     900
cctcgactgg atccatcaac aaggcgaaca atccattca acctctcata aattatctga     960
tttaccaaac cgatatcaac aagtttgtac aaaaagcat gtctgtaaat gaagttgcac    1020
cgttgtcatc tgtaccagca gaactaaaag atgctgctgg aggaaataaa aaagcggcag    1080
agaaatcaga gggtgctacg ggtgtagaaa agaaaaaac cacactttc caacgagtga     1140
aacaatttt caccggaagt aagagcggtg cgaaacctgt agcgggagat gagacagcga    1200
ataaagtcaa ttatcaagat ttggaagata atttgaactt aaaaggatta atttctttag    1260
aagatgatcg aaatgctaat tttgaaagta atgtattgaa aaatgagaaa ttttagatg    1320
aagcaagaga gatttcgaag aaatcaattc ctgaagcgac agttaagcaa atgtctcatt    1380
tacctgaatt tgatgatatt ctcaccgagg gagctaagaa agtagaaagt cgtattaata    1440
aggcaatcac attccgccct tctgttgagg agttttcaga aattcaagat ttggtgaaaa    1500
cgttaccgaa aacaaaggtt atagaggatc tttcaacaaa aacaaatgaa atcacagaag    1560
ctttagctgc gacatcgaaa accattcaac gtacaccgga gttgaaagaa cagttgaaga    1620
cagcaataga ggatttctta caaaacagtc aaggcaaacc tttgacagtg cagatgatcg    1680
agaatcttaa tcacggatta cgtccggatg agggagaagg tcgtttactt tataaaaaag    1740
agaatttaac caaagaaaat gcggtatttt ctagtcccga agcggcaaaa attcaattag    1800
cggaaacggt tgatttttatc aatcgagcga aaaatgaagg gattgagccg agtgtggttg    1860
gggcattagt ttatcagcga ttgattgctt atcacccatt tgcagaaggt aatgacgta    1920
tggcgagagt catagtaaat aaaatttac ttgatgcagg ttatccggca tttaccaaat    1980
ttagtgatga gtttgaaccg cagattattc ctcaaacgaa agcatcaact aaatccgcaa    2040
cgagcagtga agtggtagtt gagttttaa aagagttggc aaaaaaagga agcaaggaag    2100
ataacgagca gaatttagaa aaaactgacc gcacttctac ggacttgaca gaaagtgcgg    2160
tagaaaattc ggctgctttg agtttaccca gctttcttgt acaaagtggt tgatatcgca    2220
tgcggtaccg gcggaatggt gagcaagggc gaggagctgt tcaccggggt ggtgcccatc    2280
ctggtcgagc tggacggcga cgtaaacggc cacaagttca gcgtgtccgg cgagggcgag    2340
```

```
ggcgatgcca cctacggcaa gctgaccctg aagttcatct gcaccaccgg caagctgccc    2400
gtgccctggc ccaccctcgt gaccaccctg acctacggcg tgcagtgctt cagccgctac    2460
cccgaccaca tgaagcagca cgacttcttc aagtccgcca tgcccgaagg ctacgtccag    2520
gagcgcacca tcttcttcaa ggacgacggc aactacaaga cccgcgccga ggtgaagttc    2580
gagggcgaca ccctggtgaa ccgcatcgag ctgaagggca tcgacttcaa ggaggacggc    2640
aacatcctgg ggcacaagct ggagtacaac tacaacagcc acaacgtcta tatcatggcc    2700
gacaagcaga agaacggcat caaggtgaac ttcaagatcc gccacaacat cgaggacggc    2760
agcgtgcagc tcgccgacca ctaccagcag aacaccccca tcggcgacgg ccccgtgctg    2820
ctgcccgaca ccactacct gagcacccag tccgccctga gcaaagaccc caacgagaag    2880
cgcgatcaca tggtcctgct ggagttcgtg accgccgccg ggatcactct cggcatggac    2940
gagctgtaca agtaagcggc cgcatactgg attggtgaat caatgagccg tagcacaatg    3000
gttacattcg gctagctaag atccaatggc aaggaccaag tgctggaact tgttttgctt    3060
tagcagatct tagcgtgaga ggtatttgtc ctctgtcagg agtagatagt agatgttctt    3120
tttaaactaa aatgctaact gttccgaatt cctcatcgca gctaatccgt acatcaaaag    3180
acaaaatgct aggtatgtgt actacatctc ctgttgctag ataagacata tgataggaaa    3240
cacaccatca atagtcattg tagctttact tatactacgc atttgcactt tcccctgagt    3300
ggcagaggcg cattgagaaa atcgatctca acatagttta tgtagcatcc cctagatcca    3360
ttactttaag tctccttcgt ctttggtgta ggcatgttgg acacaacgag gtaaaacaca    3420
acacaaacaa tgtgtccagc aaagtagtag ctgctccagt tctcccgggg gatccactag    3480
ttctagagcg gccggccgcc accgcggtgg agctccagct tttgttccct ttagtgaggg    3540
ttaattgcgc gcttggcgta atcatggtca tagctgtttc ctgtgtgaaa ttgttatccg    3600
ctcacaattc cacacaacat acgagccgga agcataaagt gtaaagcctg ggtgcctaa    3660 tgagtgagct aactcacatt aattgcgttg cgctcactgc ccgctttcca gtcgggaaac    3720
ctgtcgtgcc agctgcatta atgaatcggc caacgcgcgg ggagaggcgg tttgcgtatt    3780
gggcgctctt ccgcttcctc gctcactgac tcgctgcgct cggtcgttcg gctgcggcga    3840
gcggtatcag ctcactcaaa ggcggtaata cggttatcca cagaatcagg ggataacgca    3900
ggaaagaaca tgtgagcaaa aggccagcaa aaggccagga accgtaaaaa ggccgcgttg    3960
ctggcgtttt tccataggct ccgcccccct gacgagcatc acaaaaatcg acgctcaagt    4020
cagaggtggc gaaacccgac aggactataa agataccagg cgtttccccc tggaagctcc    4080
ctcgtgcgct ctcctgttcc gaccctgccg cttaccggat acctgtccgc ctttctccct    4140
tcgggaagcg tggcgctttc tcatagctca cgctgtaggt atctcagttc ggtgtaggtc    4200
gttcgctcca agctgggctg tgtgcacgaa ccccccgttc agcccgaccg ctgcgcctta    4260
tccggtaact atcgtcttga gtccaacccg gtaagacacg acttatcgcc actggcagca    4320
gccactggta acaggattag cagagcgagg tatgtaggcg gtgctacaga gttcttgaag    4380
tggtggccta actacggcta cactagaagg acagtatttg gtatctgcgc tctgctgaag    4440
ccagttacct tcggaaaaag agttggtagc tcttgatccg gcaaacaaac caccgctggt    4500
agcggtggtt ttttgtttg caagcagcag attacgcgca gaaaaaaagg atctcaagaa    4560
gatcctttga tcttttctac ggggtctgac gctcagtgga acgaaaactc acgttaaggg    4620
attttggtca tgagattatc aaaaaggatc ttcacctaga tccttttaaa ttaaaaatga    4680
```

| | |
|---|---|
| agttttaaat caatctaaag tatatatgag taaacttggt ctgacagtta ccaatgctta | 4740 |
| atcagtgagg cacctatctc agcgatctgt ctatttcgtt catccatagt tgcctgactc | 4800 |
| cccgtcgtgt agataactac gatacgggag ggcttaccat ctggcccag tgctgcaatg | 4860 |
| ataccgcgag acccacgctc accggctcca gatttatcag caataaacca gccagccgga | 4920 |
| agggccgagc gcagaagtgg tcctgcaact ttatccgcct ccatccagtc tattaattgt | 4980 |
| tgccgggaag ctagagtaag tagttcgcca gttaatagtt tgcgcaacgt tgttgccatt | 5040 |
| gctacaggca tcgtggtgtc acgctcgtcg tttggtatgg cttcattcag ctccggttcc | 5100 |
| caacgatcaa ggcgagttac atgatccccc atgttgtgca aaaaagcggt tagctccttc | 5160 |
| ggtcctccga tcgttgtcag aagtaagttg gccgcagtgt tatcactcat ggttatggca | 5220 |
| gcactgcata attctcttac tgtcatgcca tccgtaagat gcttttctgt gactggtgag | 5280 |
| tactcaacca agtcattctg agaatagtgt atgcggcgac cgagttgctc ttgcccggcg | 5340 |
| tcaatacggg ataataccgc gccacatagc agaactttaa aagtgctcat cattggaaaa | 5400 |
| cgttcttcgg ggcgaaaact ctcaaggatc ttaccgctgt tgagatccag ttcgatgtaa | 5460 |
| cccactcgtg cacccaactg atcttcagca tcttttactt tcaccagcgt ttctgggtga | 5520 |
| gcaaaaacag gaaggcaaaa tgccgcaaaa aagggaataa gggcgacacg gaaatgttga | 5580 |
| atactcatac tcttcctttt tcaatattat tgaagcattt atcagggtta ttgtctcatg | 5640 |
| agcggataca tatttgaatg tatttagaaa aataaacaaa taggggttcc gcgcacattt | 5700 |
| ccccgaaaag tgccacctaa attgtaagcg ttaatatttt gttaaaattc gcgttaaatt | 5760 |
| tttgttaaat cagctcattt tttaaccaat aggccgaaat cggcaaaatc ccttataaat | 5820 |
| caaaagaata accgagata gggttgagtg ttgttccagt ttggaacaag agtccactat | 5880 |
| taaagaacgt ggactccaac gtcaaagggc gaaaaaccgt ctatcagggc gatggcccac | 5940 |
| tacgtgaacc atcaccctaa tcaagttttt tggggtcgag gtgccgtaaa gcactaaatc | 6000 |
| ggaaccctaa agggagcccc cgatttagag cttgacgggg aaagccggcg aacgtggcga | 6060 |
| gaaaggaagg gaagaaagcg aaaggagcgg gcgctagggc gctggcaagt gtagcggtca | 6120 |
| cgctgcgcgt aaccaccaca cccgccgcgc ttaatgcgcc gctacagggc gcgtcccatt | 6180 |
| cgccattcag gctgcgcaac tgttgggaag ggcgatcggt gcgggcctct tcgctattac | 6240 |
| gccagctggc gaaagggggga tgtgctgcaa ggcgattaag ttgggtaacg ccagggtttt | 6300 |
| cccagtcacg acgttgtaaa acgacggcca gtgagcgcgc gtaatacgac tcactatagg | 6360 |
| gcgaattggg tacgtaccgg gccccccctc gaggtcgacg gtatcgata | 6409 |

<210> SEQ ID NO 10
<211> LENGTH: 6408
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

| | |
|---|---|
| agcttgcgct ttttccgaga actccccata agtcaacggc tccaatcaag aatgtatccg | 60 |
| acaacggcga gcatagcaac acgtccgtct ttggagtaga atcatcatgt tgtggatgaa | 120 |
| tacacagatg aatgacatta aaagcatgaa catgttagag agtaggaggt agagattgat | 180 |
| atggtagcat tgcgatgttt gttttttggtc agcatatgat gagtggatac caatatgatg | 240 |
| aaagttgaat ctcgcgtttg agctcagcgg tacgttattg atcgaaagta gcctgatcaa | 300 |

```
aatccttgga gagtacaaga ggatcaaaga atccagtggg ggcgataact ccaagctcgt    360
tctcaaagag gcaatggagg tagaaactca tcccagttga gaagaagtga aggcagtggc    420
ggtggcgaaa gcagaggcaa cgaggacaga cttcctgtgg gttgatgcaa cgaatatttc    480
cagaaggaga agtttagaga gttgaaccgc tacctacaat gacaaagtat cgtatcgatt    540
ttgatgttgg ttggttatga attcaaactg taagttggat tgtgagaaga tcagaagttg    600
aacgaacaca tctttccgat cattcacctc cacactgcaa caacacggta cttcttccgc    660
ggcaggtctc tgtcgccatt ctcttgtcct gttgttggct gtgagacgag gaaagcaacg    720
acaagtttca caaagggag ttcctttaac gagatatgtt ttttataaag gtcccaata    780 gaaagacaaa ttgattcctc cgtgcaaacg cgcaaataaa caccacgtcc attatatcca    840
tatctttcag agtatccaac aagtgttgaa ggacaggtag ttgaagtaac gtatcttccc    900
cctcgactgg atccatcaac aaggcgaaca aatccattca acctctcata aattatctga    960
tttaccaaac cgatatcaac aagtttgtac aaaaaagcat gtctgtgaac gaggtggctc   1020
cactctcttc tgtgccagct gagctcaagg atgctgctgg aggaaacaag aaggctgctg   1080
agaagtctga gggagctacc ggagtggaga aggagaagac caccctcttc caacgtgtga   1140
agcaattctt caccggatct aagtctggag ctaagccagt ggctggagat gagaccgcta   1200
acaaggtgaa ctaccaagat ctcgaggata acctcaacct caagggactc atctctctcg   1260
aggatgatcg taacgctaac ttcgagtcta acgtgctcaa gaacgagaag ttcctcgatg   1320
aggctcgtga gatctctaag aagtctatcc cagaggctac cgtgaagcaa atgtctcacc   1380
tcccagagtt cgatgatatc ctcaccgagg gagctaagaa ggtggagtct cgtatcaaca   1440
aggctatcac cttccgtcca tctgtggagg agttctctga gatccaagat ctcgtgaaga   1500
ccctcccaaa gaccaaggtg atcgaggatc tctctaccaa gaccaacgag atcaccgagg   1560
ctctcgctgc tacctctaag accatccaac gtaccccaga gctcaaggag caactcaaga   1620
ccgctatcga ggatttcctc caaaactctc aaggaaagcc actcaccgtg caaatgatcg   1680
agaacctcaa ccacggactc cgtccagatg agggagaggg acgtctcctc tacaagaagg   1740
agaacctcac caaggagaac gctgtgttct cttctccaga ggctgctaag atccaactcg   1800
ctgagaccgt ggatttcatc aaccgtgcta agaacgaggg aatcgagcca tctgtggtgg   1860
gagctctcgt gtaccaacgt ctcatcgctt accaccatt cgctgaggga acggacgta   1920 tggctcgtgt gatcgtgaac aagatcctcc tcgatgctgg ataccccagct ttcaccaagt   1980 tctctgatga gttcgagcca caaatcatcc cacaaaccaa ggcttctacc aagtctgcta   2040
cctcttctga ggtggtggtg gagttcctca aggagctcgc taagaaggga tctaaggagg   2100
ataacgagca aaacctcgag aagaccgatc gtacctctac cgatctcacc gagtctgctg   2160
tggagaactc tgctgctctc tcttacccag ctttcttgta caaagtggtt gatatcgcat   2220
gcggtaccgg cggaatggtg agcaagggcg aggagctgtt caccggggtg gtgcccatcc   2280
tggtcgagct ggacggcgac gtaaacggcc acaagttcag cgtgtccggc gagggcgagg   2340
gcgatgccac ctacggcaag ctgaccctga agttcatctg caccaccggc aagctgcccg   2400
tgccctggcc caccctcgtg accaccctga cctacggcgt gcagtgcttc agccgctacc   2460
ccgaccacat gaagcagcac gacttcttca gtccgccat gcccgaaggc tacgtccagg   2520
agcgcaccat cttcttcaag gacgacggca actacaagac ccgcgccgag gtgaagttcg   2580
agggcgacac cctggtgaac cgcatcgagc tgaagggcat cgacttcaag gaggacggca   2640
acatcctggg gcacaagctg gagtacaact acaacagcca caacgtctat atcatggccg   2700
```

```
acaagcagaa gaacggcatc aaggtgaact tcaagatccg ccacaacatc gaggacggca    2760
gcgtgcagct cgccgaccac taccagcaga acacccccat cggcgacggc cccgtgctgc    2820
tgcccgacaa ccactacctg agcacccagt ccgccctgag caaagacccc aacgagaagc    2880
gcgatcacat ggtcctgctg gagttcgtga ccgccgccgg gatcactctc ggcatggacg    2940
agctgtacaa gtaagcggcc gcatactgga ttggtgaatc aatgagccgt agcacaatgg    3000
ttacattcgg ctagctaaga tccaatggca aggaccaagt gctggaactt gttttgcttt    3060
agcagatctt agcgtgagag gtatttgtcc tctgtcagga gtagatagta gatgttcttt    3120
ttaaactaaa atgctaactg ttccgaattc ctcatcgcag ctaatccgta catcaaaaga    3180
caaaatgcta ggtatgtgta ctacatctcc tgttgctaga taagacatat gataggaaac    3240
acaccatcaa tagtcattgt agctttactt atactacgca tttgcacttt ccctgagtg     3300
gcagaggcgc attgagaaaa tcgatctcaa catagtttat gtagcatccc ctagatccat    3360
tactttaagt ctccttcgtc tttggtgtag gcatgttgga cacaacgagg taaaacacaa    3420
cacaaacaat gtgtccagca aagtagtagc tgctccagtt ctcccggggg atccactagt    3480
tctagagcgg ccgccgcca ccgcggtgga gctccagctt ttgttcccct tagtgagggt     3540
taattgcgcg cttggcgtaa tcatggtcat agctgtttcc tgtgtgaaat tgttatccgc    3600
tcacaattcc acacaacata cgagccgaaa gcataaagtg taaagcctgg ggtgcctaat    3660
gagtgagcta actcacatta attgcgttgc gctcactgcc cgctttccag tcgggaaacc    3720
tgtcgtgcca gctgcattaa tgaatcggcc aacgcgcggg gagaggcggt ttgcgtattg    3780
ggcgctcttc cgcttcctcg ctcactgact cgctgcgctc ggtcgttcgg ctgcggcgag    3840
cggtatcagc tcactcaaag gcggtaatac ggttatccac agaatcaggg gataacgcag    3900
gaaagaacat gtgagcaaaa ggccagcaaa aggccaggaa ccgtaaaaag gccgcgttgc    3960
tggcgttttt ccataggctc cgcccccctg acgagcatca caaaaatcga cgctcaagtc    4020
agaggtggcg aaacccgaca ggactataaa gataccaggc gtttccccct ggaagctccc    4080
tcgtgcgctc tcctgttccg accctgccgc ttaccggata cctgtccgcc tttctccctt    4140
cgggaagcgt ggcgctttct catagctcac gctgtaggta tctcagttcg gtgtaggtcg    4200
ttcgctccaa gctgggctgt gtgcacgaac cccccgttca gcccgaccgc tgcgccttat    4260
ccggtaacta tcgtcttgag tccaacccgg taagacacga cttatcgcca ctggcagcag    4320
ccactggtaa caggattagc agagcgaggt atgtaggcgg tgctacagag ttcttgaagt    4380
ggtggcctaa ctacggctac actagaagga cagtatttgg tatctgcgct ctgctgaagc    4440
cagttacctt cggaaaaaga gttggtagct cttgatccgg caaacaaacc accgctggta    4500
gcggtggttt ttttgtttgc aagcagcaga ttacgcgcag aaaaaaagga tctcaagaag    4560
atcctttgat cttttctacg gggtctgacg ctcagtggaa cgaaaactca cgttaaggga    4620
ttttggtcat gagattatca aaaaggatct tcacctagat cctttaaat taaaaatgaa     4680
gttttaaatc aatctaaagt atatatgagt aaacttggtc tgacagttac caatgcttaa    4740
tcagtgaggc acctatctca gcgatctgtc tatttcgttc atccatagtt gcctgactcc    4800
ccgtcgtgta gataactacg atacgggagg gcttaccatc tggccccagt gctgcaatga    4860
taccgcgaga cccacgctca ccggctccag atttatcagc aataaaccag ccagccggaa    4920
gggccgagcg cagaagtggt cctgcaactt tatccgcctc catccagtct attaattgtt    4980
gccgggaagc tagagtaagt agttcgccag ttaatagttt cgcaacgtt gttgccattg     5040
```

-continued

| | |
|---|---|
| ctacaggcat cgtggtgtca cgctcgtcgt ttggtatggc ttcattcagc tccggttccc | 5100 |
| aacgatcaag gcgagttaca tgatccccca tgttgtgcaa aaaagcggtt agctccttcg | 5160 |
| gtcctccgat cgttgtcaga agtaagttgg ccgcagtgtt atcactcatg gttatggcag | 5220 |
| cactgcataa ttctcttact gtcatgccat ccgtaagatg cttttctgtg actggtgagt | 5280 |
| actcaaccaa gtcattctga gaatagtgta tgcggcgacc gagttgctct tgcccggcgt | 5340 |
| caatacggga taataccgcg ccacatagca gaactttaaa agtgctcatc attggaaaac | 5400 |
| gttcttcggg gcgaaaactc tcaaggatct taccgctgtt gagatccagt tcgatgtaac | 5460 |
| ccactcgtgc acccaactga tcttcagcat cttttacttt caccagcgtt tctgggtgag | 5520 |
| caaaaacagg aaggcaaaat gccgcaaaaa agggaataag ggcgacacgg aaatgttgaa | 5580 |
| tactcatact cttccttttt caatattatt gaagcattta tcagggttat tgtctcatga | 5640 |
| gcggatacat atttgaatgt atttagaaaa ataaacaaat aggggttccg cgcacatttc | 5700 |
| cccgaaaagt gccacctaaa ttgtaagcgt taatattttg ttaaaattcg cgttaaattt | 5760 |
| ttgttaaatc agctcatttt ttaaccaata ggccgaaatc ggcaaaatcc cttataaatc | 5820 |
| aaaagaatag accgagatag ggttgagtgt tgttccagtt tggaacaaga gtccactatt | 5880 |
| aaagaacgtg gactccaacg tcaaagggcg aaaaaccgtc tatcagggcg atggcccact | 5940 |
| acgtgaacca tcaccctaat caagttttt ggggtcgagg tgccgtaaag cactaaatcg | 6000 |
| gaaccctaaa gggagccccc gatttagagc ttgacgggga agccggcga acgtggcgag | 6060 |
| aaaggaaggg aagaaagcga aaggagcggg cgctagggcg ctggcaagtg tagcggtcac | 6120 |
| gctgcgcgta accaccacac ccgccgcgct taatgcgccg ctacagggcg cgtcccattc | 6180 |
| gccattcagg ctgcgcaact gttgggaagg gcgatcggtg cgggcctctt cgctattacg | 6240 |
| ccagctggcg aaagggggat gtgctgcaag gcgattaagt tgggtaacgc cagggttttc | 6300 |
| ccagtcacga cgttgtaaaa cgacggccag tgagcgcgcg taatacgact cactataggg | 6360 |
| cgaattgggt acgtaccggg cccccctcg aggtcgacgg tatcgata | 6408 |

<210> SEQ ID NO 11
<211> LENGTH: 121
<212> TYPE: PRT
<213> ORGANISM: White spot syndrome virus

<400> SEQUENCE: 11

Met Ala Thr Thr Thr Asn Thr Leu Pro Phe Gly Arg Thr Gly Ala Gln
1               5                   10                  15

Ala Ala Gly Pro Ser Tyr Thr Met Glu Asp Leu Glu Gly Ser Met Ser
            20                  25                  30

Met Ala Arg Met Gly Leu Phe Leu Ile Val Ala Ile Ser Ile Gly Ile
        35                  40                  45

Leu Val Leu Ala Val Met Asn Val Trp Met Gly Pro Lys Lys Asp Ser
    50                  55                  60

Asp Ser Asp Thr Asp Lys Asp Thr Val Asp Asp Asp Thr Ala Asn
65                  70                  75                  80

Asp Asn Asp Asp Glu Asp Lys Tyr Lys Asn Arg Thr Arg Asp Met Met
                85                  90                  95

Leu Leu Ala Gly Ser Ala Leu Leu Phe Leu Val Ser Ala Ala Thr Val
                100                 105                 110

Phe Met Ser Tyr Pro Lys Arg Arg Gln
            115                 120

<210> SEQ ID NO 12
<211> LENGTH: 363
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 12
atggctacta ctactaatac acttcctttt ggacgtaccg gagctcaagc cgcaggaccc 60
tcgtacacga tggaagatct cgaaggaagt atgagtatgg ctcgcatggg attgttcctc 120
attgttgcca tttctatcgg aattctcgtc cttgcagtca tgaatgtctg gatgggaccg 180
aagaaggatt cggacagtga caccgataag gatactgtgg atgatgatga cacggcgaac 240
gataatgatg acgaggacaa gtacaagaat cgtacccgtg acatgatgct tttggctgga 300
tcagccctct tgtttttggt gtctgcggca actgtcttca tgagctaccc caagaggcga 360
cag 363

<210> SEQ ID NO 13
<211> LENGTH: 466
<212> TYPE: PRT
<213> ORGANISM: White spot syndrome virus

<400> SEQUENCE: 13

Met Ser Ala Ser Leu Ile Leu Asp Glu Tyr Leu Lys Lys Thr Ala Ser
1 5 10 15

Ala Val Leu Asp Val Ala Asp Ser Phe Glu Lys Ile Lys Gly Glu Ile
20 25 30

Gln Ser Pro Glu Glu Ala Ala Ala Leu Ser Val Ala Leu Tyr Gly Ala
35 40 45

Pro Pro Lys Pro Ser Ala Ser Ala Val Ala Ser Ile Ile Thr Gly Glu
50 55 60

Arg Thr Ser Leu Asn Asp Lys Tyr Leu Ser Asp Asn Val Leu Leu Lys
65 70 75 80

Met Ser Val Ala Arg Val Gly Gln Glu Asn Asn Arg Lys Arg Ala Asp
85 90 95

Gln Ala Ala Asp Glu Ile Arg Thr Ile Met Glu Asp Ile Thr Gly Ser
100 105 110

Leu Ser Gly Ala Tyr Arg Gln Tyr Ser Pro Leu Glu Glu Glu Asn Lys
115 120 125

Val His Ile Gly Ile Met Asn Asn Lys Thr Pro Ser Ile Val Cys Gly
130 135 140

Tyr Tyr Thr Met Asp Thr Ser Ile Ser Ser Glu Pro Leu Ser Leu Thr
145 150 155 160

Asp Phe Gln Asn Pro Thr Val Ile Ala Asn Val Thr Lys Arg Met Glu
165 170 175

Ser Ile Phe Ser Lys Val Asp Ser Ala Arg Ser Thr Arg Phe Asp Ala
180 185 190

Phe Val Asn Gly Val Ala Asn Asn Met Asp Ile Lys Ser Ser Ile Asp
195 200 205

Trp Ala Asn Met Val Glu Asn Val Ile Lys Leu Pro Asp Ser Thr Pro
210 215 220

Asn Pro Cys Ser Val Asp Thr Ile Val Ser Arg Asp Ala Ser Val Val
225 230 235 240

Lys Thr Ala Val Asn Asp Ile Tyr Ala Ser Val Gly Lys Ser Tyr Cys
245 250 255

Arg Pro Ala Thr Gln Leu Thr Phe Met Ser Glu Ile Glu Lys Leu Arg
                260                 265                 270

Lys Ala Ala Val Val Cys Phe Glu Ala Leu Met Ser Asp Thr Arg Glu
            275                 280                 285

Arg Ala Phe Val Glu Phe Leu Phe Tyr Val Ser Phe Lys Glu Asp Ala
        290                 295                 300

Ser Asn Thr Asn Ser Lys Leu Phe Val Gln Asn Lys Leu Ser Ser Met
305                 310                 315                 320

Ser Gly Asn Pro Arg Gln Pro Ile Lys Leu Val Arg Arg Ser Ala Glu
                325                 330                 335

Glu Thr Leu Phe Gly Leu Cys Phe Met Phe Lys Val Met Pro Pro Glu
            340                 345                 350

Phe Met Asn Cys Ile Phe Asn Phe Pro Thr Ile Pro His Ser Thr Gln
        355                 360                 365

Tyr His Gly Leu Tyr Gly Thr Cys Leu Thr Pro Leu Leu Arg Lys Tyr
    370                 375                 380

Gly Ser Ser Phe Glu Lys Ser Trp Ala His Phe Glu Glu Ile Leu Ser
385                 390                 395                 400

Glu Arg Ala Asn Ala Val Lys Lys Phe Gly Val Asn Asp Thr Arg Ile
                405                 410                 415

Asp Cys Leu Asp Ala Val Ala Asn Leu Thr Gly Pro Val Tyr Val Leu
            420                 425                 430

Ile Leu Asp Leu Val Arg Thr Leu Ser Ala Gln Arg Ser Cys Ser Thr
        435                 440                 445

Lys Phe Leu Arg Glu Ile Lys Glu Asn Tyr Leu Leu Trp Asn Arg Phe
    450                 455                 460

Val Ser
465

<210> SEQ ID NO 14
<211> LENGTH: 1398
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
atgtccgctt ccttgatcct cgatgaatac ttgaaaaaga cggcttctgc cgtgttggat      60
gtcgcagata gttttgagaa gattaaggga gaaattcaga gtcctgagga ggctgcagct     120
ctcagtgtag cccttatgg cgcaccgcct aaacctagcg catcggcagt tgcctccatt     180
attactggag agcgcacgtc tttgaatgat aagtacctca gtgataacgt tttgctcaag     240
atgtctgtgg cccgtgtggg gcaggagaac aaccgcaaga gggcagatca agccgcagat     300
gaaatccgta ctattatgga ggacattact ggatctttga gtggtgccta tagacaatac     360
tctccattgg aggaggaaaa caaggttcat atcggaatta tgaacaataa gacgccaagc     420
atcgtatgtg atattatac catggatacc tcaattagta gtgagccttt gtccctcacc     480
gacttccaga accctacagt gatcgcaaac gtaacgaagc gtatggaatc gatcttcagc     540
aaggtcgatt cagcccgctc cacgcgtttc gatgcattcg tcaacggtgt tgcaaataac     600
atggacatta gtcgagtat cgactgggcg aacatggtcg agaatgttat taagttgcct     660
gattcaacgc caaccccttg ctctgtggat acaattgtct cgcgtgacgc gagcgtcgtc     720
aaaacggcag tcaatgatat ctacgcttcc gttggaaaat cctactgcag gccagctacg     780

```
cagttgacat tcatgtctga aatcgagaaa ctccgtaagg cggcggtggt gtgtttcgag    840
gctctcatgt ctgatacaag ggagagagcc ttcgtggagt tccttttcta tgtgagcttc    900
aaggaggatg cttcgaatac taactctaag ctcttcgtgc agaacaagct ctcaagtatg    960 tctgaaacc ccaggcaacc catcaaattg gtacgacgta gcgccgagga aactcttttc   1020
ggtttgtgtt tcatgtttaa agtaatgcct cccgaattca tgaactgtat cttcaatttt   1080
cctacgatcc cacacagcac tcagtaccac ggtttgtatg gtacctgtct cacgcctttg   1140
ctccgtaaat acggttcgtc ctttgaaaag tcgtgggccc acttcgaaga gattctttct   1200
gagcgtgcca atgccgttaa gaagtttggc gtcaacgaca cccgtatcga ctgccttgac   1260
gctgtagcaa atctcactgg accagtttat gttttgattc tcgatcttgt tcgtactctc   1320
tctgcccaac gtagctgtag cactaagttc ttgcgagaaa ttaaagagaa ctatctcctt   1380
tggaacagat tcgtttct                                                  1398
```

<210> SEQ ID NO 15
<211> LENGTH: 195
<212> TYPE: PRT
<213> ORGANISM: Vibrio harveyi

<400> SEQUENCE: 15

```
Met Lys Arg Arg Asn Pro Gln Gly Leu Thr Leu Leu Glu Leu Ile Ile
1               5                   10                  15

Ala Ile Val Ile Leu Gly Ile Leu Ala Val Val Ala Ala Pro Arg Phe
            20                  25                  30

Leu Asn Leu Gln Asp Asp Ala Tyr Gln Ala Lys Met Glu Ser Ile Ala
        35                  40                  45

Asp Gln Phe Glu Thr Gly Val Arg Phe Thr Gln Ser Gln Trp Leu Val
    50                  55                  60

Asn Gly Gly Thr Gln Glu Ala Gln Thr Asp Ile Asp Gly Tyr Gly Gly
65                  70                  75                  80

Gly Glu Leu Asp Val Asn Glu Phe Gly Phe Pro Leu Gly Thr Asn Lys
                85                  90                  95

Gly Asn Arg Asn Gly Val Ile Gly Asn Pro Tyr Asn Ile Gly Gln Gly
            100                 105                 110

Asn Ala Gly Cys Ile Ala Val Trp Gln Ala Leu Leu Gly Asn Glu Tyr
        115                 120                 125

Ser Leu Ser Asn Asn Arg Asn Ala Asn Asp Arg Phe Asp Phe Ile Thr
    130                 135                 140

Arg Arg Val Gln Asp Lys Glu Ser His Gln Ser Val Cys Tyr Tyr Thr
145                 150                 155                 160

Phe Thr Lys Lys Gly Tyr Asp Arg Asn Pro Asp Asn Ser Ser Phe Val
                165                 170                 175

Ile Trp Tyr Asp Ser Lys Thr Gly Ser Val Thr Thr Ser Lys Pro Thr
            180                 185                 190

Arg Leu Lys
        195
```

<210> SEQ ID NO 16
<211> LENGTH: 585
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
atgaaaagac gtaaccccca gggattgacc ttgttggaat tgatcattgc tattgtaatc      60
ttgggaatcc tcgctgttgt ggccgcgcct aggttcctca acctccagga cgatgcgtat     120
caagcaaaaa tggagtcaat tgcggaccaa tttgagacag gagtcaggtt cacacagtct     180
caatggctcg taaacggagg cactcaagag gcccagacgg acattgacgg atatggaggt     240
ggagaattgg atgtaaatga gtttgggttc ccgttgggaa ccataagggg aacagaaat      300
ggtgttattg aaacccata caacatcggc caaggcaatg cgggatgcat tgcagtgtgg     360
caagcccttc tcgggaacga gtactctctt tccaataata gaaatgcgaa cgatcgcttc     420
gacttcatta cgcgtcgtgt gcaggacaaa gaatcgcacc agtctgtgtg ttattatacc     480
tttactaaaa agggatacga tcgtaatccc gacaattcat ccttcgtcat ctggtacgac     540
tccaagactg gttcagtgac tacgtccaag cctactagac tcaag                     585
```

<210> SEQ ID NO 17
<211> LENGTH: 455
<212> TYPE: PRT
<213> ORGANISM: Vibrio harveyi

<400> SEQUENCE: 17

```
Met Lys Lys Pro Leu Leu Ala Leu Thr Val Leu Ser Leu Ser Leu Gly
1               5                   10                  15

Ser Ile Ile Thr Pro Val Thr Ala Ala Leu Pro Leu Ser Val
            20                  25                  30

Asp Gly Glu Gln Leu Pro Ser Leu Ala Pro Met Leu Glu Lys Val Thr
        35                  40                  45

Pro Ala Val Val Ser Ile Ala Val Glu Gly Lys Gln Val Gln Thr Ser
    50                  55                  60

Arg Ile Pro Glu Gln Phe Gln Phe Phe Gly Pro Asp Phe Pro Thr
65                  70                  75                  80

Glu Gln Thr Arg Glu Arg Pro Phe Arg Gly Leu Gly Ser Gly Val Ile
                85                  90                  95

Ile Asp Ala Lys Lys Gly Arg Ile Val Thr Asn Tyr His Val Ile Lys
            100                 105                 110

Gly Ala Asp Asp Ile Arg Val Arg Leu Tyr Asp Gly Arg Glu Tyr Asp
        115                 120                 125

Ala Glu Leu Val Gly Gly Asp Glu Met Ser Asp Ile Ala Leu Leu Lys
    130                 135                 140

Leu Glu Lys Ala Lys Asp Leu Thr Gln Ile Lys Val Ala Asp Ser Asp
145                 150                 155                 160

Lys Leu Arg Val Gly Asp Phe Thr Val Ala Ile Gly Asn Pro Phe Gly
                165                 170                 175

Leu Gly Gln Thr Val Thr Ser Gly Ile Val Ser Ala Leu Gly Arg Ser
            180                 185                 190

Gly Leu Asn Val Glu Asn Phe Glu Asn Phe Ile Gln Thr Asp Ala Ala
        195                 200                 205

Ile Asn Ser Gly Asn Ser Gly Gly Ala Leu Val Asn Leu Asn Gly Glu
    210                 215                 220

Leu Ile Gly Ile Asn Thr Ala Ile Leu Gly Pro Asn Gly Gly Asn Val
225                 230                 235                 240

Gly Ile Gly Phe Ala Ile Pro Ser Asn Met Met Lys Asn Leu Thr Asp
                245                 250                 255

Gln Ile Leu Glu Phe Gly Glu Val Lys Arg Gly Met Leu Gly Val Gln
```

```
            260                 265                 270
Gly Gly Glu Val Thr Ser Glu Leu Ala Glu Ala Leu Gly Tyr Glu Ser
                275                 280                 285

Ser Lys Gly Ala Phe Val Ser Gln Val Val Pro Asp Ser Ala Ala Asp
            290                 295                 300

Lys Ala Gly Leu Lys Ala Gly Asp Val Ile Val Ser Ile Asn Gly Lys
305                 310                 315                 320

Ala Ile Asp Thr Phe Ala Glu Leu Arg Ala Lys Val Ala Thr Leu Gly
                325                 330                 335

Ala Gly Lys Lys Val Thr Leu Gly Val Val Arg Asp Gly Lys Lys Lys
                340                 345                 350

Ser Phe Asp Val Thr Leu Gly Glu Ser Thr Asn Val Lys Ala Lys Ala
                355                 360                 365

Glu Thr Leu His Glu Gly Leu Lys Gly Ala Glu Leu Ser Asn Thr Thr
                370                 375                 380

Pro Ser Asp Ser Ile Gln Gly Val Lys Val Thr Ser Val Ala Glu Asn
385                 390                 395                 400

Ser Pro Ala Ala Gln Tyr Gln Leu Ala Glu Gly Asp Ile Ile Ile Gly
                405                 410                 415

Val Asn Arg Lys Arg Val Lys Asn Leu Ala Glu Leu Arg Ala Ile Val
                420                 425                 430

Glu Lys His Gln Gly Val Leu Ala Ile Asn Val Gln Arg Gly Asp Arg
                435                 440                 445

Thr Val Tyr Leu Val Ile Arg
            450                 455

<210> SEQ ID NO 18
<211> LENGTH: 1365
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
atgaagaagc ctttgttggc attgaccgta ttgtccttgt ctttgggatc tatcatcaca      60
ccggtcaccg caacagcggc tttgcctctt tctgttgatg gtgagcaact cccaagtttg     120
gcccctatgc tcgagaaggt gacaccagct gtggtgagta tcgcggtaga gggtaagcaa     180
gtgcaaacct caagaattcc agaacagttc caattttttct tcgggcctga tttcccgact     240
gaacaaaccc gagaacgtcc attccgtggt cttggctcgg gtaatcat tgacgctaag      300 aaaggtcgta tcgttacgaa ctaccatgtt atcaagggag cagacgatat tagagtacgt     360
ttgtatgacg gtagagaata tgatgcagag ctcgttggtg gtgacgagat gtcggatatc     420
gctctcttga agctcgaaaa ggccaaggac ttgacacaga tcaaggtagc tgactccgac     480
aagttgaggg ttggagattt cacggtggca atcggcaacc cctttggact cggacaaact     540
gttacatctg gaattgtcag cgccctcggt agatcgggct gaatgtaga gaacttcgag     600 aacttcatcc aaactgatgc tgcaattaat tctggcaact ctggcggagc tttggtgaac     660
ttgaacggag agcttattgg aattaatact gctatcttgg accgaatgg tgggaacgtg     720 ggaattggat ttgctatccc cagtaatatg atgaaaaatc tcacggatca gatcttggag     780
tttggtgagg ttaagagagg catgctcggc gtccagggcg gcgaagttac aagtgagctt     840
gctgaagccc tcggttacga gagttccaag ggagctttcg tttctcaagt cgtgcccgac     900
```

-continued

```
agtgcagcag ataaggctgg tttgaaggct ggagatgtta tcgtcagcat taacggaaag      960
gccatcgata cgttcgcaga gcttcgcgct aaggttgcta cgcttggagc tggcaagaaa     1020
gtgacactcg gagtagttag ggacggaaag aagaagtctt tcgatgtcac gctcggcgag     1080
agcactaatg tgaaagccaa ggcggagacc ctccacgaag gactcaaggg cgccgaattg     1140
tcaaacacaa ctccctctga ttcgatccaa ggagtcaagg taacctcggt tgcagagaac     1200
tccccagcgg cgcaatatca gttggctgaa ggagacatca tcatcggagt gaacagaaaa     1260
cgagtgaaga accttgctga gttgagagct atcgtcgaaa agcatcaagg agttcttgcc     1320
atcaacgtgc agagaggaga tcgaactgtc tacctcgtca ttagg                    1365
```

<210> SEQ ID NO 19
<211> LENGTH: 418
<212> TYPE: PRT
<213> ORGANISM: Vibrio harveyi

<400> SEQUENCE: 19

```
Met Asn Lys Thr Ile Thr Leu Leu Ser Ala Leu Leu Pro Leu Ser
1               5                   10                  15

Phe Ala His Ala Ala Glu Pro Thr Leu Ser Pro Glu Met Val Ser Ala
            20                  25                  30

Ser Gln Val Arg Ser Ala Gln Ala Lys Gln Thr Tyr Thr Tyr Val Arg
        35                  40                  45

Cys Trp Tyr Arg Thr Ser Tyr Ser Lys Asp Glu Pro Ala Thr Asp Trp
    50                  55                  60

Glu Trp Ala Glu Asn Pro Asp Gly Ser Tyr Phe Thr Leu Asp Gly Tyr
65                  70                  75                  80

Trp Trp Ser Ser Val Ser Phe Lys Asn Met Phe Tyr Thr Asp Thr Pro
                85                  90                  95

Gln Ser Val Ile Lys Gln Arg Cys Glu Gln Thr Leu Asp Leu Ala Asn
            100                 105                 110

Glu Asn Ala Asp Ile Thr Phe Phe Ala Ala Asp Asn Arg Phe Ser Tyr
        115                 120                 125

Asn His Thr Ile Trp Ser Asn Asp Pro Val Met Gln Pro Asp Gln Ile
    130                 135                 140

Asn Lys Val Val Ala Leu Gly Asp Ser Leu Ser Asp Thr Gly Asn Ile
145                 150                 155                 160

Phe Asn Ala Ser Gln Trp Arg Phe Pro Asn Pro Asn Ser Trp Phe Leu
                165                 170                 175

Gly His Phe Ser Asn Gly Phe Val Trp Thr Glu Tyr Ile Ala Gln Ala
            180                 185                 190

Lys Asn Leu Pro Leu Tyr Asn Trp Ala Val Gly Gly Ala Ala Gly Glu
        195                 200                 205

Asn Gln Tyr Ile Ala Leu Thr Gly Val Gly Glu Gln Val Ser Ser Tyr
    210                 215                 220

Leu Ala Tyr Ala Lys Leu Ala Lys Asn Tyr Lys Pro Ala Asn Thr Leu
225                 230                 235                 240

Phe Thr Leu Glu Phe Gly Leu Asn Asp Phe Met Asn Tyr Asn Arg Ser
                245                 250                 255

Val Pro Glu Val Lys Ser Asp Tyr Ala Glu Ala Leu Ile Lys Leu Thr
            260                 265                 270

Asp Ala Gly Ala Lys Asn Leu Leu Leu Met Thr Leu Pro Asp Ala Thr
        275                 280                 285

Arg Ala Pro Gln Phe Thr Tyr Ser Thr Gln Glu Glu Ile Asn Lys Ile
```

```
                    290                 295                 300
Arg Ala Lys Ile Val Glu Met Asn Glu Phe Ile Lys Ala Gln Ala Ala
305                 310                 315                 320

Tyr Tyr Thr Ala Gln Gly Tyr Asn Val Thr Leu Tyr Asp Thr His Ala
                325                 330                 335

Leu Phe Glu Ser Leu Thr Ala Asn Pro Glu Gln His Gly Phe Val Asn
                340                 345                 350

Ala Ser Gln Ala Cys Gln Asp Ile Asn Arg Ser Ser Ser Val Asp Tyr
            355                 360                 365

Leu Tyr His His Ser Leu Arg Ser Glu Cys Ala Ser Ser Gly Ser Asp
        370                 375                 380

Lys Phe Val Phe Trp Asp Val Thr His Pro Thr Ala Thr His His
385                 390                 395                 400

Tyr Val Ala Glu Lys Met Leu Glu Ser Thr Asn Gln Leu Ser Asn His
                405                 410                 415

Pro Phe

<210> SEQ ID NO 20
<211> LENGTH: 1254
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
atgaataaaa cgatcacatt gcttagcgct ctccttctcc cactctcttt tgcccatgca      60
gccgaaccta cactctcccc tgagatggtc agtgcatccc aagtaagatc ggctcaggca     120
aagcaaacgt acacgtacgt ccgatgctgg tatcgtactt catactccaa agatgagcca     180
gctactgatt gggaatgggc ggagaacccct gacggaagct acttcacttt ggatggttat     240
tggtggtcct ctgtttcgtt caagaacatg ttttacactg cacgccccca gagtgttatc     300
aagcagcgat gtgagcaaac ccttgatctc gccaacgaga acgcggatat cacgttcttc     360
gccgcagaca accgtttctc atataatcat accatttgga gcaacgatcc agttatgcaa     420
cccgaccaga tcaataaggt agttgcactc ggagattccc tctcggatac gggaaacatc     480
tttaacgcaa gtcagtggcg cttcccaaac ccgaacagtt ggttcttggg acatttctca     540
aacggattcg tctggacgga gtacattgcc aagctaaaa ccttcctct ttataactgg     600 gctgtgggtg gtgccgccgg tgaaaatcaa tatattgctc ttacaggagt tggagagcaa     660
gtctcttcat acctcgctta cgctaagttg gccaaaaatt acaagccagc caacactctt     720
ttcacactcg agtttggctt gaacgacttc atgaactata ccgttctgt accgagggta     780 aagtcagact acgcggaagc cttgattaag ctcaccgacg ctggcgcaaa gaacttgctt     840
cttatgacac tccctgatgc taccgcgcca ccacagttca cctactcgac ccaggaggag     900
attaataaga tcagagctaa gatcgttgaa atgaacgaat tcatcaaggc tcaagctgcc     960
tactatacgg ctcaaggtta taacgtaacc ctctatgata tcatgcact cttcgagagc    1020 ttgacggcta accccgagca acatggattt gtaaatgcta gtcaggcatg tcaggatatc    1080
aaccgaagtt ctagtgttga ttaccttat caccacagcc tccgcagcga gtgtgcctcg    1140
tctggaagcg acaaatttgt tttctgggat gtaactcatc caaccacggc gactcaccat    1200
tatgtagcag aaaagatgct cgagagtaca aaccaattgt ctaaccatcc cttc         1254
```

<210> SEQ ID NO 21
<211> LENGTH: 266
<212> TYPE: PRT
<213> ORGANISM: Vibrio harveyi

<400> SEQUENCE: 21

Met Arg Lys Ser Leu Leu Ala Leu Ser Leu Leu Ala Ala Thr Ser Ala
1               5                   10                  15

Pro Val Met Ala Ala Asp Tyr Ser Asp Gly Asp Ile His Lys Asn Asp
            20                  25                  30

Tyr Lys Trp Met Gln Phe Asn Leu Met Gly Ala Phe Asp Glu Leu Pro
        35                  40                  45

Gly Glu Ser Ser His Asp Tyr Leu Glu Met Glu Phe Gly Gly Arg Ser
    50                  55                  60

Gly Ile Phe Asp Leu Tyr Gly Tyr Val Asp Val Phe Asn Leu Ala Ser
65                  70                  75                  80

Asp Lys Gly Ser Asp Lys Val Gly Asp Pro Lys Ile Phe Met Lys Phe
                85                  90                  95

Ala Pro Arg Met Ser Ile Asp Gly Leu Thr Gly Lys Asp Leu Ser Phe
            100                 105                 110

Gly Pro Val Gln Glu Leu Tyr Val Ala Thr Leu Phe Glu Trp Asp Gly
        115                 120                 125

Thr Asp Tyr Lys Thr Asn Lys Phe Ser Val Asn Asn Gln Lys Val Gly
    130                 135                 140

Ile Gly Ser Asp Val Met Val Pro Trp Phe Gly Lys Val Gly Val Asn
145                 150                 155                 160

Leu Tyr Gly Thr Tyr Gln Gly Asn Gln Lys Asp Trp Asn Gly Phe Gln
                165                 170                 175

Ile Ser Thr Asn Trp Phe Lys Pro Phe Tyr Phe Glu Asn Gly Ser
            180                 185                 190

Phe Ile Ser Tyr Gln Gly Tyr Ile Asp Tyr Gln Phe Gly Met Lys Glu
        195                 200                 205

Lys Tyr Ser Ser Ala Ser Asn Gly Gly Ala Met Phe Asn Gly Ile Tyr
    210                 215                 220

Trp His Ser Asp Arg Phe Ala Val Gly Tyr Gly Leu Lys Gly Tyr Lys
225                 230                 235                 240

Asp Val Tyr Gly Ile Lys Asp Ser Asp Ala Leu Lys Ser Thr Gly Phe
                245                 250                 255

Gly His Tyr Ile Ala Val Thr Tyr Lys Phe
            260                 265

<210> SEQ ID NO 22
<211> LENGTH: 798
<212> TYPE: DNA
<213> ORGANISM: Vibrio harveyi

<400> SEQUENCE: 22
atgcgaaaga gcttgcttgc acttagtttg cttgctgcta catcagcacc cgttatggct      60
gcggattact cagacgggga tatccacaag aatgattata gtggatgca attcaacctc      120 atgggcgctt tcgatgaact cccgggagaa tcctctcatg attaccttga atgaattc       180 ggaggccgct ctggaatctt tgatttgtac ggttacgtcg atgtattcaa tcttgcatcc     240
gacaagggta gtgataaggt tggagatcca aaaatcttta tgaagttcgc cccgaggatg    300
tccatcgacg ggctcactgg taaggacttg agcttcggtc ccgttcagga gttgtacgtc    360
gccacacttt ttgagtggga tgggactgat tataaaacga ataagttctc tgtgaataat    420

```
cagaaagttg gaattggctc ggatgtcatg gtaccctggt tcggaaaagt gggtgtgaat        480
ctctacggga catatcaagg aaaccagaag gattggaacg gattccaaat cagtacgaac        540
tggtttaagc ccttctactt ctttgagaat ggttccttta tctcgtacca aggatacatt        600
gactaccagt ttggaatgaa ggagaagtat agttctgcct cgaacggagg cgcaatgttc        660
aacggaattt attggcactc ggaccgattt gccgtcgggt atggattgaa gggctataag        720
gatgtttacg gcattaagga ttcagacgct ttgaagtcta cgggatttgg acactacatc        780
gccgtcacat ataagttt                                                     798

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
agctccatgg gaaaatcatc tccgcaagag                                          30

<210> SEQ ID NO 24
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
agctggatcc tgattttttt gccaactctt ttaaa                                    35
```

DIATOM-BASED VACCINES

CROSS-REFERENCE TO RELATED APPLICATIONS

This application is a U.S. national phase under 35 U.S.C. §371 of Intl. Appl. No. PCT/US2012/062112, filed on Oct. 26, 2012, which claims the benefit under 35 U.S.C. §119(e) of U.S. Provisional Application No. 61/553,139, filed on Oct. 28, 2011, which are hereby incorporated herein by reference in their entirety for all purposes.

SEQUENCE LISTING

The instant application contains a Sequence Listing which has been submitted electronically in ASCII format and is hereby incorporated by reference in its entirety. Said ASCII copy, created on May 30, 2014, is named UCSDP022US_SL.txt and is 66,331 bytes in size.

STATEMENT OF GOVERNMENTAL SUPPORT

This invention was made with government support under Grant No. FA9550-08-1-0178, awarded by the Air Force Office of Scientific Research (AFOSR), and Grant Nos. 2011-67015-30177 and 2012-67015-30197, awarded by The National Institute of Food and Agriculture/USDA. The government has certain rights in the invention.

FIELD

The present invention relates to diatom-based vaccines.

BACKGROUND

Killed pathogen vaccines are expensive, require additional adjuvants and two or more doses and often have side effects. Alternatively, live modified or recombinant attenuated bacterial or virus vectored vaccines may revert to virulence, interfere with the normal flora or cause problems with environmental containment.

SUMMARY

In one aspect, the invention provides a diatom or population of diatoms, comprising an antigen, wherein the antigen is heterologous to the diatom. In some embodiments, the antigen is mixed with or attached to the diatom. In some embodiments, the antigen is attached to the surface of the diatom. In some embodiments, the antigen is in the cytoplasm of the diatom. In some embodiments, the antigen is in the membrane system of the diatom. In some embodiments, the antigen is in the plasma membrane of the diatom. In some embodiments, the antigen is a peptide or polypeptide comprising one or more immunostimulatory epitopes.

In some embodiments, the diatom comprises a nucleic acid encoding the antigen and expresses the antigen. In some embodiments, the antigen is expressed and/or translated in the cytoplasm of the diatom. In some embodiments, the antigen is expressed and or trafficked to the surface or attached to the surface of the diatom. In some embodiments, the antigen is expressed and/or trafficked to the cell membrane system of the diatom. In some embodiments, the antigen is expressed and/or trafficked to the plasma membrane of the diatom. In some embodiments, the antigen is expressed as a fusion protein with a surface-expressed polypeptide endogenous to the diatom. In some embodiments, the surface-expressed polypeptide endogenous to the diatom is a diatom cell surface polypeptide, e.g., frustulin or p150 cell surface protein. In some embodiments, the antigen is expressed as a fusion protein with ε-frustulin. In some embodiments, the antigen is expressed as a fusion protein with a frustulin protein having at least 90% sequence identity, e.g., at least 91%, 92%, 93%, 94%, 95%, 96%, 97%, 98%, 99% or 100% sequence identity, to a frustulin protein of SEQ ID NO:6 or SEQ ID NO:7. In some embodiments, the antigen is expressed under the control of a promoter endogenous to the diatom. In some embodiments, the promoter endogenous to the diatom is an rpL41promoter or a fucoxanthin chlorophyll binding protein (FCP) promoter.

In a related aspect, the invention provides expression cassettes capable of and suitable for expressing recombinant antigenic peptides and proteins in a diatom host cell. In some embodiments, the expression cassettes comprise:

i) a promoter selected from the group consisting of fucoxanthin chlorophyll binding protein (FCP) promoter and ribosomal protein L41 (rpL41) promoter; the promoter operably linked to;

ii) a nucleic acid encoding a diatom cell surface polypeptide selected from a frustulin and p150 cell surface protein; the nucleic acid encoding the diatom cell surface polypeptide operably linked to; and iii) a nucleic acid encoding an antigen heterologous to a diatom. The expression cassette drives or promotes expression of the antigen in the diatom, in varying embodiments in the membrane system of or to the surface of the diatom. Embodiments of the antigens are as described below and herein. In varying embodiments, the fucoxanthin chlorophyll binding protein (FCP) promoter is a nucleic acid having at least at least 90% sequence identity, e.g., at least 91%, 92%, 93%, 94%, 95%, 96%, 97%, 98%, 99% or 100% sequence identity, to SEQ ID NO:1. In varying embodiments, the nucleic acid encoding a diatom cell surface polypeptide encodes ε-frustulin or a frustulin polypeptide having at least at least 90% sequence identity, e.g., at least 91%, 92%, 93%, 94%, 95%, 96%, 97%, 98%, 99% or 100% sequence identity, to SEQ ID NO:6 or SEQ ID NO:7.

The invention further provides plasmids or vectors comprising the expression cassettes. In varying embodiments, the plasmid or vector comprises a Gateway™ backbone. In varying embodiments, the plasmid or vector comprises a plasmid comprising a nucleic acid sequence having at least 90% sequence identity, e.g., at least 91%, 92%, 93%, 94%, 95%, 96%, 97%, 98%, 99% or 100% sequence identity, to a plasmid of SEQ ID NOs:8, 9 or 10. In further aspects, the invention provides diatom host cells comprising the expression cassettes and/or plasmids or vectors. Embodiments of the diatom host cells are as described herein.

In some embodiments, the diatom is an intact cell or population of intact cells. In some embodiments, the diatom is a live cell or population of live cells. In some embodiments the diatom or population of diatoms are intact but dead cells. In some embodiments the diatom or population of diatoms are formulated as microparticles or nanoparticles.

In some embodiments, the antigen induces and/or elicits an immune response against the antigen in an animal. Generally, the immune response against the antigen is protective, e.g., prevents or treats a disease in the animal. In various embodiments, the animal is a mammal, a bony fish (e.g., Salmoniformes, Salmonoidei, Salmonidae), a shrimp or prawn (e.g., Penaeoidea, Penaeidae, Litopenaeus), a mollusk (e.g., Mollusca; Bivalvia) or an avian (e.g., Aves, Galliformes (a fowl), Phasianidae; Phasianinae; Gallus). In some embodiments, the antigen is an immunostimulatory polypeptide or peptide.

In some embodiments, the antigen is a viral antigen (e.g., influenza, varicella zoster, herpes, HIV, respiratory syncytial virus (RSV), papilloma, Hepatitis A, Hepatitis B, Hepatitis C), a bacterial antigen (e.g., *Vibrio, Salmonella, E. coli, Shigella, Campylobacter, Yersinia, Histophilus, Staphylococcus, Streptococcus, Legionella*), a fungal antigen (e.g., *Cryptococcus, Candida*) or a parasitic antigen (e.g., *Plasmodium, Trypanosoma*).

In some embodiments, the animal is a mammal. In some embodiments, the mammal is a human or a non-human primate. In some embodiments, the mammal is a domesticated mammal (e.g., feline or canine) In some embodiments, the mammal is an agricultural mammal (e.g., bovine, ovine, porcine, equine). In some embodiments, the animal is a laboratory animal (e.g. mouse, rat, rabbit, hamster, guinea pig). In varying embodiments, the animal is a marine animal, e.g., a fish, a crustacean, a mollusk. In some embodiments, the animal is a bony fish (e.g., Salmoniformes, Salmonoidei, Salmonidae), e.g., salmon, trout, catfish, whitefish, tilapia, bass, char, or another species of farmed fish. In some embodiments, the animal is a crustacean, e.g., a shrimp or prawn (e.g., Penaeoidea, Penaeidae, Litopenaeus), e.g., a penaeid shrimp, e.g., white shrimp, pink shrimp, pinkspotted shrimp, brown shrimp, blue shrimp, crystal shrimp, black tiger shrimp. In some embodiments, the animal is a mollusk or bivalve, e.g., a clam, an oyster. In some embodiments, the animal is an avian, e.g., a fowl, e.g., a turkey, a chicken.

In some embodiments, the antigen is a viral antigen (e.g., influenza, varicella zoster, herpes, HIV, RSV, papilloma, Hepatitis A, Hepatitis B, Hepatitis C). In some embodiments, the antigen induces and/or elicits a protective immune response in the animal against a viral antigen.

In some embodiments, the antigen is a bacterial antigen (e.g., *Vibrio, Salmonella, E. coli, Shigella, Campylobacter, Yersinia, Histophilus, Staphylococcus, Streptococcus, Legionella*). In some embodiments, the antigen induces and/or elicits a protective immune response in the animal against a bacterial antigen. In some embodiments, the antigen induces and/or elicits a protective immune response in the animal against a bacterial pathogen selected from the group consisting of *Vibrio, Salmonella, Shigella, Campylobacter, Yersinia, Histophilus, Staphylococcus, Streptococcus, Legionella, Listonella, Moritella, Aeromonas, Piscirickettsia, Flavobacterium, Edwardsiella, Renibacterium, Lactococcus* and *Photobacterium*. Bacterial pathogens to marine animals, e.g., fish, include without limitation *Vibrio* spp., *Listonella anguillarum, Vibrio harveyi., Vibrio salmonicida, Moritella viscosa, Aeromonas salmonicida* subsp. *salmonicida, Aeromonas salmonicida, Yersinia ruckeri, Piscirickettsia salmonis, Flavobacterium branchiophilum, Flavobacterium psychrophilum, Edwardsiella ictaluri, Edwardsiella tarda, Renibacterium salmoninarum, Lactococcus garvieae, Photobacterium damsela* subspecies *piscicida, Streptococcus iniae, Streptococcus phocae*, and *Flavobacterium columnare*.

In some embodiments, the antigen elicits and/or induces a protective immune response in the mammal against a *Histophilus somni* infection. In some embodiments, the antigen comprises one or more epitopes of *H. somni* virulence factor Immunoglobulin Binding Protein A (IbpA). In some embodiments, the antigen comprises the IbpA DR2 domain. In varying embodiments, the IbpA DR2 domain is encoded by a nucleic acid sequence having at least 90% sequence identity, e.g., at least 91%, 92%, 93%, 94%, 95%, 96%, 97%, 98%, 99% or 100% sequence identity, to a nucleic acid of SEQ ID NO:4. In varying embodiments, the antigen comprises the IbpA DR2 domain and IbpA5, e.g., expressed as separate antigens or as a fusion protein. In varying embodiments, the antigen comprises the IbpA DR2 domain and BRSV N protein, e.g., expressed as separate antigens or as a fusion protein. In varying embodiments, the antigen comprises the IbpA DR2 domain and one or more BRSV antigens selected from N protein, F protein and G protein.

In some embodiments, the antigen induces and/or elicits a protective immune response in the mammal against bovine respiratory syncytial virus (BRSV), parainfluenza-3 ($PI_3$), bovine viral diarrhea virus (BVDV) or bovine herpes virus 1 (BHV-1). In some embodiments, the antigen comprises BRSV N, F and/or G proteins. In some embodiments, the antigen induces and/or elicits a protective immune response in the mammal against infection of a bacterium selected from the group consisting of *Mannheimia haemolytica, Pasteurella multocida, Mycoplasma bovis, Vibrio parahaemolyticus* and *Legionella pneumophila*.

In some embodiments, the antigen induces and/or elicits a protective immune response in the mammal against a *Vibrio cholerae* infection. In some embodiments, the antigen comprises one or more epitopes of Cholera Toxin B (CTB) or Cholera Toxin A (CTA). In some embodiments, the antigen comprises one or more epitopes of *V. cholerae* colonization factors TcpA, TcpF and CBP-A. In some embodiments, the antigen comprises a Tcp-A2-CTB chimera. In some embodiments, the antigen comprises CTB and TcpA, e.g., expressed separately or as a fusion protein. In some embodiments, the antigen comprises CTB and TcpF, e.g., expressed separately or as a fusion protein. In some embodiments, the antigen comprises toxin co-regulated pilus (TCP), TcpA, TcpF and the chitin binding product (CBP-A), e.g., expressed separately or as a fusion protein. In some embodiments, the antigen comprises a combination of the above *V. cholera* antigens.

In some embodiments, the antigen induces and/or elicits a protective immune response in the animal against an enteric pathogen (e.g., *Salmonella, Shigella, Campylobacter, Yersinia, Escherichia coli, Giardia, Entamoeba histolytica*). In some embodiments, the antigen induces and/or elicits a protective immune response in the animal against an infection of an enteric pathogen selected from the group consisting of *Salmonella typhimurium, Yersinia enterocolitica, Shigella sonnei, Shigella flexneri, Campylobacter jejuni, Entamoeba histolytica*, or *Giardia* spp.

In some embodiments, the immunogenic protein expressed on the surface of or with the diatom may be used for oral vaccination of marine animals, e.g., fish, crustaceans (e.g., shrimp or prawns), or mollusks (e.g., bivalves). For example, shrimp populations are susceptible to a number of viral diseases, including without limitation, infectious hypodermal and hematopoietic necrosis virus (IHHNV), yellow head virus (YHV), taura syndrome virus (TSV), infectious myonecrosis (IMN), and white spot syndrome virus (WSSV). Fish are susceptible to a number of viral diseases, including without limitation, infectious pancreatic necrosis (IPNV), pancreas disease (PDV), infectious salmon anemia (ISAV), infectious hematopoietic necrosis (VHSV), viral nervous necrosis, iridoviral disease (RSIV), channel catfish virus disease (CCV), spring viremia of carp (SVCV), and grass carp hemorrhage disease (GCHDV).

In varying embodiments, the antigen elicits and/or induces a protective immune response against white spot syndrome virus (WSSV). In varying embodiments, the WSSV antigen is one or both of VP19 and VP466 proteins. In varying embodiments, the VP19 protein comprises an amino acid sequence having at least 90% sequence identity, e.g., at least 91%, 92%, 93%, 94%, 95%, 96%, 97%, 98%, 99% or 100% sequence identity, to SEQ ID NO: 11. In varying embodiments, the VP19 protein is encoded by a nucleic acid sequence having at least 90% sequence identity, e.g., at least 91%, 92%, 93%, 94%, 95%, 96%, 97%, 98%, 99% or 100% sequence identity, to SEQ ID NO: 12. In varying embodiments, the VP466 protein comprises an amino acid sequence having at least 90% sequence identity, e.g., at least 91%, 92%, 93%, 94%, 95%, 96%, 97%, 98%, 99% or 100% sequence identity, to SEQ ID NO: 13. In varying embodiments, the VP466 protein is encoded by a nucleic acid sequence having at least 90% sequence identity, e.g., at least 91%, 92%, 93%, 94%, 95%, 96%, 97%, 98%, 99% or 100% sequence identity, to SEQ ID NO: 14.

In varying embodiments, the antigen elicits and/or induces a protective immune response against *Vibrio harveyi*. In varying embodiments, the *V. harveyi* antigen is one or more of VhhP2, DegQ$_{vh}$, Vh-HL1 and Vh-ompK proteins. In varying embodiments, the VhhP2 protein comprises an amino acid sequence having at least 90% sequence identity, e.g., at least 91%, 92%, 93%, 94%, 95%, 96%, 97%, 98%, 99% or 100% sequence identity, to SEQ ID NO: 15. In varying embodiments, the VhhP2 protein is encoded by a nucleic acid sequence having at least 90% sequence identity, e.g., at least 91%, 92%, 93%, 94%, 95%, 96%, 97%, 98%, 99% or 100% sequence identity, to SEQ ID NO: 16. In varying embodiments, the DegQ$_{vh}$ protein comprises an amino acid sequence having at least 90% sequence identity, e.g., at least 91%, 92%, 93%, 94%, 95%, 96%, 97%, 98%, 99% or 100% sequence identity, to SEQ ID NO: 17. In varying embodiments, the DegQ$_{vh}$ protein is encoded by a nucleic acid sequence having at least 90% sequence identity, e.g., at least 91%, 92%, 93%, 94%, 95%, 96%, 97%, 98%, 99% or 100% sequence identity, to SEQ ID NO: 18. In varying embodiments, the Vh-HL1 protein comprises an amino acid sequence having at least 90% sequence identity, e.g., at least 91%, 92%, 93%, 94%, 95%, 96%, 97%, 98%, 99% or 100% sequence identity, to SEQ ID NO: 19. In varying embodiments, the Vh-HL1 protein is encoded by a nucleic acid sequence having at least 90% sequence identity, e.g., at least 91%, 92%, 93%, 94%, 95%, 96%, 97%, 98%, 99% or 100% sequence identity, to SEQ ID NO: 20. In varying embodiments, the Vh-ompK protein comprises an amino acid sequence having at least 90% sequence identity, e.g., at least 91%, 92%, 93%, 94%, 95%, 96%, 97%, 98%, 99% or 100% sequence identity, to SEQ ID NO: 21. In varying embodiments, the Vh-ompK protein is encoded by a nucleic acid sequence having at least 90% sequence identity, e.g., at least 91%, 92%, 93%, 94%, 95%, 96%, 97%, 98%, 99% or 100% sequence identity, to SEQ ID NO: 22.

In some embodiments, the antigen is a cancer-associated antigen.

In some embodiments, the diatom is a Bacillariophyta (e.g., Bacillariophyceae (Raphid, pennate diatoms), Coscinodiscophyceae (centric diatoms), Fragilariophyceae (Araphid, pennate diatoms) and/or Mediophyceae). In some embodiments, the diatom is a Coscinodiscophyceae (e.g., Chaetocerotophycidae, Corethrophycidae, Coscinodiscophycidae, Rhizosoleniophycidae, and/or Thalassiosirophycidae). In some embodiments, the diatom is a Thalassiosirophycidae. In some embodiments, the diatom is a Thalassiosirales. In some embodiments, the diatom is a Thalassiosiraceae. In some embodiments, the diatom is of the genus *Thalassiosira* (e.g., *Thalassiosira aestivalis, Thalassiosira allenii, Thalassiosira angulate, Thalassiosira anguste-lineata, Thalassiosira antarctica, Thalassiosira antarctica* var. *borealis, Thalassiosira aff. antarctica, Thalassiosira concaviuscula, Thalassiosira curviseriata, Thalassiosira delicatula, Thalassiosira eccentric, Thalassiosira gessneri, Thalassiosira gravida, Thalassiosira guillardii, Thalassiosira hendeyi, Thalassiosira lundiana, Thalassiosira mala, Thalassiosira mediterranea, Thalassiosira minima, Thalassiosira minuscula, Thalassiosira nodulolineata, Thalassiosira nordenskioeldii, Thalassiosira oceanica, Thalassiosira pacifica, Thalassiosira profunda, Thalassiosira proschkinae, Thalassiosira pseudonana, Thalassiosira punctigera, Thalassiosira rotula, Thalassiosira tenera, Thalassiosira tumida, Thalassiosira weissflogii, Thalassiosira* sp. 422A, *Thalassiosira* sp. B101, *Thalassiosira* sp. CC03-04, *Thalassiosira* sp. CCMP1064, *Thalassiosira* sp. CCMP1065, *Thalassiosira* sp. CCMP1093, *Thalassiosira* sp. CCMP1277, *Thalassiosira* sp. CCMP1281, *Thalassiosira* sp. CCMP1987, *Thalassiosira* sp. CCMP353, *Thalassiosira* sp. CCMP988, *Thalassiosira* sp. CCMP991, *Thalassiosira* sp. Cleve BA153110, *Thalassiosira* sp. DDZ-2010a, *Thalassiosira* sp. DITS301-08, *Thalassiosira* sp. MBTD-CMFRI-S033, *Thalassiosira* sp. MBTD-CMFRI-S069, and/or *Thalassiosira* sp. MBTD-CMFRI-S132. In some embodiments, the diatom is *Thalassiosira pseudonana*.

In varying embodiments, the diatom or population of diatoms comprise no additional adjuvant; the silica in the diatom cell wall acts as an adjuvant. In some embodiments, the diatom or population of diatoms further comprise an adjuvant. The adjuvant can be in the cytoplasm or attached to the surface of the diatom. In some embodiments, the adjuvant is a bacterial toxin. In some embodiments, the bacterial toxin is selected from the group consisting of Cholera Toxin B (CTB), *E. coli* heat labile toxin (LT), tetanus toxin (Tet), and fragments thereof that stimulate and/or enhance an immune response. In some embodiments, the diatom comprises a nucleic acid encoding the bacterial toxin or fragment thereof, and expresses the bacterial toxin or fragment thereof. The bacterial toxin adjuvant may be expressed in the cytoplasm, membrane system (e.g., plasma membrane) or on the surface of the diatom. In some embodiments, the antigen and the bacterial toxin are expressed as a fusion protein. In some embodiments, the adjuvant is a cytokine. In some embodiments, the cytokine is selected from the group consisting of IL-1, IL-2, IL-5, IL-6, IL-12, IL-15, Flt3L, GM-CSF, MIP-1α, IFN-γ, and mixtures thereof. In some embodiments, the diatom comprises a nucleic acid encoding the cytokine or fragment thereof, and expresses the cytokine or fragment thereof. The cytokine may be expressed in the cytoplasm, in the membrane system or on the surface of the diatom. In some embodiments, the antigen and the cytokine are expressed as a fusion protein. In some embodiments, the adjuvant is a Toll-like receptor agonist, e.g., flagellin and/or Meningococcal outer membrane protein C (OMP C).

In a further aspect, the invention comprises compositions comprising a diatom or population of diatoms, as described herein and a pharmaceutically acceptable carrier.

In another aspect, the invention comprises methods of stimulating (e.g., inducing and/or eliciting) an immune response in an animal, comprising administering to the animal a diatom or population of diatoms, as described herein, or a composition, as described herein, in an amount effective to stimulate the immune response in the animal. Administration of the diatom induces and/or elicits an immune response against the antigen expressed by the diatom. Generally, the immune response against the antigen is protective, e.g., prevents or treats a disease in the animal.

In some embodiments, the diatom or population of diatoms are administered mucosally or transdermally. In some embodiments the diatoms or populations are administered in the water or food or by aerosol. In some embodiments, the diatom or population of diatoms are administered across the oral, ocular, nasal, vaginal, rectal, pulmonary or conjunctival mucosa. In some embodiments, the diatom or population of diatoms are administered orally, sublingually, buccally, intranasally, intravaginally, intrarectally, conjunctivally, intrapulmonarily, by aerosol or transdermally. In some embodiments, the diatom or population of diatoms is administered systemically.

DEFINITIONS

As used herein, the term "diatom" refers to any of various microscopic one-celled or colonial algae of the phylum Bacillariophyta. In varying embodiments, the diatom is of the class Coscinodiscophyceae (e.g., Chaetocerotophycidae, Corethrophycidae, Coscinodiscophycidae, Rhizosoleniophycidae, and/or Thalassiosirophycidae). In some embodiments, the diatom is a Thalassiosirophycidae. In some embodiments, the diatom is a Thalassiosirales. In some embodiments, the diatom is of the family Thalassiosiraceae. In some embodiments, the diatom is of the genus *Thalassiosira*. Diatoms of use preferably have cell walls of silica. Generally, the cell walls of silica comprise two halves called the epitheca and hyptotheca.

The term "antigen" refers to a peptide or polypeptide that elicits and/or induces an immune response in an animal. Preferably, the immune response is protective or therapeutic (e.g., treats an ongoing disease), e.g., against an infectious agent or a cancer-associated antigen.

The term "heterologous" refers to antigens (e.g., peptides, polypeptides) that are not endogenous to the diatom.

The term "administration" refers to all routes of immunization, including systemic and local administration.

The terms "systemic administration" and "systemically administered" refer to a method of administering a compound or composition to an animal so that the compound or composition is delivered to sites in the body, including the targeted site of pharmaceutical action, via the circulatory system. Systemic administration includes, but is not limited to, oral, mucosal (e.g., oral, intranasal, intravaginal, intrarectal, conjunctival, sublingually, buccally, intrapulmonary, or by aerosol) and parenteral (e.g., other than through the alimentary tract, such as intramuscular, intravenous, intra-arterial, transdermal and subcutaneous) administration, as well as administration into the egg (in ovo).

The terms "mucosal administration" and "mucosal immunization" refers to administration via a mucosal surface, e.g., oral, intranasal, intravaginal, intrarectal, conjunctival, sublingually, buccally, intrapulmonary, or by aerosol. See, e.g., Pavot, et al., *Vaccine* 30 (2012) 142-154.

The term "co-administering" or "concurrent administration", when used, for example with respect to the antigen and another active agent (e.g., an adjuvant or a second antigen), refers to administration of the compound and/or analogs and the active agent such that both can simultaneously achieve a physiological effect. The two agents, however, need not be administered together. In certain embodiments, administration of one agent can precede administration of the other. Simultaneous physiological effect need not necessarily require presence of both agents in the circulation at the same time. However, in certain embodiments, co-administering typically results in both agents being simultaneously present in the body (e.g., in the plasma) at a significant fraction (e.g., 20% or greater, preferably 30% or 40% or greater, more preferably 50% or 60% or greater, most preferably 70% or 80% or 90% or greater) of their maximum serum concentration for any given dose.

The term "effective amount" or "pharmaceutically effective amount" refer to the amount and/or dosage, and/or dosage regime of one or more compounds necessary to bring about the desired result e.g., an amount sufficient to mitigating in an animal one or more symptoms associated with the disease being treated or prevented, or an amount sufficient to lessen the severity or delay the progression of the disease being treated in an animal (e.g., therapeutically effective amounts), an amount sufficient to reduce the risk or delaying the onset, and/or reduce the ultimate severity of a disease being prevented in an animal (e.g., prophylactically effective amounts).

The phrase "cause to be administered" refers to the actions taken by a medical professional (e.g., a physician), or a person controlling medical care of a subject, that control and/or permit the administration of the agent(s)/compound(s) at issue to the subject. Causing to be administered can involve diagnosis and/or determination of an appropriate therapeutic or prophylactic regimen, and/or prescribing particular agent(s)/compounds for a subject. Such prescribing can include, for example, drafting a prescription form, annotating a medical record, and the like.

As used herein, the terms "treating" and "treatment" refer to delaying the onset of, retarding or reversing the progress of, reducing the severity of, or alleviating or preventing either the disease or condition to which the term applies, or one or more symptoms of such disease or condition.

The term "mitigating" refers to reduction or elimination of one or more symptoms of that pathology or disease, and/or a reduction in the rate or delay of onset or severity of one or more symptoms of that pathology or disease, and/or the prevention of that pathology or disease. In certain embodiments, the reduction or elimination of one or more symptoms of pathology or disease can include, but is not limited to, reduction or elimination burden of the infectious agent or cancer.

The terms "subject," "individual," and "patient" interchangeably refer to an animal, e.g., a mammal, a bony fish (e.g., Salmoniformes, Salmonoidei, Salmonidae), a shrimp or prawn (e.g., Penaeoidea, Penaeidae, Litopenaeus), a mollusk (e.g., Mollusca; Bivalvia) or an avian (e.g., Ayes, Galliformes (a fowl), Phasianidae; Phasianinae; Gallus). In varying embodiments, the animal is a human or a non-human primate, but also domesticated mammals (e.g., canine or feline), laboratory mammals (e.g., mouse, rat, rabbit, hamster, guinea pig) and agricultural mammals (e.g., equine, bovine, porcine, ovine). In various embodiments, the subject can be a human (e.g., adult male, adult female, adolescent male, adolescent female, male child, female child) under the care of a physician or other healthworker in a hospital, psychiatric care facility, as an outpatient, or other clinical context. In certain embodiments the subject may not be under the care or prescription of a physician or other healthworker.

A "fusion protein" refers to a composition comprising at least one polypeptide or peptide domain which is associated with a second domain. The second domain can be a polypeptide, peptide, polysaccharide, or the like. The "fusion" can be an association generated by a peptide bond, a chemical linking, a charge interaction (e.g., electrostatic attractions, such as salt bridges, H-bonding, etc.) or the like. If the polypeptides are recombinant, the "fusion protein" can be translated from a common message. Alternatively, the compositions of the domains can be linked by any chemical or electrostatic means. The fusion proteins of the invention can also include additional sequences, e.g., linkers, epitope tags, enzyme cleavage recognition sequences, signal sequences, secretion signals, and the like.

An "immunogen" refers to a compound or composition comprising a peptide, polypeptide or protein which is "immunogenic," i.e., capable of eliciting, augmenting or boosting a cellular and/or humoral immune response, either alone or in combination or linked or fused to another substance. An immunogenic composition can be a peptide of at least about 5 amino acids, a peptide of 10 amino acids in length, a fragment 15 amino acids in length, a fragment 20 amino acids in length or greater. The immunogen can comprise a "carrier" polypeptide and a hapten, e.g., a fusion protein or a carrier polypeptide fused or linked (chemically or otherwise) to another composition (described below). The immunogen can be recombinantly expressed in an immunization vector, which can be simply naked DNA comprising the immunogen's coding sequence operably linked to a promoter, e.g., a simple expression cassette. The immunogen includes antigenic determinants, or epitopes (described below), to which antibodies or TCRs bind, which are typically 3 to 10 amino acids in length.

An "antibody" refers to a polypeptide of the immunoglobulin family or a polypeptide comprising fragments of an immunoglobulin that is capable of noncovalently, reversibly, and in a specific manner binding a corresponding antigen. An exemplary antibody structural unit comprises a tetramer. Each tetramer is composed of two identical pairs of polypeptide chains, each pair having one "light" (about 25 kD) and one "heavy" chain (about 50-70 kD), connected through a disulfide bond. The recognized immunoglobulin genes include the κ, λ, α, γ, δ, ε, and μ constant region genes, as well as the myriad immunoglobulin variable region genes. Light chains are classified as either κ or λ. Heavy chains are classified as γ, μ, α, δ, or ε, which in turn define the immunoglobulin classes, IgG, IgM, IgA, IgD, and IgE, respectively. The N-terminus of each chain defines a variable region of about 100 to 110 or more amino acids primarily responsible for antigen recognition. The terms variable light chain (VL) and variable heavy chain (VH) refer to these regions of light and heavy chains respectively. As used in this application, an "antibody" encompasses all variations of antibody and fragments thereof that possess a particular binding specifically, e.g., for tumor associated antigens. Thus, within the scope of this concept are full length antibodies, chimeric antibodies, humanized antibodies, human antibodies, single domain antibodies or nanobodies, single chain antibodies (ScFv), Fab, Fab', and multimeric versions of these fragments (e.g., F(ab')2) with the same binding specificity.

The phrase "specifically (or selectively) bind," when used in the context of describing the interaction between an antigen, e.g., a protein, to an antibody or antibody-derived binding agent, refers to a binding reaction that is determinative of the presence of the antigen in a heterogeneous population of proteins and other biologics, e.g., in a biological sample, e.g., a blood, serum, plasma or tissue sample. Thus, under designated immunoassay conditions, the antibodies or binding agents with a particular binding specificity bind to a particular antigen at least two times the background and do not substantially bind in a significant amount to other antigens present in the sample. Specific binding to an antibody or binding agent under such conditions may require the antibody or agent to have been selected for its specificity for a particular protein. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity). Typically a specific or selective binding reaction will produce a signal at least twice over the background signal and more typically at least than 10 to 100 times over the background.

A "transmission blocking antibody" is an antibody which inhibits the transmission to a host and/or growth or replication of an infectious agent, e.g., a virus, a bacterium, a fungus and/or a parasite.

An "immunogenic composition" is a composition which elicits the production of antibodies or a cell-mediated immune response when administered to an animal.

An "immunological carrier" or "carrier" in the immunological context (as opposed to a carrier which is a nonactive composition for the purpose of formulating, storing or carrying a pharmaceutical) is an composition which, when linked, joined, chemically coupled or fused to a second composition (e.g., protein, peptide, polysaccharide or the like) boosts or augments the cellular or humoral response to the composition. Any physiologic mechanism can be involved in this augmentation or boosting of the immune response. An immunogenic carrier is typically a polypeptide linked or fused to a second composition of interest comprising a protein, peptide or polysaccharide, where the carrier stimulates a cellular (T cell mediated) immune response that boosts or augments the humoral (B cell mediated, antibody-generating) immune response to the composition of interest. These second compositions can be "haptens," which are typically defined as compounds of low molecular weight or repeating low molecular weight units that are not immunogenic by themselves, but that, when coupled to carrier molecules, can elicit antibodies directed to epitopes on the hapten. For example, the lack of an adequate immune response to the major polysaccharide of the *Haemophilus influenzae* type b capsule (PRP) in very young infants can be overcome by conjugating PRP to a T-cell dependent carrier protein (see Zepp (1997) Eur. J. Pediatr. 156:18-24). Alternatively, a peptide can be linked to a carrier simply to facilitate manipulation of the peptide in the generation of the immune response (see, e.g., Rondard (1997) Biochemistry 36:8962-8968).

An "epitope" refers to an antigenic determinant or antigen site that interacts with an antibody or a T cell receptor (TCR). An "antigen" is a molecule or composition that induces the production of an immune response. An antibody or TCR binds to a specific conformational (possibly charge-dependent) domain of the antigen, called the "antigenic determinant" or "epitope" (TCRs bind the epitope in association with a third molecule, a major histocompatibility complex (MHC) protein).

The terms "cancer-associated antigen" or "tumor-associated antigen" or "tumor-specific marker" or "tumor marker" interchangeably refers to a molecule (typically protein, carbohydrate or lipid) that is preferentially expressed on the surface of a cancer cell in comparison to a normal cell, and which is useful for inducing and/or eliciting an immune response against the cancer cell or tumor. Oftentimes, a cancer-associated antigen is a cell surface molecule that is overexpressed in a cancer cell in comparison to a normal cell, for instance, 1-fold over expression, 2-fold overexpression, 3-fold overexpression or more in comparison to a normal cell. Oftentimes, a cancer-associated antigen is a cell surface molecule that is inappropriately synthesized in the cancer cell, for instance, a molecule that contains deletions, additions or mutations in comparison to the molecule expressed on a normal cell. Oftentimes, a cancer-associated antigen will be expressed exclusively on the cell surface of a cancer cell and not synthesized or expressed on the surface of a normal cell. Examples of known TAAs include without limitation, melanoma associated antigens (MAGE-1, MAGE-3, TRP-2, melanosomal membrane glycoprotein gp100, gp75 and MUC-1 (mucin-1) associated with melanoma); CEA (carcinoembryonic antigen) which can be associated, e.g., with ovarian, melanoma or colon cancers; folate receptor alpha expressed by ovarian carcinoma; free human chorionic gonadotropin beta (hCGβ) subunit expressed by many different tumors, including but not limited to myeloma; HER-2/neu associated with breast cancer; encephalomyelitis antigen HuD associated with small-cell lung cancer; tyrosine hydroxylase associated with neuroblastoma; prostate-specific antigen (PSA) associated with prostate cancer; CA125 associated with ovarian cancer; and the idiotypic determinants of a B cell lymphoma can generate tumor-specific immunity (attributed to idiotype-specific humoral immune response). Moreover, antigens of human T cell leukemia virus type 1 have been shown to induce specific CTL responses and antitumor immunity against the virus-induced human adult T cell leukemia (ATL). See, e.g., Haupt, et al., Experimental Biology and Medicine (2002) 227:227-237; Ohashi, et al., Journal of Virology (2000) 74(20):9610-9616.

The terms "identical" or percent "identity," and variants thereof in the context of two or more polynucleotide sequences, refer to two or more sequences or subsequences that are the same. Sequences are "substantially identical" if they have a specified percentage of nucleic acid residues or nucleotides that are the same (e.g., at least 60% identity, optionally at least 65%, 70%, 75%, 80%, 85%, 90%, 95%, 96%, 97%, 98%, or 99% identity over a specified region (or the whole reference sequence when not specified)), when compared to a reference sequence (e.g., SEQ ID NOs: 1-22) and aligned for maximum correspondence over a comparison window, or designated region as measured using one of the following sequence comparison algorithms or by manual alignment and visual inspection. The present invention provides polynucleotides improved for expression in diatom host cells that are substantially identical to the polynucleotides of described herein. Optionally, the identity exists over a region that is at least about 50 amino acids in length, or more preferably over a region that is 100, 200, 300, 400, 500, 600, 800, 1000, or more, nucleic acids in length, or over the full-length of the sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The term "comparison window", and variants thereof, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can also be conducted by the local homology algorithm of Smith and Waterman Add. APL. Math. 2:482 (1981), by the homology alignment algorithm of Needle man and Wunsch J. Mol. Biol. 48:443 (1970), by the search for similarity method of Pearson and Lipman Proc. Natl. Acad. Sci. (U.S.A.) 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), Karlin and Altschul Proc. Natl. Acad. Sci. (U.S.A.) 87:2264-2268(1990), or by manual alignment and visual inspection (see, e.g., Ausubel et al., Current Protocols in Molecular Biology (1995 supplement)).

Examples of an algorithm that is suitable for determining percent sequence identity and sequence similarity include the BLAST and BLAST 2.0 algorithms, which are described in Altschul et al. (1977) Nuc. Acids Res. 25:3389-3402, and Altschul et al. (1990) J. Mol. Biol. 215:403-410, respectively. Software for performing BLAST analyses is publicly available through the National Center for Biotechnology Information (on the internet at ncbi.nlm.nih). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001. Standard BLAST algorithm parameters have an expected threshold of 10 (according to the stochastic model of Karlin and Altschul (PNAS, 87:2264-2268(1990)); a word size of 28; reward and penalty of 1/−2 (a ratio of 0.5, or 1/−2, is used for sequences that are 95% conserved); and a linear GAP cost.

The term "substantial identity" of polynucleotide sequences means that a polynucleotide comprises a sequence that has at least 80% sequence identity, e.g., at least about 85%, 90%, 91%, 92%, 93%, 94%, 95%, 96%, 97%, 98%, 99%, or higher, compared to a reference sequence (e.g., SEQ ID NOs: 1-22), using sequence alignment/comparison algorithms set to standard parameters. One of skill will recognize that these values can be appropriately adjusted to determine corresponding identity of proteins encoded by two nucleotide sequences by taking into account codon degeneracy, amino acid similarity, reading frame positioning and the like.

"Substantial identity" of amino acid sequences for these purposes means sequence identity of at least 80% sequence identity, e.g., at least about 85%, 90%, 91%, 92%, 93%, 94%, 95%, 96%, 97%, 98%, 99%, or higher, using sequence alignment/comparison algorithms set to standard parameters. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, asp arctic acid-glutamic acid, and asparagine-glutamine. Determination of "substantial identity" can be focused over defined subsequences, such as known structural domains.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 1 molar at pH 7 and the temperature is at least about 60° C.

In the present invention, mRNA encoded by the nucleic acids of the invention can be identified in Northern blots under stringent conditions using the sequences disclosed here or fragments of, typically, at least about 100 nucleotides. For the purposes of this disclosure, stringent conditions for such RNA-DNA hybridizations are those which include at least one wash in 6×SSC for 20 minutes at a temperature of at least about 50° C., usually about 55° C. to about 60° C., or equivalent conditions.

Another indication that protein sequences are substantially identical is if one protein is immunologically reactive with antibodies raised against the other protein.

Conservatively modified variations" of a particular nucleic acid sequence refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every nucleic acid sequence herein which encodes a polypeptide also describes every possible silent variation. One of skill will recognize that each codon in a nucleic acid (except AUG, which is ordinarily the only codon for methionine, and UGG, the single codon for Trp) can be modified to yield a functionally identical molecule by standard techniques. Accordingly, each "silent variation" of a nucleic acid which encodes a polypeptide is implicit in each described sequence.

The term "conservatively modified variations" refers to individual substitutions, deletions or additions which alter, add or delete a single amino acid or a small percentage of amino acids (typically less than 5%, more typically less than 1%) in an encoded sequence, where the alterations result in the substitution of an amino acid with a chemically similar amino acid; and the alterations, deletions or additions do not alter the structure, function and/or immunogenicity of the sequence. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

The term "frustulin" refers to nucleic acids and polypeptide polymorphic variants, alleles, mutants, and interspecies homologs that: (1) have an amino acid sequence that has greater than about 90% amino acid sequence identity, for example, 91%, 92%, 93%, 94%, 95%, 96%, 97%, 98% or 99% or greater amino acid sequence identity, preferably over a region of at least about 25, 50, 75, 100, 200, 400, or more amino acids, or over the full-length, to an amino acid sequence encoded by a frustulin nucleic acid (e.g., GenBank Accession Nos. XM_002290463.1 (FRU1) and XM_002290320.1 (FRU2); (2) bind to antibodies, e.g., polyclonal antibodies, raised against an immunogen comprising an amino acid sequence of a frustulin polypeptide (e.g., XP_002290499.1 (FRU1) and XP_002290356.1 (FRU2)); or an amino acid sequence encoded by a frustulin nucleic acid (e.g., frustulin polynucleotides described herein), and conservatively modified variants thereof; (3) specifically hybridize under stringent hybridization conditions to an anti-sense strand corresponding to a nucleic acid sequence encoding a frustulin protein, and conservatively modified variants thereof; (4) have a nucleic acid sequence that has greater than about 90%, preferably greater than about 91%, 92%, 93%, 94%, 95%, 96%, 97%, 98%, 99%, or higher nucleotide sequence identity, preferably over a region of at least about 25, 50, 100, 200, 500, 750, 1000, 1200 or more nucleotides, or over the full-length, to a frustulin nucleic acid (e.g., frustulin polynucleotides, as described herein, and frustulin polynucleotides that encode frustulin polypeptides, as described herein). Based on the knowledge of frustulin homologs, those of skill can readily determine residue positions that are more tolerant to substitution. For example, amino acid residues conserved amongst species are less tolerant of substitution or deletion. Similarly, amino acid residues that are not conserved amongst species are more tolerant of substitution or deletion, while retaining the function of the frustulin protein.

An "expression cassette" refers to a nucleic acid construct, which when introduced into a host cell, results in transcription and/or translation of a RNA or polypeptide, respectively.

The term "promoter" or "regulatory element" refers to a region or sequence determinants located upstream or downstream from the start of transcription that direct transcription. As used herein, a promoter includes necessary nucleic acid sequences near the start site of transcription, such as, in the case of a polymerase II type promoter, a TATA element. A promoter also optionally includes distal elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter) and a second nucleic acid sequence, such as a nucleic acid encoding an antigen, wherein the expression control sequence directs transcription of the nucleic acid corresponding to the second sequence. An "algae promoter" or "bacterial promoter" is a promoter capable of initiating transcription in algae and/or bacterial cells, respectively. Such a promoter is therefore active in a microalgae cell, e.g., a diatom host cell, but need not originate from that organism. It is understood that limited modifications can be made without destroying the biological function of a regulatory element and that such limited modifications can result in algal regulatory elements that have substantially equivalent or enhanced function as compared to a wild type algal regulatory element. These modifications can be deliberate, as through site-directed mutagenesis, or can be accidental such as through mutation in hosts harboring the regulatory element. All such modified nucleotide sequences are included in the definition of an algal regulatory element as long as the ability to confer expression in unicellular green algae is substantially retained.

BRIEF DESCRIPTION OF THE DRAWINGS

FIGS. 8A-D illustrate the nucleic acid sequence of plasmid vector pMHL_79 (SEQ ID NO:8). pMHL vector is a pBluescript vector that has had the FCP promoter and terminator from a diatom engineered into it as well as the eGFP gene and the Gateway B fragment for recombination-based insertion.

FIGS. 9A-D illustrate the nucleic acid sequence of plasmid vector pMHL_79+HSDR2 (SEQ ID NO:9). This plasmid comprises a nucleic acid sequence encoding the IbpA DR2 domain.

FIGS. 10A-D illustrate the nucleic acid sequence of plasmid vector pMHL_79+HSDR2 CO (SEQ ID NO:10). This plasmid comprises a nucleic acid sequence encoding the IbpA DR2 domain with codon bias for improved expression in a diatom host cell.

DETAILED DESCRIPTION

1. Introduction

Figure 1:
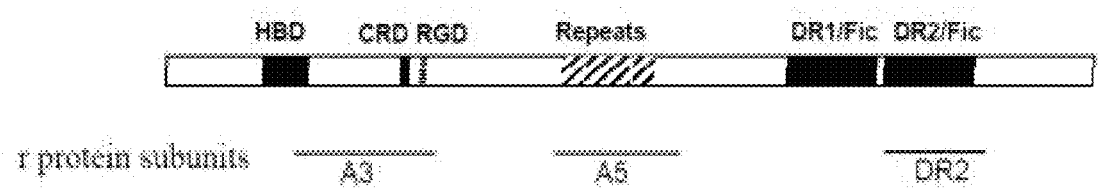
FIG. 1 illustrates IbpA protein diagram and vaccine antigen sites. Domains depicted: Heparin Binding Domain (HBD), Carbohydrate Recognition Domain (CRD), RGD motif, overlapping about 200 bp and 22 bp repeats (Repeats), and C-terminal Direct Repeat domains with Fic motifs (DR1/Fic and DR2/Fic). Recombinant protein subunits expressed, purified and used for vaccination (A3, A5 and DR2). rDR2 protected against H. somni septicemia in mice and pneumonia in cattle.

The present invention is based, in part, on the discovery that unicellular algae known as diatoms engineered to express antigens of pathogens (e.g., inside the cell or on their cell surface) able to induce protective immunity suitable for use as vaccines against such pathogens. Diatoms not only provide an antigen expression platform, but because their cell walls are made of nanostructured silica and associated frustule proteins and other macromolecules, they may act as an adjuvant. Diatoms replicate in natural or artificial sea water as well as fresh water, at generally ambient temperature with sunlight and require minimal nutrients, making inexpensive production feasible in underdeveloped countries. Diatoms can also be sonicated to form nanoparticles and/or lyophilized for long term storage. Ingestion of algae is safe and people are known to ingest >$10^{12}$ microparticles per day in normal living, including silica based particles. Mucosal or transdermal delivery of diatom-based vaccines provide an efficacious, effective, safe, low cost, stable vaccine delivery vehicle. The use of a mucosal or transdermal diatom surface display or cytoplasmic expression of antigens for immunization allows rapid, widespread, economical, refrigeration-free, and needleless vaccines to be deployed.

Diatom-based vaccines constitute a new, transformational idea because these unicellular algae, with biosilica cell walls, are easily grown in water at ambient temperatures, providing low cost in resource-limited settings. The vaccines are stable without refrigeration and can be lyophilized for dispensing oral vaccines in food or water. Diatom-based vaccines can be formulated as microparticles or nanoparticles, both of which are better at stimulating immune responses than soluble antigens. The biosilica cell wall may act as an adjuvant. By expressing an immunostimulatory adjuvant, e.g., Cholera Toxin B (CTB) subunit, *E. coli* heat labile toxin (LT) cytokines, TLR receptor agonists, or other protein adjuvants, or fragments thereof, in the cytoplasm, in the membrane system or on the surface of the diatom, adjuvant activity can be enhanced. Additionally, transmucosal antigen stimulation can be enhanced by the inclusion of specific domains of CTB or LT. Expression of protective, antigens in the cytoplasm, in the membrane system or on the surface of these stable, inexpensive particles results in efficacious mucosal vaccines. Diatom-based vaccines can also be used via other routes of administration.

Killed pathogen vaccines are expensive, require additional adjuvants, multiple doses and often have undesirable side effects. Alternatively, live modified or recombinant attenuated bacterial or virus vectored vaccines may revert to virulence, interfere with the normal flora or cause problems with environmental containment. Since diatoms are not pathogens, the problems with live bacteria or viruses do not apply. In contrast, diatom-based vaccines expressing an antigen are not expensive, carry endogenous adjuvants and are safe.

Microparticles and nanoparticles are better mucosal vaccine antigens than soluble proteins because particles are taken up by appropriate epithelial cells (e.g. M cells in the intestine) and stimulate antigen presenting cells (APCs) such as dendritic cells (DCs). Diatoms are microparticles (e.g., *Thalassiosira pseudonana* is 4×6 μm) but can also be tested as nanoparticles (<0.1 micron) after sonication. The biosilica cell wall of *T. pseudonana* is non-toxic, with a different chemical structure than fibrous silica which causes silicosis, and can also act as an adjuvant as has been shown for silica based immune stimulators. Others have shown that organic silica is a good adjuvant itself. Expression of an adjuvant antigen (e.g., Cholera Toxin B (CTB), *E. coli* heat labile toxin (LT), tetanus toxin (Tet)) on the diatom surface causes binding to ganglioside GM1 on the epithelial cell, and acts as an adjuvant. In preliminary experiments, we treated human peripheral blood mononuclear cells with *T. pseudonana*. Monocytes but not T cells were stimulated to produce large amounts of TNF alpha, indicating activation. Activated monocytes, macrophages and/or dendritic cells present antigens to T cells, thereby eliciting immune responses. Monocytes preferentially respond to particulate antigens, and attachment of proteins to a particulate improves immunogenicity to both CD4+ and CD8+ T-cells, as well as generating a broader T-cell cytokine response. Furthermore, TNFα expression is involved in the maturation of monocytes to a dendritic cell phenotype. Dendritic cells are extremely efficient at presenting antigen to T-cells at very low frequencies (1/1000).

Diatoms also have low intrinsic protease activity so the surface or cytoplasmically expressed proteins are stable. Nanoparticles are taken up better than microparticles and uptake of particulate adjuvants/antigens enhances immune responses. The diatom-based vaccines can be used as microparticles (whole diatoms) or nanoparticles after sonication (<0.1 microns).

2. Diatom-Based Vaccines

The diatom-based vaccines comprise a diatom comprising one or more antigens that are heterologous to the diatom. The one or more antigens can be in the cytoplasm of the diatom, in the cell membrane system (e.g., plasma membrane) or attached to the surface of the diatom. In various embodiments, the diatom is engineered to express the one or more antigens, e.g., in the cytoplasm, in the cell membrane system, or on the surface of the cell. In some embodiments, the one or more antigens are expressed as a fusion protein with a surface-expressed polypeptide endogenous to the diatom. In some embodiments, the surface-expressed polypeptide endogenous to the diatom is a frustulin polypeptide. In some embodiments, the antigen is expressed under the control of a promoter endogenous to the diatom. In some embodiments, the promoter endogenous to the diatom is selected from the group consisting of fucoxanthin chlorophyll binding protein (FCP) promoter and ribosomal protein L41 (rpL41) promoter.

In some embodiments, the diatom is a Bacillariophyta (e.g., Bacillariophyceae (Raphid, pennate diatoms), Coscinodiscophyceae (centric diatoms), Fragilariophyceae (Araphid, pennate diatoms) and/or Mediophyceae). In some embodiments, the diatom is a Coscinodiscophyceae (e.g., Chaetocerotophycidae, Corethrophycidae, Coscinodiscophycidae, Rhizosoleniophycidae, and/or Thalassiosirophycidae). In some embodiments, the diatom is a Thalassiosirophycidae. In some embodiments, the diatom is a Thalassiosirales. In some embodiments, the diatom is a Thalassiosiraceae. In some embodiments, the diatom is of the genus *Thalassiosira* (e.g., *Thalassiosira aestivalis, Thalassiosira allenii, Thalassiosira angulate, Thalassiosira anguste-lineata, Thalassiosira antarctica, Thalassiosira antarctica*-var. *borealis, Thalassiosira aff. antarctica, Thalassiosira concaviuscula, Thalassiosira curviseriata, Thalassiosira delicatula, Thalassiosira eccentric, Thalassiosira gessneri, Thalassiosira gravida, Thalassiosira guillardii, Thalassiosira hendeyi, Thalassiosira lundiana, Thalassiosira mala, Thalassiosira mediterranea, Thalassiosira minima, Thalassiosira minuscula, Thalassiosira nodulolineata, Thalassiosira nordenskioeldii, Thalassiosira oceanica, Thalassiosira pacifica, Thalassiosira profunda, Thalassiosira proschkinae, Thalassiosira pseudonana, Thalassiosira punctigera, Thalassiosira rotula, Thalassiosira tenera, Thalassiosira tumida, Thalassiosira weissflogii, Thalassiosira* sp. 422A, *Thalassiosira* sp. B101, *Thalassiosira* sp. CC03-04, *Thalassiosira* sp. CCMP1064, *Thalassiosira* sp. CCMP1065, *Thalassiosira* sp. CCMP1093, *Thalassiosira* sp. CCMP1277, *Thalassiosira* sp. CCMP1281, *Thalassiosira* sp. CCMP1987, *Thalassiosira* sp. CCMP353, *Thalassiosira* sp. CCMP988, *Thalassiosira* sp. CCMP991, *Thalassiosira* sp. Cleve BA153110, *Thalassiosira* sp. DDZ-2010a, *Thalassiosira* sp. DITS301-08, *Thalassiosira* sp. MBTD-CMFRI-S033, *Thalassiosira* sp. MBTD-CMFRI-S069, and/or *Thalassiosira* sp. MBTD-CMFRI-S132. In some embodiments, the diatom is *Thalassiosira pseudonana*.

In some embodiments, the diatom or population of diatoms further comprise an adjuvant. The adjuvant can be in the cytoplasm or attached to the surface of the diatom. In some embodiments, the adjuvant is exogenous to the diatom, e.g., a bacterial toxin, a cytokine. In some embodiments, the bacterial toxin is selected from the group consisting of Cholera Toxin B (CTB), tetanus toxin (Tet), *E. coli* heat labile toxin (LT), and immunogenic fragments thereof. In varying embodiments, the adjuvant is an immunostimulatory cytokine, e.g., IL-1, IL-2, IL-5, IL-6, IL-12, IL-15, Flt3L, GM-CSF, MIP-1α, IFN-γ, and mixtures thereof. In varying embodiments, the adjuvant is a mixture of IL-5 and GM-CSF. Co-administration of GM-CSF and IL-5 with antigen enhances immune responses. See, e.g., Ma, et al., *Am J Reprod Immunol* (2012) PMID:22934542. In some embodiments, the adjuvant is a Toll-like receptor agonist, e.g., flagellin and/or Meningococcal outer membrane protein C (OMP C). TLR ligand-antigen conjugates activate enhanced immune responses. Recombinant flagellin and Meningococcal outer membrane protein C (OMP C) activate via TLR5 and TLR2, respectively. See, e.g., Fujita and Taguchi, *Ther Deliv.* (2012) 3(6):749-60; Lahiri, et al., *Vaccine* (2008) 26: 6777-6783. In some embodiments, the adjuvant is a Toll-like receptor agonist combined with one or more cytokines TLR ligands combined with one or more cytokines (e.g., IL-15) enhance immune responses. See, e.g., Berzofsky, *Vaccine* (2012) 30: 4323-4327. In some embodiments, the diatom comprises a nucleic acid encoding the adjuvant or fragment thereof, and expresses the adjuvant or fragment thereof. The adjuvant may be expressed in the cytoplasm, in the membrane system or on the surface of the diatom. In some embodiments, the antigen and the adjuvant are expressed as a fusion protein.

3. Antigens

Vaccine-preventable diseases in animal subjects, including humans, domesticated and agricultural mammals, fish, crustaceans, mollusks, fowl, can be prevented and/or mitigated by administration of an antigen known to elicit a protective immune response expressed in the cytoplasm, in the membrane system or on the surface of a diatom. The diatom-based vaccines comprise one or more antigens that induce an immune response in the subject, sufficient to protect against and/or counteract the disease or condition to be treated or prevented, e.g., an infectious disease (viral, bacterial, fungal, parasitic) or a cancer. Antigens useful to induce a protective immune response are known in the art and find use in the diatom-based vaccines, e.g., to prevent against contraction of an infectious disease, to treat infectious diseases by immunotherapy or to facilitate retraction or inhibition of progression of cancer. In various embodiments, the antigen is from a virus, a bacterium, a fungus or a parasite. In various embodiments, the antigen is a tumor-associated antigen. In some embodiments, the antigen is an immunostimulatory polypeptide or peptide.

In some embodiments, the antigen is a viral antigen (e.g., from influenza, varicella zoster, herpes, HIV, respiratory syncytial virus (RSV) (e.g., N, F and/or G proteins), papilloma, Hepatitis A, Hepatitis B, Hepatitis C), a bacterial antigen (e.g., from *Vibrio, Salmonella, Shigella, Campylobacter, Yersinia, Histophilus, Staphylococcus, Streptococcus, Legionella*), a fungal antigen (e.g., from *Cryptococcus, Candida*) or a parasitic antigen (e.g., from *Plasmodium, Trypanosoma, Giardia, Entomoeba, Trichomonas*). Vaccine-preventable diseases in humans with known antigens that can be delivered to a subject in a diatom-based vaccine include, e.g., Cholera, Diphtheria, *Haemophilus influenza* type B, Hepatitis A, Hepatitis B, Hepatitis C, Influenza, Japanese Encephalitis, Measles, Meningococcal infection, Mumps, Pertussis, Pneumococcal infection, Poliomyelitis, Rabies, Rubella, Smallpox, Tetanus, Typhoid, Varicella, and Yellow Fever.

Vaccines are available for 20 to 30 infectious diseases of cattle. Illustrative bovine diseases that can be prevented and/or mitigated by administration of an antigen known to elicit a protective immune response expressed in the cytoplasm, in the membrane system or on the surface of a diatom include without limitation Clostridial diseases (e.g., Blackleg, Malignant Edema, Black's Disease, Enterotoxemia and Redwater); Anthrax, respiratory diseases (e.g., IBR (Infectious Bovine Rhinotracheitis) (Rednose), PI3 (Parainfluenza-3), BVD (Bovine Virus Diarrhea), BRSV (Bovine Respiratory Syncytial Virus) (e.g., BRSV N, F or G proteins), *Pasteurella multocida, Manheimia haemolytica*, and *Haemophilus sommus* (aka, *Histophilus somni*)), reproductive diseases (e.g., IBR, BVD, Brucellosis (Bangs), Vibriosis (*Campylobacter*), Leptospirosis and Trichomoniasis), scours (e.g., Rota and Corona Virus), *E. coli* and Pinkeye (*Moraxella* spp).

In some embodiments, the antigen in the cytoplasm, in the membrane system or on the surface of the diatom elicits or induces a protective immune response in the mammal against a *Histophilus somni* infection. In some embodiments, the antigen comprises one or more epitopes of *H. somni* virulence factor Immunoglobulin Binding Protein A (IbpA). In some embodiments, the antigen comprises the IbpA DR2 domain. In varying embodiments, the antigen comprises the IbpA DR2 domain and IbpA5, e.g., expressed as separate antigens or as a fusion protein. See, e.g., Geertsema et al., *Vaccine* (2011) 28:4805-4812. In varying embodiments, the antigen comprises the IbpA DR2 domain and BRSV N protein, e.g., expressed as separate antigens or as a fusion protein. In varying embodiments, the antigen comprises the IbpA DR2 domain and one or more BRSV antigens selected from the group consisting of N protein, F protein and G protein.

In some embodiments, the antigen induces and/or elicits a protective immune response in the mammal against bovine respiratory syncytial virus (BRSV), parainfluenza-3 ($PI_3$), bovine viral diarrhea virus (BVDV) or bovine herpes virus 1 (BHV-1). In some embodiments, the antigen comprises the BRSV N, F and/or G proteins. In some embodiments, the antigen induces and/or elicits a protective immune response in the mammal against infection of a bacterium selected from the group consisting of *Mannheimia haemolytica, Pasteurella multocida, Mycoplasma bovis, Vibrio parahaemolyticus* and *Legionella pneumophila*.

Illustrative equine diseases that can be prevented and/or mitigated by administration of an antigen known to elicit a protective immune response expressed in the cytoplasm, in the membrane system or on the surface of a diatom include without limitation tetanus, Eastern/Western Equine Encephalomyelitis (EEE/WEE), rabies, West Nile Virus (WNV), anthrax, botulism, Equine Herpesvirus (EHV), Equine Viral Arteritis (EVA), Equine Influenza, Potomac Horse Fever (PHF), Rotavirus, Strangles, and *Streptococcus equi*.

Illustrative canine diseases that can be prevented and/or mitigated by administration of an antigen known to elicit a protective immune response expressed in the cytoplasm, in the membrane system or on the surface of a diatom include without limitation Canine Parvovirus, Canine Distemper, Canine Parainfluenza, Canine Adenovirus Type 2, Canine *Leptospira canicola, L. grippotyphosa, L. icterohaemorrhagiae, L. pomona* Bacterin, Canine Coronavirus, Measles, *Bordetella bronchiseptica, Porphyromonas denticanis-gulae-salivosa* (Canine periodontitis), and rabies.

Illustrative feline diseases that can be prevented and/or mitigated by administration of an antigen known to elicit a protective immune response expressed in the cytoplasm, in the membrane system or on the surface of a diatom include without limitation Feline Panleukopenia, Feline Rhinotracheitis, Feline Calicivirus, *Chlamydia psittaci* (*Chlamydophila felis*), Feline Leukemia, Feline infectious peritonitis, and rabies.

Illustrative poultry diseases that can be prevented and/or mitigated by administration of an antigen known to elicit a protective immune response expressed in the cytoplasm, in the membrane system or on the surface of a diatom include without limitation Infectious Bursal Disease (IBD), Newcastle Disease, Marek's Disease, Fowl Pox, Gumboro, Avian Influenza, Avian Encephalomyelitis, *Mycoplasma*, Infectious Coryza (serotypes A, B, C), Infectious Bronchits, Egg Drop Syndrome, and *Salmonella Enteritidis* (SE). Poultry vaccines can be delivered mucosally, e.g., in food or water, or by aerosol or systemically, e.g., subcutaneously, intramuscularly or into the egg (in ovo).

In some embodiments, the antigenic protein expressed in the cytoplasm, in the membrane system or on the surface of or with the diatom may be used in the aquaculture industry for oral/surface mucosal vaccination of marine animal or an aquaculture animal, e.g., fish, crustacean (e.g., shrimp), or mollusk (e.g., bivalve). See, e.g., Sommerset, et al., *Expert Rev. Vaccines*. (2005) 4(1):89-101. In such embodiments, the diatoms can be mixed into the water or food of the animal. For example, shrimp populations are susceptible to a number of viral diseases: infectious hypodermal and hematopoietic necrosis virus (IHHNV), yellow head virus (YHV), taura syndrome virus (TSV), infectious myonecrosis (IMN), and white spot syndrome virus (WSSV).

In varying embodiments, the antigen elicits and/or induces a protective immune response against white spot syndrome virus (WSSV). In varying embodiments, the WSSV antigen is one or both of VP19 and VP466 proteins. In varying embodiments, the VP19 protein comprises an amino acid sequence having at least 90% sequence identity, e.g., at least 91%, 92%, 93%, 94%, 95%, 96%, 97%, 98%, 99% or 100% sequence identity, to SEQ ID NO: 11. In varying embodiments, the VP19 protein is encoded by a nucleic acid sequence having at least 90% sequence identity, e.g., at least 91%, 92%, 93%, 94%, 95%, 96%, 97%, 98%, 99% or 100% sequence identity, to SEQ ID NO: 12. In varying embodiments, the VP466 protein comprises an amino acid sequence having at least 90% sequence identity, e.g., at least 91%, 92%, 93%, 94%, 95%, 96%, 97%, 98%, 99% or 100% sequence identity, to SEQ ID NO: 13. In varying embodiments, the VP466 protein is encoded by a nucleic acid sequence having at least 90% sequence identity, e.g., at least 91%, 92%, 93%, 94%, 95%, 96%, 97%, 98%, 99% or 100% sequence identity, to SEQ ID NO: 14. See, e.g., Ha, et al., *J Microbiol Biotechnol*. (2008) 18(5):964-7; Huang, et al., *Molecular & Cellular Proteomics* (2002) 1.3:223-231; and van Hulten, et al., *Journal of General Virology* (2002) 83:257-265.

Viral diseases affecting fish include infectious pancreatic necrosis (IPNV), pancreas disease (PDV), infectious salmon anemia (ISAV), infectious hematopoietic necrosis (VHSV), viral nervous necrosis, iridoviral disease (RSIV), channel catfish virus disease (CCV), spring viremia of carp (SVCV), grass carp hemorrhage disease (GCHDV). Bacterial pathogens to fish such as *Vibrio* spp., *Listonella anguillarum*, *Vibrio harveyi*, *Vibrio salmonicida*, *Moritella viscosa*, *Aeromonas salmonicida* subsp. *salmonicida*, *Aeromonas salmonicida*, *Yersinia ruckeri*, *Piscirickettsia salmonis*, *Flavobacterium branchiophilum*, *Flavobacterium psychrophilum*, *Edwardsiella ictaluri*, *Edwardsiella tarda*, *Renibacterium salmoninarum*, *Lactococcus garvieae*, *Photobacterium damsela* subspecies *piscicida*, *Streptococcus iniae*, *Streptococcus phocae*, *Piscirickettsia salmonis*, and *Flavobacterium columnare* may be targeted by immunization with antigenic display on the diatom surface. Moreover, there are many major parasitic pathogens in fish, for which no commercially available vaccines are currently available: *Paramoeba* spp. (Amoebic gill disease), *Cryptobia salmositica*, *Ichthyobodo* spp., *Ichthyophthirius multifilis* (White spot disease), *Cryptocaryon irritans*, *Trichondina* spp., *Tetramicra brevifilum*, *Pleistophora anguillarum*, *Nucleospora salmonis*, *Myxobolus cerebralis* (whirling disease), *Tetracapsula bryosalmonae* (proliferative kidney disease; PKD), *Kudoa thyrsites*, *Gyrodactylus* spp., *Dactylogyrus* spp., *Benedinia* spp., *Eubothrium* spp., *Lepeophtheirus salmonis*, *Caligus* spp. See, e.g., Ha, et al., *J Microbiol Biotechnol*. (2008) 18(5):964-7 and Sommerset, et al, *Expert Rev. Vaccines*. (2005) 4(1):89-101. As appropriate or desired, aquaculture vaccines can be delivered, e.g., in food and by immersion in water containing diatom expressed antigens.

In varying embodiments, the antigen elicits and/or induces a protective immune response against *Vibrio harveyi*. In varying embodiments, the *V. harveyi* antigen is one or more of VhhP2, $DegQ_{vh}$, Vh-HL1 and Vh-ompK proteins. In varying embodiments, the VhhP2 protein comprises an amino acid sequence having at least 90% sequence identity, e.g., at least 91%, 92%, 93%, 94%, 95%, 96%, 97%, 98%, 99% or 100% sequence identity, to SEQ ID NO: 15. In varying embodiments, the VhhP2 protein is encoded by a nucleic acid sequence having at least 90% sequence identity, e.g., at least 91%, 92%, 93%, 94%, 95%, 96%, 97%, 98%, 99% or 100% sequence identity, to SEQ ID NO: 16. In varying embodiments, the $DegQ_{vh}$ protein comprises an amino acid sequence having at least 90% sequence identity, e.g., at least 91%, 92%, 93%, 94%, 95%, 96%, 97%, 98%, 99% or 100% sequence identity, to SEQ ID NO: 17. In varying embodiments, the $DegQ_{vh}$ protein is encoded by a nucleic acid sequence having at least 90% sequence identity, e.g., at least 91%, 92%, 93%, 94%, 95%, 96%, 97%, 98%, 99% or 100% sequence identity, to SEQ ID NO: 18. In varying embodiments, the Vh-HL1 protein comprises an amino acid sequence having at least 90% sequence identity, e.g., at least 91%, 92%, 93%, 94%, 95%, 96%, 97%, 98%, 99% or 100% sequence identity, to SEQ ID NO: 19. In varying embodiments, the Vh-HL1 protein is encoded by a nucleic acid sequence having at least 90% sequence identity, e.g., at least 91%, 92%, 93%, 94%, 95%, 96%, 97%, 98%, 99% or 100% sequence identity, to SEQ ID NO: 20. In varying embodiments, the Vh-ompK protein comprises an amino acid sequence having at least 90% sequence identity, e.g., at least 91%, 92%, 93%, 94%, 95%, 96%, 97%, 98%, 99% or 100% sequence identity, to SEQ ID NO: 21. In varying embodiments, the Vh-ompK protein is encoded by a nucleic acid sequence having at least 90% sequence identity, e.g., at least 91%, 92%, 93%, 94%, 95%, 96%, 97%, 98%, 99% or 100% sequence identity, to SEQ ID NO: 22. See, e.g., Sun, et al., *Vaccine* (2009) 27:2733-2740; Mao, et al., *Aquaculture* (2011) 318:268-272; Zhu, et al., *Vaccine* (2006) 24:6046-6052; Zhang, et al., *Appl Environ Microbiol* (2008) 74:6254-62.

In some embodiments, the antigen in the cytoplasm, in the membrane system or on the surface of the diatom induces and/or elicits a protective immune response in the mammal against a *Vibrio cholera* infection. In some embodiments, the antigen comprises one or more epitopes of Cholera Toxin B (CTB) or Cholera Toxin A (CTA). In some embodiments, the antigen comprises one or more epitopes of *V. cholera* colonization factors TcpA, TcpF and CBP-A. In some embodiments, the antigen comprises a Tcp-A2-CTB chimera. In some embodiments, the antigen comprises CTB and TcpA, e.g., expressed separately or as a fusion protein. In some embodiments, the antigen comprises CTB and TcpF, e.g., expressed separately or as a fusion protein. In some embodiments, the antigen comprises toxin co-regulated pilus (TCP), TcpA, TcpF and the chitin binding product (CBP-A), e.g., expressed separately or as a fusion protein. In some embodiments, the antigen comprises a combination of the above *V. cholera* antigens. See, e.g., Price and Holmes, *PloS ONE* (2012) 7(8): e42434; Kundu, et al., *FEMS Immunol Med Microbiol* (2009) 56: 179-184; Muse, et al., *FEMS Immunol Med Microbiol* (2012) 66: 98-115.

In some embodiments, the antigen induces and/or elicits a protective immune response in the animal against an enteric pathogen (e.g., *Salmonella, Shigella, Campylobacter, Yersinia*). In some embodiments, the antigen induces and/or elicits a protective immune response in the animal against an infection of an enteric pathogen selected from the group consisting of *Salmonella* spp., *Yersinia enterocolitica, Shigella sonnei, Shigella flexneri, Campylobacter jejuni, Entamoeba histolytica*, and *Giardia*.

In various embodiments, the antigen in the cytoplasm, in the membrane system or on the surface of the diatom-based vaccine is a *Plasmodium* antigen. Numerous *Plasmodium* antigens are known and find use in a diatom-based vaccine that inhibits or prevents the transmission and/or continued life cycle of a *Plasmodium* parasite, and/or the progression of a *Plasmodium* parasitic infection. For example, antigens associate with the intra-mosquito stage (sexual stages), one can distinguish: antigen Pfg27, Pfs16, Pfs25, Pfs28, Pfs45/48 or Pfs230; for the intravascular (sporozoite) stage: antigen CSP-1, STARP, SALSA or SSP-2; for the intrahepatic stage: antigen LSA-1, EXP-1, LSA-3, STARP, SALSA or SSP-2; and for the intra-erythrocyte (merozoite) stage: antigen RAP-1, RAP-2, SERA-1, MSP-1, MSP-2, MSP-3, MSP-4, MSP-5, AMA-1, EMP-1, Pf35, Pf55 or EBA-175. *Plasmodium* polypeptides, including without limitation, CDPK4, HAP2, MAPK-2, MDV 1/Peg3, P47, P48/45, P230, PKG, AP2-0, DOZI, HMGP2, Nek-4, CelTOS, CDPK3, Chitinase, CTRP, IMC1b, MAOP, P25, P28, SOAP, Cap380, CSP, ECP1, IMC1a, LAP1/CCp3/SR, LAP2/CCp1, LAP3/CCp5, LAP4/CCp2, LAPS/FNPA, LAP6/CCp4, transglutaminase, CSP, CRMP1, CRMP2, MAEBL, TRAP, and UOS3/TREP/S6, and immunogenic fragments thereof, also find use.

In various embodiments, the antigen is selected from the group consisting of: pollen, hepatitis C virus (HCV) core, E1, E2 and NS2 proteins, antigens from *Plasmodium* species selected from the group consisting of *P. vivax, P. falciparum* circumsporozoite protein (CS), human *P. falciparum, P. vivax, P. ovalae*, and *P. malariae*, TRAP, MSP-1, MSP-2, MSP-3, MSP-4, MSP-5, AMA-1 RESA, SALSA, STARP, LSAT and LSA3, HIV-gp120/160 envelope glycoprotein, *streptococcus* surface protein antigen, influenza nucleoprotein, hemagglutinin-neuraminidase surface infection, TcpA pilin subunit, VP1 protein, LMCV nucleoprotein, *Leishmania major* surface glycoprotein (gp63), *Bordetella pertussis* surface protein, rabies virus G protein, *Streptococcus* M protein, Staphylococcal proteins, *Helicobacter pylori* proteins, Respiratory Syncytial virus (RSV) F or G proteins, Epstein Ban virus (EBV) gp340 or nucleoantigen 3A, hemagglutinin, *Borrelia burgdoferi* outer surface protein (Osp) A, *Mycobacterium tuberculosis* 38 kD lipoprotein or 30 kD protein (Ag85), 10 kD or 65 kD proteins, Varicella zoster virus IE62 and gpI, Rubella virus capsid protein, Hepatitis B virus pre S1 ag, Herpes simplex virus type 1 glycoprotein G or gp D or CP27, Murray valley encephalitis virus E glycoprotein, Hepatitis A virus VP1, polio virus capsid protein VP1, VP2 and VP3, *Chlamydia trachomatis* surface protein, Hepatitis B virus envelope Ag pre S2, Human rhinovirus (HRV) capsid, papillomavirus peptides from oncogene E6 and E7, *Listeria* surface protein, Varicella virus envelope protein, Vaccinia virus envelope protein, *Brucella* surface protein, Rotavirus, VP-3, VP-4, VP-5, VP-7 and VP-8, combination of one or more of the antigens.

In various embodiments, the antigen is a breast cancer antigen, a lung cancer antigen, a pancreatic cancer antigen, a colon cancer antigen, or a melanoma cancer antigen. Antigens that elicit antibodies in a subject that specifically bind to a tumor-associated antigen ("TAA") can be delivered to the subject using the diatom-based vaccines. Examples of known TAAs include without limitation, melanoma associated antigens (MAGE-1, MAGE-3, TRP-2, melanosomal membrane glycoprotein gp100, gp75 and MUC-1 (mucin-1) associated with melanoma); CEA (carcinoembryonic antigen) which can be associated, e.g., with ovarian, melanoma or colon cancers; folate receptor alpha expressed by ovarian carcinoma; free human chorionic gonadotropin beta (hCGβ) subunit expressed by many different tumors, including but not limited to myeloma; HER-2/neu associated with breast cancer; encephalomyelitis antigen HuD associated with small-cell lung cancer; tyrosine hydroxylase associated with neuroblastoma; prostate-specific antigen (PSA) associated with prostate cancer; CA125 associated with ovarian cancer; and the idiotypic determinants of a B cell lymphoma can generate tumor-specific immunity (attributed to idiotype-specific humoral immune response). Moreover, antigens of human T cell leukemia virus type 1 have been shown to induce specific CTL responses and antitumor immunity against the virus-induced human adult T cell leukemia (ATL). See, e.g., Haupt, et al., Experimental Biology and Medicine (2002) 227:227-237; Ohashi, et al., Journal of Virology (2000) 74(20):9610-9616.

Polynucleotides encoding one or more antigenic polypeptides, or immunogenic fragments thereof, can be altered for improved expression in diatom host cells, e.g., *Thalassiosira pseudonana*. For example, codons in the wild-type polynucleotides encoding one or more antigenic polypeptides rarely used by the diatom host cell can be replaced with a codon coding for the same or a similar amino acid residue that is more commonly used by the diatom host cell (e.g., employing diatom nuclear codon bias), thereby allowing for more efficient expression of the antigenic polypeptide and higher yields of the expressed antigenic polypeptide in the diatom host, in comparison to expression of the antigenic polypeptide from the wild-type polynucleotide. Methods for altering polynucleotides for improved expression in a diatom host cell, particularly in a *T. pseudonana* host cell, are known in the art and described in, e.g., Lioudmila, et al., *Journal of Phycology* (2000) 36(2):379-386.

In various embodiments, polynucleotide sequences encoding antigenic polypeptides can be improved for expression in a diatom host cell by changing codons that are not common in the diatom host cell (e.g., used less than about 20% of the time). For improved expression of polynucleotide sequences encoding antigenic polypeptides in *T. pseudonana* host cells, codons rare or not common to the nucleus of *T. pseudonana* in the native *T. pseudonana* nucleic acid sequences are reduced or eliminated. A representative codon table summarizing codon usage in the *T. pseudonana* nucleus is found on the internet at kazusa.or.jp/codon/cgi-bin/showcodon.cgi?species=35128. In various embodiments, preferred or more common codons for amino acid residues in *T. pseudonana* are as follows:

| Amino Acid Residue | Preferred codons for improved expression in diatoms |
|---|---|
| Ala | GCT, GCA, GCC |
| Arg | CGT |
| Asn | AAT, AAC |
| Asp | GAT |
| Cys | TGT, TGC |
| Gln | CAA, CAG |
| Glu | GAG |
| Gly | GGA |
| Ile | ATC, ATT |
| His | CAT, CAC |
| Leu | TTG, CTC |
| Lys | AAG |

-continued

| Amino Acid Residue | Preferred codons for improved expression in diatoms |
|---|---|
| Met | ATG |
| Phe | TTC |
| Pro | CCA, CCT |
| Ser | TCT |
| Thr | ACC, ACT |
| Trp | TGG |
| Tyr | TAC |
| Val | GTG, GTC, GTT |
| STOP | TAA, TAG, TGA |

In certain instances, less preferred or less common codons for expression in a diatom host cell can be included in a polynucleotide sequence encoding an antigenic polypeptide, for example, to avoid sequences of multiple or extended codon repeats, or extended sequences of reduced stability (e.g., extended A/T-rich sequences), or having a higher probability of secondary structure that could reduce or interfere with expression efficiency. In various embodiments, the polynucleotide sequence can be synthetically prepared. For example, the desired amino acid sequence of a known antigenic polypeptide, or fragment thereof, desired to be expressed in a diatom host cell can be entered into a software program with algorithms for determining codon usage for a diatom host cell. Illustrative software includes GeneDesigner available from DNA 2.0, on the internet at dna20.com/genedesigner2 and Reverse Translate (on the internet at bioinformatics.org/sms2/rev_trans).

4. Methods of Promoting an Immune Response

Diatom-based vaccines can be administered to a subject to induce a protective immune response against a disease or condition (e.g., an infectious disease or cancer) which the subject is at risk of developing, or which may progress in the subject.

The pharmaceutical compositions comprising diatom-based vaccines can be formulated for parenteral, topical, oral, mucosal, transdermal, intrapulmonary, systemic or local administration. In various embodiments, the pharmaceutical compositions are administered parenterally, e.g., transdermally, intravenously, subcutaneously, intradermally, or into the egg (in ovo), or intramuscularly. In some embodiments, the diatom based vaccines are administered mucosally (e.g., orally, intranasally, conjunctivally, intrarectally or intravaginally). In some embodiments, the diatom-based vaccines are delivered in the food and/or water of the animal or by aerosol. Thus, the invention provides compositions for parenteral administration that comprise the diatoms described above suspended in an acceptable carrier, preferably an aqueous carrier. A variety of aqueous carriers may be used, e.g., phosphate buffered saline, water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient and more preferably at a concentration of 25%-75%.

For aerosol and/or intrapulmonary administration, the diatom-based vaccines are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery.

In some therapeutic applications, diatom-based vaccines are administered to a patient in an amount sufficient to induce and immune response and to prevent, reduce, inhibit, ameliorate, mitigate or reverse disease symptoms. An amount adequate to accomplish this is defined as a "therapeutically effective dose." Amounts effective for this use will depend on, e.g., the particular polypeptide, the manner of administration, the weight and general state of health of the patient, and the judgment of the prescribing physician.

The vaccines of the invention contain as an active ingredient an immunogenically effective amount of the diatom-based vaccine, as described herein. Useful carriers are well known in the art, and include, e.g., thyroglobulin, albumins such as human serum albumin, Cholera Toxin B (CTB), tetanus toxin (Tet), *E. coli* heat-labile toxin (LT) and immunogenic fragments thereof, polyamino acids such as poly(D-lysine:D-glutamic acid), influenza, hepatitis B virus core protein, hepatitis B virus recombinant vaccine and the like. The vaccines can also contain a physiologically tolerable (acceptable) diluent such as water, phosphate buffered saline, or saline, and further typically include an adjuvant. Adjuvants such as incomplete Freund's adjuvant, aluminum phosphate, aluminum hydroxide, saponins, or alum are materials well known in the art.

Vaccine compositions containing the polypeptides or nucleic acids described herein are administered to a patient to elicit a protective (e.g., that prevents or treats a disease in the animal) immune response against the antigen and thus prevent development and/or spread of the disease. Such an amount is defined as an "immunogenically effective dose." In this use, the precise amounts again depend on the patient's state of health and weight, the mode of administration, and the nature of the formulation.

5. Expression Cassettes and Recombinant Vectors

To use isolated sequences in the above techniques, recombinant DNA vectors suitable for transformation of microalgae, e.g., diatom host cells, are prepared. Techniques for transformation are well known and described in the technical and scientific literature. For example, a DNA sequence encoding an antigen can be combined with transcriptional and other regulatory sequences which will direct the transcription of the sequence from the gene in the intended cells of the transformed diatom host cells. In some embodiments, an expression vector that comprises an expression cassette that comprises the nucleic acid encoding the antigen or antigens of interest further comprises a promoter operably linked to the nucleic acid encoding the antigen. In other embodiments, a promoter and/or other regulatory elements that direct transcription of the nucleic acid encoding the antigen or antigens of interest are endogenous to the diatom and the expression cassette comprising the nucleic acid encoding the antigen or antigens of interest is introduced, e.g., by homologous recombination, such that the heterologous nucleic acid encoding the antigen or antigens of interest is operably linked to an endogenous promoter and is expression driven by the endogenous promoter.

Regulatory sequences include promoters, which may be either constitutive or inducible. In some embodiments, a promoter can be used to direct expression of the nucleic acid encoding the antigen or antigens of interest under the influence of changing environmental conditions. Examples of environmental conditions that may affect transcription by inducible promoters include anaerobic conditions, elevated temperature, or the presence of light. Promoters that are inducible upon exposure to chemicals reagents are also used to express the nucleic acid encoding the antigen or antigens of interest. Other useful inducible regulatory elements include copper-inducible regulatory elements (Mett et al., Proc. Natl. Acad. Sci. USA 90:4567-4571 (1993); Furst et al., Cell 55:705-717 (1988)); tetracycline and chlor-tetracycline-inducible regulatory elements (Gatz et al., Plant J. 2:397-404 (1992); Roder et al., Mol. Gen. Genet. 243:32-38 (1994); Gatz, Meth. Cell Biol. 50:411-424 (1995)); ecdysone inducible regulatory elements (Christopherson et al., Proc. Natl. Acad. Sci. USA 89:6314-6318 (1992); Kreutzweiser et al., Ecotoxicol. Environ. Safety 28:14-24 (1994)); heat shock inducible regulatory elements (Takahashi et al., Plant Physiol. 99:383-390 (1992); Yabe et al., Plant Cell Physiol. 35:1207-1219 (1994); Ueda et al., Mol. Gen. Genet. 250:533-539 (1996)); and lac operon elements, which are used in combination with a constitutively expressed lac repressor to confer, for example, IPTG-inducible expression (Wilde et al., EMBO J. 11:1251-1259 (1992)). An inducible regulatory element also can be, for example, a nitrate-inducible promoter, e.g., derived from the spinach nitrite reductase gene (Back et al., Plant Mol. Biol. 17:9 (1991)), or a light-inducible promoter, such as that associated with the small subunit of RuBP carboxylase or the LHCP gene families (Feinbaum et al., Mol. Gen. Genet. 226:449 (1991); Lam and Chua, Science 248:471 (1990)), or a light.

In one example, a promoter sequence that is responsive to light may be used to drive expression of a nucleic acid encoding the antigen or antigens of interest (e.g., Hahn, Curr Genet. 34:459-66, 1999; Loppes, Plant Mol Biol 45:215-27, 2001; Villand, Biochem J 327:51-7), 1997. Other light-inducible promoter systems may also be used, such as the phytochrome/PIF3 system (Shimizu-Sato, Nat Biotechnol 20): 1041-4, 2002). Further, a promoter can be used that is also responsive to heat can be employed to drive expression in algae such as Chlamydomonas (Muller, Gene 111:165-73, 1992; von Gromoff, Mol Cell Biol 9:3911-8, 1989). Additional promoters, e.g., for expression in algae such as green microalgae, include the RbcS2 and PsaD promoters (see, e.g., Stevens et al., Mol. Gen. Genet. 251: 23-30, 1996; Fischer & Rochaix, Mol Genet Genomics 265:888-94, 2001).

In some embodiments, the promoter may be from a gene associated with photosynthesis in the species to be transformed or another species. For example such a promoter from one species may be used to direct expression of a protein in transformed algal cells (e.g., diatom cells) or cells of another photosynthetic marine organism. Suitable promoters may be isolated from or synthesized based on known sequences from other diatoms and/or photosynthetic organisms. Preferred promoters are those for genes from other photosynthetic species that are homologous to the photosynthetic genes of the algal host to be transformed. For example, a series of light harvesting promoters from the fucoxanthin chlorophyll binding protein have been identified in *Phaeodactylum tricornutum* (see, e.g., Apt, et al. Mol. Gen. Genet. 252:572-579, 1996). In other embodiments, a carotenoid chlorophyll binding protein promoter, such as that of peridinin chlorophyll binding protein, can be used.

In some embodiments, a promoter used to drive expression of a heterologous nucleic acid encoding an antigen or antigens of interest is a constitutive promoter. Examples of constitutive strong promoters for use in microalgae include, e.g., the promoters of the atpA, atpB, and rbcL genes. Various promoters that are active in cyanobacteria are also known. These include promoters such as the (constitutive) promoter of the psbA3 gene in cyanobacteria and promoters such as those set forth in U.S. Patent Application Publication No. 20020164706, which is incorporated by reference. Other promoters that are operative in plants, e.g., promoters derived from plant viruses, such as the CaMV35S promoters, can also be employed in algae (e.g., diatoms).

A promoter can be evaluated, e.g., by testing the ability of the promoter to drive expression in plant cells, e.g., diatom host cells, in which it is desirable to introduce an expression construct that expresses an antigen or antigens of interest.

A vector comprising nucleic acid sequences that encode one or more antigens of interest will typically comprise a marker gene that confers a selectable phenotype on algae or bacterial cells. Such markers are known. For example, the marker may encode antibiotic resistance, such as resistance to kanamycin, G418, bleomycin, hygromycin, and the like. In some embodiments, selectable markers for use in *Chlamydomonas* can be markers that provide spectinomycin resistance (Fargo, Mol Cell Biol 19:6980-90, 1999), kanamycin and amikacin resistance (Bateman, Mol-Gen Genet. 263:404-10, 2000), zeomycin and phleomycin resistance (Stevens, Mol Gen Genet. 251:23-30, 1996), and paromomycin and neomycin resistance (Sizova, Gene 277:221-9, 2001).

Nucleic acid sequences encoding one or more antigens of interest are expressed recombinantly in diatom host cells. As appreciated by one of skill in the art, expression constructs can be designed taking into account such properties as codon usage frequencies of the organism in which the nucleic acid encoding the one or more antigens of interest is to be expressed. Codon usage frequencies can be tabulated using known methods (see, e.g., Nakamura et al. Nucl. Acids Res. 28:292, 2000). Codon usage frequency tables, including those for diatoms, are also available in the art (e.g., in codon usage databases of the Department of Plant Genome Research, Kazusa DNA Research Institute (on the internet at kazusa.or.jp/codon).

Cell transformation methods and selectable markers for bacteria and cyanobacteria are well known in the art (Wirth, Mol Gen Genet. 1989 March; 216(1):175-7; Koksharova, Appl Microbiol Biotechnol 2002 February; 58(2):123-37; Thelwell). Transformation methods and selectable markers for use in bacteria, also useful in diatom host cells, are well known (see, e.g., Green and Sambrook, Molecular Cloning: A Laboratory Manual, Cold Spring Harbor Laboratory Press; 4th edition (2012)).

6. Methods of Expressing Antigenic Polypeptides in Diatoms

The polynucleotides encoding antigenic polypeptides, and immunogenic fragments thereof, are expressed in and produced from a diatom host cell, e.g., a diatom that is a Bacillariophyta (e.g., Bacillariophyceae (Raphid, pennate diatoms), Coscinodiscophyceae (centric diatoms), Fragilariophyceae (Araphid, pennate diatoms) and/or Mediophyceae). In some embodiments, the diatom is a Thalassiosirophycidae. In some embodiments, the diatom is a Thalassiosirales. In some embodiments, the diatom is a Thalassiosiraceae. In some embodiments, the diatom is of the genus *Thalassiosira* (e.g., *Thalassiosira pseudonana*). Further diatom species of use as host cells to express polynucleotides encoding antigenic polypeptides are discussed above and herein.

The nucleus of diatom host cells are transformed, e.g., by homologous recombination techniques, to contain and stably express one or more polynucleotides encoding one or more antigenic polypeptides or an immunogenic fragment thereof, as described herein, integrated into the nuclear genome.

Transformation of the nuclei of diatom host cells can be carried out according to techniques well known to those persons skilled in the art. Examples of such techniques include without limitation electroporation, particle bombardment, biolistic methods or gene gun.

Expression of the antigenic polypeptides in the diatom host cells can be detected using any method known in the art, e.g., including immunoassays (ELISA, Western Blot) and/or nucleic acid assays (RT-PCR). Sequences of expressed polypeptides can be confirmed using any method known in the art (e.g., mass spectrometry).

Antigenic polypeptides expressed in a diatom host cell are generally properly folded without performing denaturation and refolding. Recombinant expression of proteins from heterologous polynucleotides incorporated into the nuclear genome of a diatom host cell is known in the art and described in numerous publications, including, e.g., Poulsen, et al., *J Phycol* (2006) 42:1059-1065; Apt, et al., *Mol Gen Genet* (1996) 252:572-579, and Dunahay, et al., *J. Phycol*. (1995) 31:1004-1012.

7. Kits

In various embodiments, the invention provides kits comprising one or more diatom-based vaccines, as described herein. In varying embodiments, the kits comprise diatom host cells engineered to express one or more antigens of interest that are packaged in one or multiple unitary doses for administration as a vaccine (e.g., to induce a protective immune response upon administration). In varying embodiments, the diatom host cells may be formulated for administration by the routes described above, e.g., oral, intravenous, subcutaneous, mucosal. Depending on the desired route of delivery, the diatoms may be formulated in a liquid and packaged in a vial, in a pressurized container (e.g., for aerosolized and/or intrapulmonary delivery), freeze-dried, compressed into tablets and/or mixed into food.

EXAMPLES

The following examples are offered to illustrate, but not to limit the claimed invention.

Example 1

Diatom-Based Vaccines Against Bovine Respiratory Disease

The goal is to develop vaccines using diatoms (unicellular algae) to express protective antigens of pathogens. These diatom based mucosal (e.g. orally, sublingually, buccally, intranasally, intravaginally, intrarectally, conjunctivally, intrapulmonarily, by aerosol or transdermally) or systemic vaccines would provide low cost, stable vaccines against widespread infectious diseases.

Diatoms provide an expression platform and, because their cell walls are made of nanostructured silica, also act as an adjuvant (Lincopan, et al., *BMC Biotech* (2009) 9:5-24). Furthermore, as mucosal vaccines, they stimulate the common mucosal immune system to protect against bovine respiratory disease and may have broader applications to infections of other mucosal sites. Diatoms are attractive as vaccines because they replicate in natural or artificial sea water at generally ambient temperature with sunlight and minimal nutrients, making inexpensive production feasible. Because they are photosynthetic autotrophs, diatoms require little nutrient and can be grown on a large scale in artificial or filtered sea water at ambient temperatures. This, plus their stability, allows for inexpensive production of effective vaccines. They can also be lyophilized for long term storage and can be sonicated to produce fine particles and nanoparticles. Diatoms are in the microparticle size range (*T. pseudonana* is 4×6 microns) but could be converted to fine particles (2.5-0.1 microns) or even nanoparticles (<0.1 micron) after brief sonication or mechanical crushing. Microparticles, fine particles and nanoparticles are better mucosal vaccine antigens than soluble proteins because particles are taken up best by appropriate epithelial cells and are best at stimulating antigen presenting cells such as dendritic cells (Adair B M. "Nanoparticle vaccines against respiratory viruses." In Wiley Interdisciplinary Reviews: Nanomedicine and Nanobiotechnology. 1: 405-414, 2009; Foged, et al., *Intl J Pharmaceut* (2005) 298:315-322; Sharp, et al., *Proc Natl Acad Sci USA* (2009) 106:870-875). The biosilica cell wall of *T. pseudonana* is non-toxic, with a different chemical structure than fibrous silica which causes silicosis, and can also act as an adjuvant as has been shown for silica based immune stimulators (Lincopan, et al., *BMC Biotech* (2009) 9:5-24). Algae in general are completely safe for ingestion with no adverse effects and are used as food supplements because many algal cellular constituents are beneficial to health (Gantar and Svircev, *J Phycol* (2008) 44:260-268). Ingestion of algae in the microparticle range is safe since people are known to ingest other types of microparticles at $>10^{12}$ per day in normal living, including silica based particles (Powell, et al., *Br J Nutr* (2007) 98:S59-S63). Safety should not be an issue in cattle.

*Histophilus somni* infection is targeted in the present example because it is a significant cause of Bovine Respiratory Disease, a high priority economically important disease of U.S. livestock. Bovine respiratory disease is said to be "the most important cause of economic losses for the cattle backgrounding and feedlot industries (McVey, *An Hlth Res Rev* (2009) 10:165-167). The economic loss to the North American beef cattle industry was estimated to be greater than $500,000,000 per year (Miles, *An Hlth Res Rev* (2009) 10:101-103). Fulton reported BRD to be the leading cause of morbidity and mortality in feedlots (Fulton, *An Hlth Res Rev* (2009) 10:131-239). Earlier studies indicated that 75% of clinical diagnoses and 64% of necropsy diagnoses of feedlot cattle were respiratory tract disease (Jensen, et al., *J Am Vet Med Assoc* (1976) 169:500-506). Not only is BRD a very significant cause of mortality but it also greatly decreases the market value of surviving cattle (Smith, *An Hlth Res Rev* (2009) 10:105-108) and adds to infrastructure and labor costs (Jim, *An Hlth Res Rev* (2009) 10:109-110). There is also a great impact on the dairy industry, with BRD accounting for 22.5% of unweaned heifer mortality and 46.5% of weaned heifer mortality (Patrick, *An Hlth Res Rev* (2009) 10:111-112). We chose to express the *Histophilus somni* (Angen, *Int. J. Syst. Evol. Microbiol.* (2003) 53:1449-1456) (formerly *Haemophilus somnus*) surface subunit antigen IbpA DR2/Fic on the diatom surface and intracellularly, in order to test protection in experimental bovine respiratory disease. In a recent review, Miles indicated that it is time to "focus on the animal's response to the pathogens" of bovine respiratory disease (Miles, *An Hlth Res Rev* (2009) 10:101-103).

*Histophilus somni* is one etiologic agent of bovine respiratory disease which allows testing protection of diatom-expressed antigens against this and other infections of the bovine respiratory tract. We have defined the mechanism of virulence and protection due to *H. somni* IbpA DR2/Fic (Worby, et al., *Molec Cell* (2009) 34:93-103; Zekarias, *Infect Immun* (2010) 78:1850-1858) and have a reproducible bovine experimental model of *H. somni* pneumonia. Using this model in the natural host, we have demonstrated that immunization with the recombinant *H. somni* IbpA DR2 subunit protein protects calves against challenge with the virulent bacteria (Geertsema, et al., *Vaccine*. (2011) 29(29-30):4805-12). To investigate the mechanisms of protection, we expressed the recombinant protein and made antibodies. The Fic motif in IbpA DR2 was shown to cause retraction and rounding up of HeLa cells (Worby, et al., *Molec Cell* (2009) 34:93-103) and bovine respiratory epithelial cells (Zekarias, *Infect Immun* (2010) 78:1850-1858). Antibodies to IbpA DR2 neutralized cytotoxicity. We also showed that a mutant recombinant IbpA DR2 protein with the critical histidine replaced by alanine (DR2 H/A) was not toxic but did protect mice against *H. somni* septicemia in a preliminary study. Therefore, IbpA DR2 H/A is a toxoid of use to stimulate immunity against *H. somni*. The IbpA DR2 and IbpA DR2 H/A genes are available for cloning into diatoms and the antibodies are available for demonstrating surface expression of IbpA DR2 and DR2 H/A. The nucleic acid sequence and the deduced amino acid sequence of IbpA DR2 has been published, e.g., in Cole, et al., *J Gen Microbiol* (1993) 139:2135-2143.

Although *H. somni* is an important cause of BRD, the etiology of the BRD complex is multifactorial. The most prevalent viruses include bovine respiratory syncytial virus (BRSV), parainfluenza-3 ($PI_3$), bovine viral diarrhea virus (BVDV) and bovine herpes virus 1 (BHV-1) (Ellis, *An Hlth Res Rev* (2009) 10:149-153; Fulton, et al., *An Hlth Res Rev* (2009) 10:131-239). Prevalent bacteria include *H. somni*, *Mannheimia haemolytica*, *Pasteurella multocida* and *Mycoplasma bovis* (Confer, *An Hlth Res Rev* (2009) 10:145-148; Fulton, et al., *An Hlth Res Rev* (2009) 10:131-239). Stress is another critical factor, which may be due to weaning, shipping, sudden changes in weather, social restructuring, novel feedstuff or handling, humidity, ventilation, dust etc. (Snowder, *An Hlth Res Rev* (2009) 10:117-119). Host response is also critical in pathogenesis and protection in BRD (Czuprynski, *An Hlth Res Rev* (2009) 10:141-143). We have studied bacterial/viral synergy in BRD (Berghaus, et al., *Vaccine* (2006) 24:6018-6027; Corbeil, et al., *Vet Immunol Immunopathol* (2006) 113:191-199; Gershwin, et al., *Vet Immunol Immunopathol* (2005) 107:119-130) but this proposal will focus on protection against *H. somni* pneumonia in order to devise means of intervention to prevent or control BRD.

*Histophilus somni* is a prevalent cause of bovine pneumonia but also causes septicemia, myocarditis, thrombotic meningoencephalitis, abortion and arthritis (Confer, *An Hlth Res Rev* (2009) 10:145-148; Corbeil, *An Hlth Res Rev* (2008) 8:151-160; Gogolewski et al., *Vet Pathol* (1987) 24:250-256; Harris, et al., *Can. Vet. J.* (1989) 30:816-822; Humphrey, et al., *Am. J. Vet. Res*. (1982) 43:791-795; O'Toole, et al., *Vet Pathol* (2009) 46:1015-1017; Sandal, et al., *Microbes Infect* (2009) 11:254-263; Sandal, et al., *Trends in Microbiol* (2010) 18:90-99; Widders, et al., *Infect Immun* (1986) 54:555-560), as well as disease in domestic sheep, bighorn sheep and bison (Diaz-Aparicio, et al., *Can J Vet Res* (2009) 73:157-160; Dyer, *J Vet Diagn Invest* (2001) 13:419-421; Lees, et al., *Can J Vet Res* (1994) 58:202-210; Tanaka, et al., *J Vet Med Sci* (2005) 67:255-262; Ward, et al., *Can J Vet Res* (1995) 59:173-178; Ward, et al., *Can J Vet Res* (1999) 63:166-169; Ward, et al., *Can J Vet Res*. (2006) 70:34-42). Asymptomatic genital or respiratory carriers are also common (Corbeil, *An Hlth Res Rev* (2008) 8:151-160; Humphrey, et al., *Am. J. Vet. Res*. (1982) 43:791-795). We have developed bovine and mouse models for *H. somni* induced BRD, bovine abortion and septicemia (Geertsema, et al., *Microbial Pathog* (2007) 42:22-28; Geertsema, et al., *Vaccine* (2008) 26:4506-4512; Geertsema, et al., *Vaccine*. (2011) 29(29-30):4805-12; Gogolewski, et al., *Vet Pathol* (1987) 24:250 256; Gogolewski, et al., *Infect Immun* (1987) 55:1403-1411; Gogolewski, et al., *Infect Immun* (1988) 56:2307-2316; Gogolewski, et al., *J Clin Microbiol* (1989) 27:1767-1774; Widders, et al., *Infect Immun* (1986) 54:555-560; Widders, et al., *Res Vet Sci* (1989) 46:212-217). The bovine studies defined isotypic antibody responses to *H. somni* (Gogolewski, et al., *J Clin Microbiol* (1989) 27:1767-1774; Widders, et al., *Infect Immun* (1986) 54:555-560; Widders, et al., *Res Vet Sci* (1989) 46:212-217; Yarnall, et al., *Scand J Immunol* (1988) 28:129 137) and specificity of antibodies for various *H. somni* antigens (Corbeil, et al., *Infect Immun* (1987) 55:1381-1386; Corbeil, et al., *Infect Immun* (1991) 59:4295-4301; Gogolewski, et al., *Infect Immun* (1987) 55:1403-1411; Yarnall, et al., *J Clin Microbiol* (1989) 27:111 117). Passive immunization studies showed that antibody to a 40K outer membrane protein (OMP) antigen was protective and the antigen was conserved (Corbeil, et al., *Infect Immun* (1991) 59:4295-4301; Gogolewski, et al., *Infect Immun* (1988) 56:2307 2316). IgG2 antibodies were most protective (Corbeil, et al., *Can J Vet Res* (1997) 61:207-213). Other virulence factors (or antigens) of *H. somni* have been shown to undergo antigenic or phase variation, so are not good vaccine candidates (Ekins, et al., *J Bacteriol* (2004) 186:4407-4411; Inzana, et al., *Infect Immun* (1992) 60:2943-2951; Inzana, et al., *Infect Immun* (1997) 65:4675-4681; Tagawa, et al., *Veterinary Microbiol* (2000) 71:245-254; Tremblay, et al., *Vet Microbiol* (2006) 114:104-114). In the course of these studies of *H. somni* host-parasite relationships, we discovered a surface immunoglobulin binding protein (IgBP, later called IbpA) which consisted of a surface fibrillar network (Cole, et al., *Molec Microbiol* (1992) 6:1895-1902; Corbeil, et al., *Infect Immun* (1997) 65:4250-4257; Widders, et al., *J Med Micro* (1988) 26:307-311; Widders, et al., *Infect Immun* (1989) 57:639 642; Yarnall, et al., *Scand J Immunol* (1988) 28:129 137; Yarnall, et al., *J Gen Microbiol* (1988) 134:1993-1999; Yarnall, et al., *J Clin Microbiol* (1989) 27:111-117). We have since developed methods for genetic exchange in *H. somni* (Sanders, et al., *FEMS Microbiol Letters* (1997) 154:251-258), made partial or complete IbpA deletions (Hoshinoo, et al., *Microb Pathog.* (2009) 46: 273-282; Sanders, et al., *Microbial Pathog.* (2003) 34:131-139), analyzed the genetic sequence of IbpA (Cole, et al., *J Gen Microbiol* (1993) 139:2135-2143; Tagawa, et al., *Microbial Pathog.* (2005) 39:159-170) and shown that four serum sensitive strains of *H. somni* from asymptomatic carriers lack the whole IbpA ORF (Cole, et al., *Molec Microbiol* (1992) 6:1895-1902). This correlation of IbpA with serum resistance was also detected by IgG2 Fc binding studies (Widders, et al., Infect Immun (1989) 57:639 642). IbpA deletion studies showed that IbpA was toxic for murine and bovine macrophages with inhibition of phagocytosis and disruption of actin filaments (Hoshinoo, et al., Microb Pathog. (2009) 46: 273-282). The sequence of IbpA revealed many putative functional domains, including adhesion domains or motifs in the N-terminal region (HBD, CRD and RGD) (FIG. 1). Three domains (A3, A5 and DR2) were expressed in E. coli, purified and used for vaccine studies in mice and calves (Geertsema, et al., Vaccine (2008) 26:4506-4512; Geertsema, et al., Vaccine (2011) 28: 4805-481). IbpA DR2 protected both mice (Geertsema, et al., Vaccine (2008) 26:4506-4512) and calves (Geertsema, et al., Vaccine (2011) 28: 4805-481). We recently reported that cytotoxicity to HeLa cells is due to the Fic motif in the DR1 and DR2 domains of IbpA (Worby, et al., Molec Cell (2009) 34:93-103).

Figure 2:
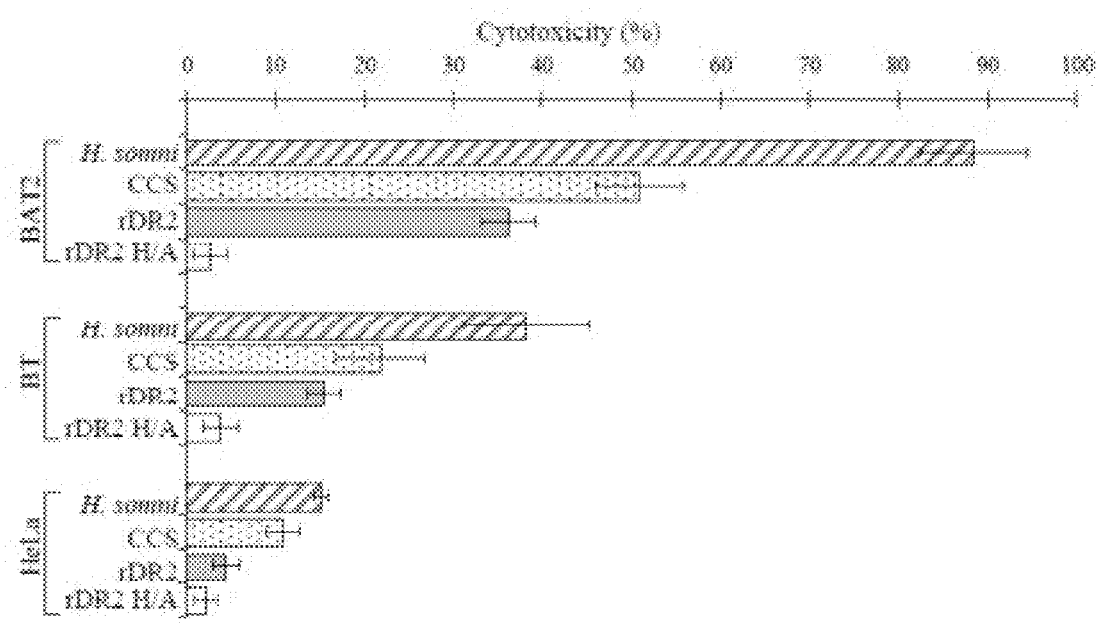
FIG. 2 illustrates cytotoxicity (cell retraction or rounding) of H. somni 2336 (100 MOI), 20× concentrated culture supernatant (CCS) and recombinant DR2 protein (rDR2) or H496A mutant rDR2 H/A (20 µg/ml each) on Bovine Alveolar Type 2 (BAT2), Bovine Turbinate (BT) and HeLa cells, expressed as % of cells with cytotoxic changes. H. somni causes bovine pneumonia and is mainly found in the lung alveoli, BAT2 bovine target cells are the main target in vivo and are much more susceptible to rDR2 than bovine upper respiratory BT cells or human HeLa cervical carcinoma cells. rDR2 H/A is essentially non-toxic.

We showed that the Fic motif inactivates RhoGTPases by adenylylation (also called ampylation) resulting in disruption of actin filaments and cell rounding or retraction (Worby, et al., Molec Cell (2009) 34:93-103). We then showed the bovine alveolar type 2 (BAT2) cells were more susceptible to H. somni and its IbpA enriched concentrated culture supernatant (CCS) toxicity than bovine turbinate (BT) cells (FIG. 2) (Zekarias, et al., Infect Immun (2010) 78:1850-1858). HeLa cells were least susceptible (Zekarias, et al., Infect Immun (2010) 78:1850-1858). In this case, cytotoxicity refers to retraction and rounding, not necessarily cell death. We could not detect markers of either apoptosis or autophagy. When cells were kept for 14 hours after the 4 hr treatment with H. somni or its CCS, the cells were still retracted but had not detached from the glass or plastic. The greater susceptibility of BAT2 cells was relevant to disease since H. somni is host specific for ruminants (Corbeil, An Hlth Res Rev (2008) 8:151-160; Harris, et al., Can. Vet. J. (1989) 30:816-822; Humphrey, et al., Am. J. Vet. Res. (1982) 43:791-795; Ward, et al., Can J Vet Res (1995) 59:173-178; Ward, et al., Can J Vet Res (1999) 63:166-169; Ward, et al., Can J Vet Res. (2006) 70:34-42) and is found primarily in the alveoli at necropsy in BRD (Bryson, et al., J. Comp. Pathol. (1990) 103:433-445; Gogolewski, Vet Pathol (1987) 24:250-256). Colonization of the upper respiratory tract, as modeled by BT cells, with less cytotoxicity may be relevant to the carrier state. The role of the Fic motif of IbpA DR2 in bovine disease was defined using a mutant recombinant DR2 protein with the critical histidine in Fic replaced by adenine (DR2 H/A). DR2/Fic protein caused retraction of BAT2 cells and DR2 H/A did not, confirming the role of the Fic motif (FIG. 2).

This finding was then extended by confocal microscopy showing that the IbpA DR2 was taken up into BAT2 cells even though live H. somni bacteria did not invade the cells (Zekarias, et al., Infect Immun (2010) 78:1850-1858). Therefore we investigated paracellular migration using BAT2 monolayers in Transwells. The results showed that IbpA DR2/Fic mediates crossing the alveolar barrier by causing BAT2 cells to retract, so that H. somni invades the bloodstream (Zekarias, et al., Infect Immun (2010) 78:1850-1858). Others have shown that the Fic motif is involved in pathogenicity of Vibrio parahaemolyticus (Yarbrough, et al., Science (2009) 323:269-272) and Legionella pneumophila (Roy, et al., Cell Biol (2009) 2:1-3). Since Fic motifs are found in the genomes of many bacterial pathogens, this is a new frontier in microbial pathogenesis (Kinch, et al., Plos ONE (2009) 4:1-9; Roy, et al., Cell Biol (2009) 2:1-3; Worby, et al., Molec Cell (2009) 34:93-103; Yarbrough, et al., Science (2009) 323:269-272; Zekarias, et al., Infect Immun (2010) 78:1850-1858). Antibody to rIbpA DR2 neutralized cytotoxicity and paracellular migration. The neutralization of DR2/Fic cell retraction parallels in vivo bovine and murine protective vaccination studies wherein IbpA DR2 vaccination protected (Geertsema, et al., Vaccine (2008) 26:4506-4512; Geertsema, et al., Vaccine (2011) 28: 4805-481).

After developing a method to reproducibly induce severe BRSV disease using aerosol infection with a clinical isolate (CA-1), studies were done to demonstrate that vaccination with formalin inactivated BRSV vaccine could induce vaccine exacerbated disease (Gershwin, et al., Vaccine (1998) 16:1225-36; Gershwin, et al., Am J Vet Res. (2000) 61:291-8; Gershwin, et al., Vet Immunol Immunopathol (2005) 107: 119-130; Woolums, et al., Am J Vet Res. (1999) 60(4):473-80; Woolums, et al., Vaccine. (1999) 17(11-12):1293-7). Both infection and vaccination with BRSV modulates immune responses towards a Th2 cytokine profile and induces IgE antibody formation (Gershwin, et al., Am J Vet Res. (2000) 61:291-8; Gershwin, et al., Vet Immunol Immunopathol (2005) 107:119-130; Kalina, et al., Vaccine (2004) 22:1465-72).

Gershwin and Corbeil have collaborated to investigate H. somni/BRSV synergism in calves (Berghaus, et al., Vaccine (2006) 24:6018-6027; Gershwin, et al., Vet Immunol Immunopathol (2005) 107:119-130). First it was shown that BRSV aerosol infection of calves 6 days before intrabronchial inoculation of H. somni resulted in a greater IgE response to H. somni as well as more severe pneumonia of longer duration. Then we found that the specificity of the IgE response in dual infection differed from the IgG response (Corbeil, et al., Vet Immunol Immunopathol (2006) 113:191-199). The IgE immunodominant H. somni antigen was the 41K major outer membrane protein (MOMP). IgG antibodies did not recognize the MOMP at the dilution used but reacted strongly to the 40K OMP (Corbeil, et al., Vet Immunol Immunopathol (2006) 113:191-199), which was previously shown to be protective (Gogolewski, et al., Infect Immun (1988) 56:2307 2316). Interestingly, the IgE antibodies which strongly reacted with the MOMP, did not react with the truncated, 33K MOMP in the IbpA negative strain 129Pt. This implied that this asymptomatic carrier strain may not stimulate a strong IgE response, since the dominant IgE epitopes were missing (Corbeil, et al., Vet Immunol Immunopathol (2006) 113:191-199). Since IgE responses to BRSV and H. somni are associated with increased pathology, lack of IgE stimulating epitopes may be advantageous (Gershwin, et al., Vaccine (1998) 16:1225-36; Gershwin, et al., Vet Immunol Immunopathol (2005) 107: 119-130; Kalina, Vaccine (2004) 22:1465-72; Ruby, et al., Vet Microbiol (2000) 76:373-383).

Figure 5:
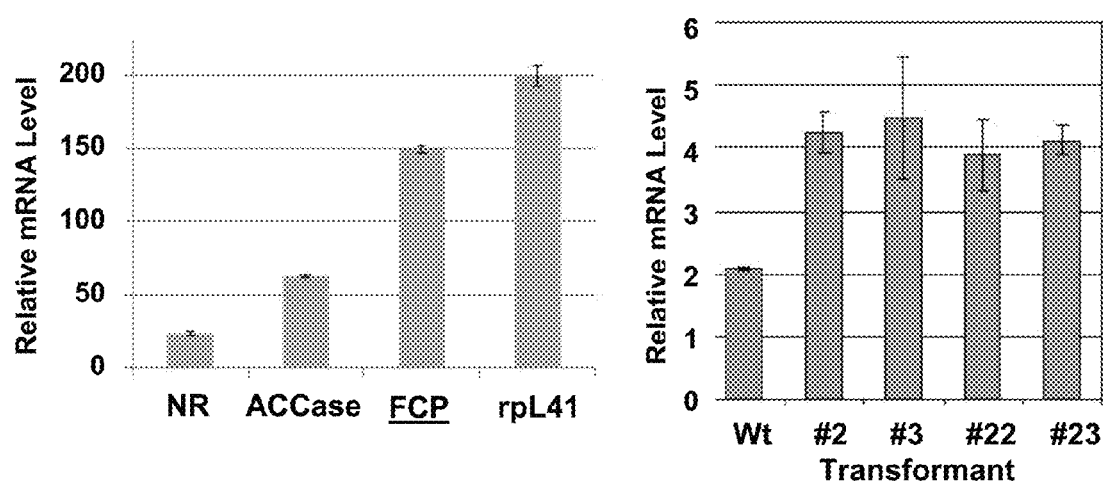
FIG. 5 illustrates mRNA accumulation control in T. pseudonana. Left, relative mRNA levels determined by qRT-PCR during exponential growth for four native genes in T. pseudonana, including nitrate reductase (NR), Acetyl CoA-carboxylase (ACCase), fucoxanthin chlorophyll binding protein (FCP), ribosomal protein L41 (rpL41). Right, mRNA levels for T. pseudonana transformants containing the glutathione acetyltransferase gene under control of FCP expression. Wild-type (Wt) is at the left, 4 transformants are shown to the right. Average expression level for the transformants relative to WT is twice as high.
Figure 6:
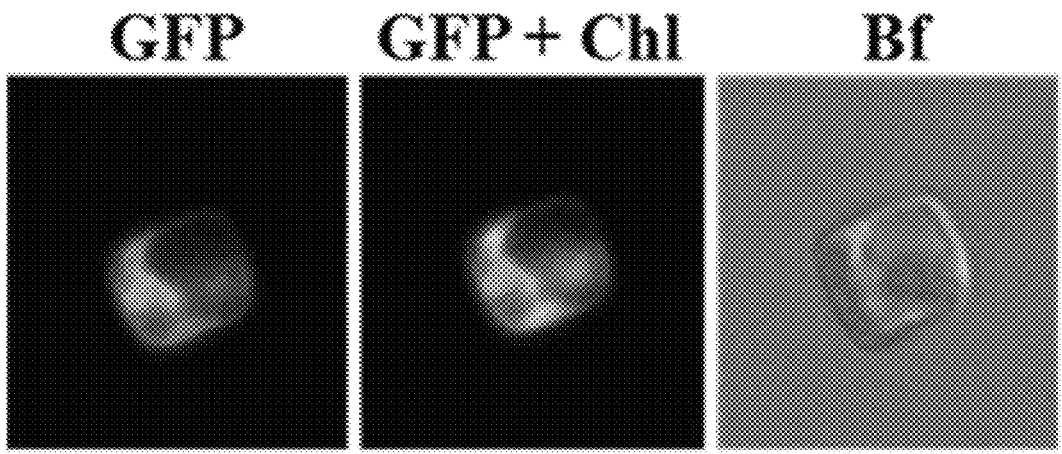
FIG. 6 illustrates cytoplasmic and plasma membrane expression, panels show GFP fluorescence (GFP), GFP plus chlorophyll (GFP+Chl), and brightfield (Bf).
Figure 6:
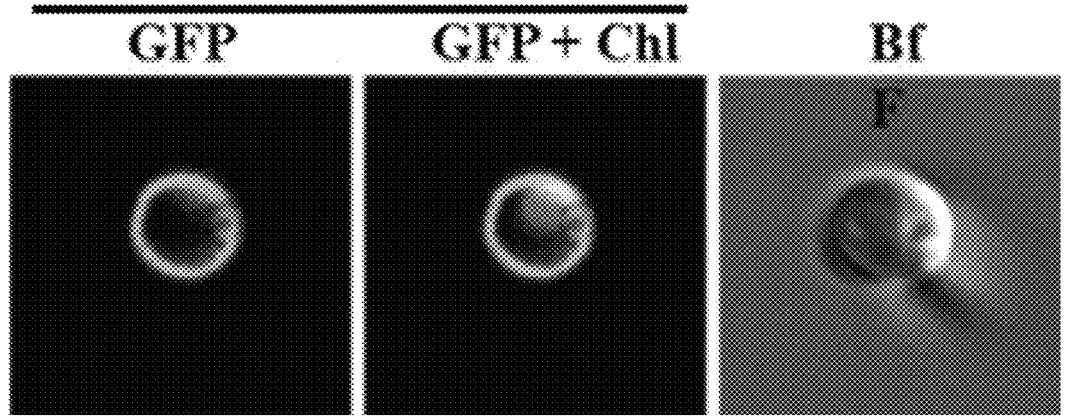
Figure 7:
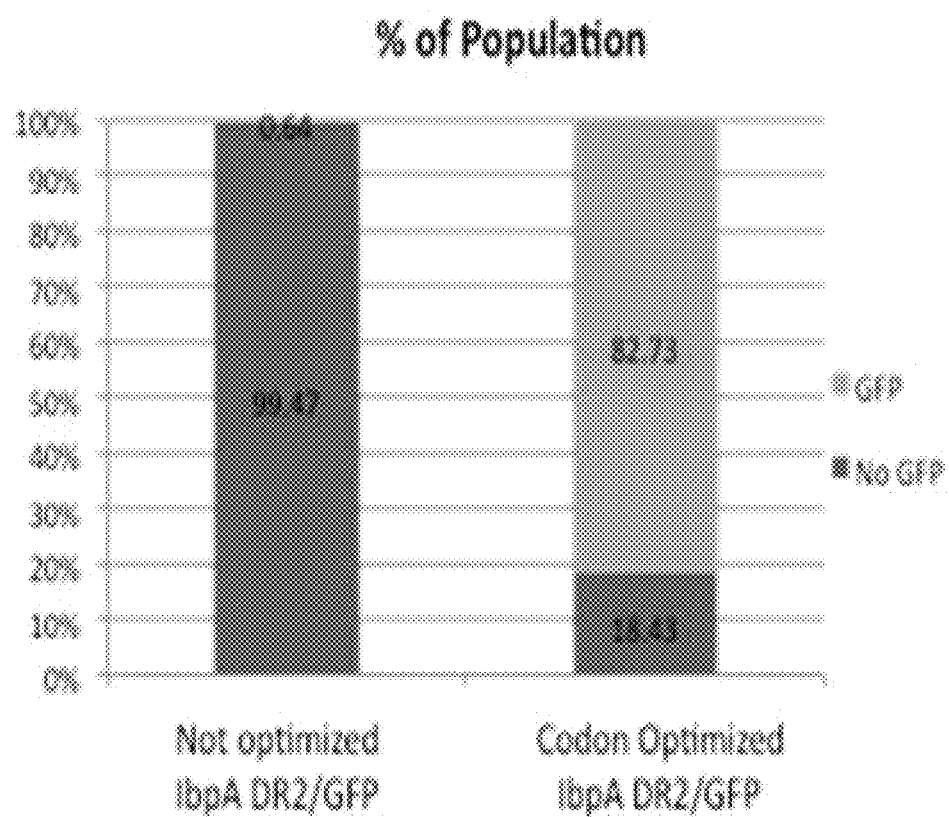
FIG. 7 illustrates a comparison of IbpA DR2/GFP expression in clonal, transformant populations performed with imaging flow cytometry. Data indicates that the percentage of T. pseudonana cells expressing GFP is dramatically increased when the IbpA DR2 domain is optimized for expression in T. pseudonana.

Of relevance to this study is the characterization of diatom cell wall proteins via proteomics (Frigeri, et al., Mol Cell Proteomics (2006) 5:182-193), and the biochemical and molecular characterization of a specific cell surface protein called p150 that is associated with a specific substructure of the T. pseudonana cell wall at a particular period of growth (Davis, et al., J Phycol (2005) 41:577-589). This study included cell surface protein labeling and purification, protein sequence determination, antibody production, and assessment of its cell surface localization as a function of cell cycle stage using immuno-based fluorescence microscopy (Davis, et al., J Phycol (2005) 41:577-589). Another class of general cell wall coat proteins identified in diatoms are called frustulins, which are ubiquitous (found in all diatom species examined) (Fischer, et al., J Phycol (1999) 35(1):113-120; Kroger, et al., EMBO J (1994) 13(19):4676-4683; Kröger, et al., Euro J Biochem (1996) 239(2):259-264). Sequences responsible for targeting these proteins to the cell wall have been identified, and fluorescent labeling at the cell surface has been accomplished using GFP fusions (Fischer, et al., *J Phycol* (1999) 35(1):113-120; Kröger, et al., *Protist* (2000) 151 (3):263-273). Expression of the GFP foreign protein at the diatom cell surface demonstrates the ability needed to express *H. somni* recombinant IbpA DR2 and DR2 H/A at the surface.

1) Strain Variation of *H. somni* IbpA

IbpA causes BAT 2 cells to retract, permitting the virulent bacteria to cross the alveolar barrier, indicating that IbpA is an important virulence factor of *H. somni*. Also, vaccination with IbpA DR2 protein protected mice (Geertsema, et al., *Vaccine* (2008) 26:4506-4512) or calves (Geertsema, et al., *Vaccine* (2011) 28: 4805-4812 and below) against *H. somni* infection and antibody to IbpA DR2 protected bovine alveolar cells against cytotoxicity (Geertsema, et al., *Vaccine* (2011) 28: 4805-4812, Zekarias, et al., *Infect Immun* (2010) 78:1850-1858). These studies show that IbpA DR2 is a protective antigen. Therefore, presence of IbpA was evaluated in different strains in order to define whether antigenic conservation occurs (Zekarias, et al., *Vet Microbiol*, (2011) 149:177-185). We found that a minority of preputial carrier strains lacked IbpA but all other tested disease or carrier isolates were IbpA positive. The tested positive strains had either both IbpA DR1/Fic and IbpA DR2/Fic or only IbpA DR2/Fic by PCR. Cytotoxicity and sequence analysis of DR2/Fic from selected strains revealed conservation of sequence and function. In addition to previous immunization studies with IbpA DR2, passive protection of mice against *H. somni* septicemia with antibody to IbpA DR2/Fic indicated that the IbpA DR1/Fic and/or DR2/Fic domains are candidate vaccine antigens which should protect against many strains of *H. somni* (Zekarias, et al., *Vet Microbiol*, (2011) 149:177-185). Conservation of IbpA DR2/Fic in most carrier strains indicates that they may be virulent if introduced to susceptible animals at susceptible sites. Conservation of the IbpA DR2 antigen in all disease isolates tested is encouraging for development of protective vaccines with diatoms expressing IbpA DR2.

2) Vaccination of Calves with rIbpA DR2 Protects Against *H. somni* Induced Pneumonia.

We tested whether a bovine vaccine composed of IbpA recombinant subunits (see FIG. 1) would protect against challenge with virulent *H. somni*. To test this vaccine, healthy 5-6 week old calves were received from a nearby dairy and vaccinated twice with rIbpA3, rIbpAS, and rIbpA DR2 (200 micrograms/dose) or GST (negative control at 67 micrograms—amount of GST in 200 micrograms of fusion proteins), 5-6 calves per group. Two weeks later, calves were challenged intrabronchially with $5\times10^9$ *H. somni* strain 2336. Clinical signs were monitored and calves were necropsied at day 4 after challenge by a veterinary pathologist. Gross lung lesion volumes were estimated by a standardized protocol and samples were taken for bacterial culture and histopathology. Viral serology revealed no increases in titer throughout the experiment, indicating passive transfer of antibodies from the vaccinated dams rather than active infection of calves. Serum and bronchio-alveolar secretions were collected for assay of isotypic antibodies to the vaccine antigens. The DR2 immunized group had the lowest clinical scores. The volume of lesions (percentage of the lung at necropsy or "percent lesions") and bacterial cultures were the most revealing measures of protection (FIG. 3A). DR2 vaccinated animals had less pneumonic lung than the GST controls ($p<0.05$), even though variation within groups was rather great. No *H. somni* was cultured from lungs of DR2 vaccinated calves, which was also significantly different from the control group ($p<0.05$) (FIG. 3B).

Antibody studies with the subunit antigens confirmed that the protection was related to specific antibodies. Both IgG1 and IgG2 antibody responses were detected and specific for the immunizing antigen in each group. IgE antibody levels have been associated with adverse reactions and with worse clinical signs of longer duration in calves with *H. somni* pneumonia (Ellis, et al., *Can Vet J* (1997) 38:45-47; Gershwin, et al., *Vet Immunol Immunopathol* (2005) 107:119-130). Therefore, we measured IgE antibody levels in serum. Although all groups had IgE responses to *H. somni*, DR2 elicited the lowest IgE response, an indication of a good vaccine. Antibodies (IgG1, IgG2 and IgA) in lung lavage fluid collected at necropsy also had the highest ELISA readings when tested against the antigen used for immunization. These studies show that immunization of calves with rDR2 protects against *H. somni* induced bovine pneumonia. This protection is associated with specific serum IgG1 and IgG2 antibody responses and IgG1, IgG2 and IgA responses in bronchial secretions. Since rDR2 immunized calves had lowest IgE antibody levels, IgE mediated immunopathogenesis is least likely with DR2 immunization.

To access the mechanism of protection in this calf vaccine study, we determined whether sera from immunized protected calves neutralized the cytotoxicity of IbpA DR2 for BAT2 cells in culture. Untreated control cells or those treated with *H. somni* plus bovine convalescent phase serum or bovine antibodies to IbpA DR2 had significantly less ($P<0.01$) cell retraction than those treated with bacteria plus preimmune serum (FIG. 4).

3) Antibodies to IbpA Subunits A3, A5 and DR2 in Bovine Experimental *H. somni* Pneumonia.

Isotypic antibody levels in serum from earlier *H. somni* infection studies (29 calves in 3 different studies with experimental *H. somni* pneumonia without vaccination) were evaluated throughout the infection period to determine the kinetics of the IgG1 and IgG2 responses to recombinant IbpA subunits A3, A5, and DR2 as well as control whole cell and supernatant antigens. Calves responded to all antigens but backgrounds and kinetics differed. Backgrounds were highest with the control whole cell and culture supernatant antigens for both IgG1 and IgG2 responses. IgG2 antibody levels began to increase by wk 2 but were never as high as IgG1 responses, which began to increase at wk 1. Interestingly, there was no detectable IgG2 response to the DR2 antigen in convalescent calves. If an IgG2 response could be elicited with IbpA DR2 vaccination, better protection may result. Perhaps persistence of *H. somni* in the lung for weeks after the clinical stage of experimental pneumonia in our earlier studies (Gogolewski, et al., *J Clin Microbiol* (1989) 27:1767 1774) is due to the undetectable IgG2 antibodies to IbpA DR2.

4) *Vaccine* Studies with Purified IbpA DR2 and IbpA DR2 H/A in a Mouse Septicemia Model.

We previously developed a mouse septicemia model for *H. somni* infection because this organism causes septicemia in cattle (Geertsema, et al., *Microbial Pathog* (2007) 42:22-28; Geertsema, et al., *Vaccine* (2008) 26:4506-4512). Then we showed that vaccination of mice with purified recombinant IbpA DR2 protected against *H. somni* septicemia (Geertsema, et al., *Vaccine* (2008) 26:4506-4512). Since antibodies to IbpA DR2 reacted strongly with IbpA DR2 H/A, we hypothesized that this non-cytotoxic protein would serve as a toxoid vaccine. This was tested in the mouse model of *H. somni* septicemia. Preliminary data, with only 4 mice per group, indicates that IbpA DR2 H/A protects essentially as well as IbpA DR2. The bovine model is much more relevant to bovine respiratory disease, so we propose to test IbpA DR2 H/A as a toxoid vaccine in calves, in comparison with IbpA DR2, both expressed on the surface of diatoms.

With respect to the development of protein expression systems in diatoms, we have characterized mRNA accumulation from four different genes in *T. pseudonana* and can drive expression at different levels (FIG. 5, left). Genes with the highest levels of mRNA accumulation were the FCP (fucoxanthin chlorophyll binding protein), and rpL41 (ribosomal protein L41) genes. To demonstrate the ability to overexpress genes, transgenic *T. pseudonana* were examined for overexpression of the glutathione acetyltransferase gene (GAT) using the FCP promoter, showing an average mRNA accumulation level in four different transformants of twice the wild-type level (FIG. 5, right), demonstrating over-expression. We have also constructed a series of Gateway™ vectors that enable rapid cloning of any gene of interest under the control of the previously described promoters.

Targeting of expressed proteins to three subcellular locations can be accomplished. Cytoplasmic expression has the potential advantages of increased expression of protein (a larger volume than cell surface) and increased protein stability due less exposure to extracellular proteases (diatom intracellular protease activity is intrinsically low), because the diatom silica cell wall is an effective physical barrier against the breakdown of intracellular components by external agents. Cytoplasmic expression requires cell rupture to release the antigens, which could increase adjuvanticity by forming nanoparticles. Cell membrane expression, including the plasma membrane, might combine protection with availability to the outside, which could improve antigenicity. Cell surface expression has the advantage of immediate use of transgenic diatoms with no processing necessary. The choice of highly abundant cell surface proteins (Davis, et al., *J Phycol* (2005) 41:577-589; Fischer, et al., *J Phycol* (1999) 35(1):113-120; Kroger, et al., *EMBO J* (1994) 13(19):4676-4683; Kroger, et al., *Euro J Biochem* (1996) 239(2):259-264) to generate fusions should maximize surface protein yields. Expression of GFP in *T. pseudonana* in the cytoplasm and in the plasma membrane has been demonstrated (FIG. 6).

Subsequent efforts have focused on improving and increasing the expression. The IpbA DR2 domain was codon optimized for expression in *T. pseudonana* in silico with the program Reverse Translate (on the internet at bioinformatics.org/sms2/rev_trans.html), and a start codon was included at the beginning of the DR2 domain. Integrated DNA Technologies (IDT) synthesized the optimized gene, which was then cloned into pMHL_79 using the Gateway™-based cloning platform (Invitrogen). The diatom transformation vector pMHL_79 utilizes the *T. pseudonana* FCP promoter and terminator and contains GFP in frame with the desired insert for a C-terminal fusion. *T. pseudonana* was transformed with the IbpA DR2/GFP construct using the biolistic method. Transformants expressing GFP in the cytoplasm were isolated and imaged with fluorescence microscopy (FIG. 6) and imaging flow cytometry. Imaging flow cytometry provided statistical validation of observations made by fluorescence microscopy; specifically, a substantially larger percentage of a clonal population is observed to express the fusion protein when IbpA is codon optimized for expression in *T. pseudonana* (FIG. 7).

Expression of *H. somni* Antigens (IbpA DR2 and DR2 H/A) on the Surface and in the Cytoplasm of Diatoms.

We have expressed IbpA DR2 and DR2 H/A in *E. coli* (Geertsema, et al., *Vaccine* (2008) 26:4506-4512; Geertsema, et al., *Vaccine* (2011) 28: 4805-4812; Worby, et al., *Molec Cell* (2009) 34:93-103, Zekarias, et al., *Infect Immun* (2010) 78:1850-1858). Earlier, we expressed IbpA p76 (containing DR2—see FIG. 1) at the surface of *B. abortus* vaccine strain RB51. Now we have demonstrated intracellular expression of IbpA DR2 fused to GFP (FIG. 6) and have expressed rDR2 at the plasma membrane in *T. pseudonana* (FIG. 6).

Experimental Design and Methods a) Model antigen constructs. The primers for IbpA3, IbpA5 and IbpA DR2 antigen expression have been described, e.g., in Geertsema, et al., *Vaccine* (2011) 28: 4805-4812. Briefly, the IbpA DR2 and mutant DR2 (H/A) encoding region was PCR amplified using primer sequences (Forward: 5'-AGCTCCATGGGAAAATCAT CTCCGCAAGAG-3' (SEQ ID NO: 23); Reverse: 5'-AGCTGGATCCT-GATTTTTTTGCCAACTCTTTTAAA-3' (SEQ ID NO: 24)) and cloned into a GST-tag plasmid vector pET41a. Recombinant *H. somni* IbpA DR2/Fic expressed in *E. coli* BL21 cells was purified by glutathione-affinity chromatography. This rIbpA DR2 is used to quantitate bovine antibody responses by ELISA and the construct in *E. coli* is the source of the sequence for expression in *T. pseudonana*.

b) Constructs and expression in *T. pseudonana*. Initially the DR2 domain was fused to GFP and placed under the control of the rp141 promoter for cytoplasmic expression. A small percent of the clonal population demonstrated high levels of expression of this protein in the cytoplasm. To increase the percentage of cells expressing, the DR2 domain was codon optimized for expression in *T. pseudonana* in silico with the program Reverse Translate (on the internet at bioinformatics.org/sms2/rev_trans.html), and a start codon was included at the beginning of the DR2 domain. Integrated DNA Technologies (IDT) synthesized the optimized gene, which was then cloned into pMHL_79 using the Gateway™-based cloning platform (Invitrogen). The diatom transformation vector pMHL_79 utilizes the *T. pseudonana* FCP promoter and terminator and contains GFP in frame with the desired insert for a C-terminal fusion. *T. pseudonana* was transformed with the IbpA DR2/GFP construct using the biolistic method following established techniques (Poulsen, et al., *J Phycol* (2006) 42:1059-1065). Transformants expressing GFP in the cytoplasm were isolated (FIG. 6). A second construct was generated that fused the codon optimized DR2 domain to a plasma membrane targeted protein under the control of FCP. This fusion protein was successfully localized in the cell membrane of *T. pseudonana* (FIG. 6).

Regarding cell-surface localization, *T. pseudonana* encodes three frustulin genes. E-frustulin finds use because it is the smallest (489 amino acids). Although cell surface targeting sequences have been identified in the frustulins (Fischer, et al., *J Phycol* (1999) 35(1):113-120), domains on the frustulins that facilitate cell surface attachment have not been characterized. For this reason, in initial constructs, fusions to full-length ϵ-frustulin targeting genes are used, although truncated forms of ϵ-frustulin may also be employed. GFP fusion solely to ϵ-frustulin is included in the constructs for control experiments to enable determination of the rate of appearance and level of protein at the cell surface during the growth cycle to determine these basic parameters and optimal conditions for expression of the antigenic fusions. To reduce overall fusion protein size, GFP is not included in the antigenic fusions—in this case monitoring of cell surface expression is done by ELISA or IFA with antibodies to the antigen.

Optimization of Recombinant Diatom Antigens and Determination of Effect on Bovine Turbinate (BT) Plus Bovine Alveolar Type 2 (BAT2) Epithelial Cells In Vitro.

A) Optimization of Diatom Antigens:

Surface expressed IbpA DR2 or DR2 H/A frustulin fusion proteins can be measured by ELISA with antibodies to *H. somni* IbpA DR2.

Experimental Design and Methods Antigen expression is monitored by ELISA with anti-*H. somni* IbpA DR2 and recombinant diatoms (or sonicated samples) on the solid phase. Amount of antigen per diatom is determined by ELISA with calculations based on a standard curve of dilutions of known protein concentrations of purified recombinant IbpA DR2. This method has been developed in our lab and we have recombinant IbpA DR2. Western blotting will determine specificity and immunofluorescence will evaluate cell surface display.

B) Determination of Effect on Bovine Turbinate (BT) Plus Bovine Alveolar Type 2 (BAT2) Epithelial Cells In Vitro.

Both *H. somni* IbpA DR2 and DR2 H/A have been used in cytotoxicity studies with bovine turbinate (BT) cells and bovine alveolar type 2 (BAT2) epithelial cells (see FIG. 2). BT cells were less sensitive to retraction than BAT2 cells to IbpA DR2 (FIG. 2 and Zekarias, et al., *Infect Immun* (2010) 78:1850-1858) but IbpA DR2 H/A did not cause retraction or rounding (FIG. 2 and Zekarias, et al., *Infect Immun* (2010) 78:1850-1858). It is not clear whether retraction of bovine respiratory epithelial cells would be harmful or beneficial in vivo. We found that cells rounded up after 4 hours treatment in cell culture (Zekarias, et al., *Infect Immun* (2010) 78:1850-1858). However, if the cultures were incubated for 14 hours more, the cell did not die and fall off the plastic or glass. Transitory epithelial cell retraction may permit more antigen up-take and greater immune responses. These studies will provide background on the mechanisms of action of intact or sonicated recombinant antigen expressing or parent diatoms. The calf experiments provide some insight into the relevance of these epithelial cell studies for both pathogenicity and immune responses. Most of the diatom expressed antigen remain in the upper respiratory tract due to the size (4 by 6 microns) of *T. pseudonana*. Therefore, the effect of intact diatoms expressing IbpA DR2 on BT cells in vivo may be more relevant than on BAT2 cells. However, sonicated diatoms would include much smaller particles, in the range of 1 micron and below (which should reach the alveolus). Both intact diatoms and sonicated diatoms are tested in the epithelial cell studies.

Experimental Design and Methods

BT cells and BAT2 cells are treated (at confluency or near confluency) with 20 μg/ml each of positive control rIbpA DR2 or DR2 H/A in tissue culture media as was done in our previous studies (Zekarias, et al., *Infect Immun* (2010) 78:1850-1858 and FIG. 2 above). The quantity of diatoms expressing 20 μg/ml of DR2 or DR2 H/A is compared with the toxicity of the soluble recombinant proteins. Cells are fixed with 4% fresh paraformaldehyde and stained with Rhodamine phalloidin for actin fibers. Cytotoxicity is quantitated by counting retracted and rounded BT or BAT2 cells treated with tissue culture media, recombinant DR2 or DR2 H/A or diatoms expressing DR2 or DR2 H/A.

Determination of the Protective Immunity in a Bovine Model of *H. somni* Pneumonia by Vaccinating with Diatom Expressed Antigens.

Figure 3:
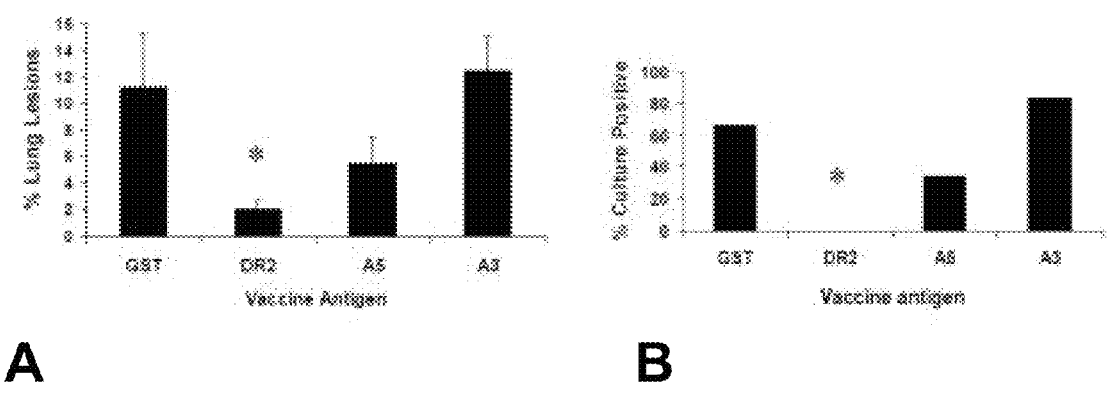
FIGS. 3A-B illustrate protection of calves against H. somni experimental pneumonia by vaccination. A) Volume of lung lesions expressed as % of lung with pneumonic lesions at necropsy (% lung lesions). NOTE: rDR2 vaccine protected best (p<0.05 compared with GST control). B). H. somni culture results from vaccinated calves. Again rDR2 protected best. *(<0.05).

We have shown that rIbpA DR2 subcutaneous vaccine protects calves against experimental *H. somni* pneumonia (FIG. 3). Antibodies from these calves reacts equally with reacts equally with rIbpADR2 H/A in Western blots. Since IbpA DR2 H/A has only one amino acid change in the Fic motif (Histidine replaced by Alanine) but is essentially non-toxic for BT and BAT2 cells, we propose that the mutant IbpA DR2 H/A will act like a toxoid to protect calves against *H. somni* pneumonia. The hypothesis was strengthened by a small preliminary mouse septicemia experiment which showed that vaccination with IbpA DR2 or with IbpA DR2 H/A both protected against septicemia. Since we will use the same dose of recombinant diatom expressed protein in the current vaccines as we used for the soluble recombinant vaccines in calves (FIG. 3), we propose that the diatom expressed vaccines should protect also. In fact, since these vaccines are particulate and have adjuvant-like biosilica in their cell walls, the diatom based vaccines may protect better than the recombinant soluble protein in our previous studies. Lastly, since *H. somni* pneumonia is caused by a mucosal route, we hypothesize that an intranasal vaccine should protect as well as, or better than, subcutaneous vaccination.

Experimental Design and Methods

Overall Experimental Design and Methods:

Recombinant diatom vaccines expressing IbpA DR2 or DR2 H/A are compared with parent diatoms as negative controls in protecting against *H. somni* induced bovine respiratory disease. The overall design is to produce recombinant diatom expressing IbpA DR2 and DR2 H/An antigens of *H. somni* at 20 μg of antigen/ml. We will compare intranasal vaccine with subcutaneous vaccine. Since our previous subcutaneous purified IbpA DR2 protein vaccine was protective, the subcutaneous diatom expressed DR2 vaccination is the positive control. The parent diatom vaccination is the negative control for *H. somni* induced pneumonia in unprotected calves. In case the IbpA DR2 induced epithelial cell retraction is detrimental, we will compare the systemic and intranasal IbpA DR2 vaccines with the toxoid (IbpA DR2 H/A) which does not cause bovine respiratory epithelial cells to retract in vitro (Zekarias, et al., *Infect Immun* (2010) 78:1850-1858).

Experimental Vaccination:

Recombinant diatom expressed protein vaccines will contain 200 μg of DR2 or DR2 H/A protein as determined by ELISA with quantitation based on a standard curve with purified rIbpA DR2. These experimental vaccines are compared with a parent diatom vaccinated control group. A total of 32 five-six week old male Holstein calves are purchased in year 2 and year 3 from a local dairy as in previous studies (Berghaus, et al., *Vaccine* (2006) 24:6018-6027; Corbeil, et al., *Vet Immunol Immunopathol* (2006) 113:191-199; Gershwin, et al., *Vet Immunol Immunopathol* (2005) 107:119-130). After adapting to UC Davis animal facilities for a few days and initial sample collection (serum samples, bronchio-alveolar lavage fluid (BALF) and naso-pharyngeal swabs), six animals per group are vaccinated twice (three weeks apart). Sample collection will occur at day −35, −14 and −2 and periodically after infection at Day 0 with *H. somni*. The vaccination/challenge experiments are in two replicates, with 3 animals per group at the end of year 2 and 3 animals per group at the beginning of year 3. This makes handling more feasible and allows testing of reproducibility.

*Vaccine* groups:
a) Parent diatom control group (4 animals intranasally and 4 animals subcutaneously)
b) Recombinant diatoms expressing IbpA DR2—subcutaneous vaccine (6 animals)
c) Recombinant diatoms expressing IbpA DR2 H/A—subcutaneous vaccine (6 animals)
d) Recombinant diatoms expressing IbpA DR2—intranasal vaccine (6 animals)
e) Recombinant diatoms expressing IbpA DR2 H/A—intranasal vaccine (6 animals)

Calves are vaccinated at day −35 and day −14, then infected intrabronchially with virulent live *H. somni* strain 2336 ($10^8$/calf) at day 0 as in previous studies (Berghaus, et al., *Vaccine* (2006) 24:6018-6027; Corbeil, et al., *Vet Immunol Immunopathol* (2006) 113:191-199; Gershwin, et al., *Vet Immunol Immunopathol* (2005) 107:119-130). Sample collection and daily clinical scoring is done as described above, with termination at day +4. Clinical signs are monitored at each pre-infection sampling time and twice daily after infection.

Immune Response Studies.

Isotypic antibody responses (IgG1, IgG2, IgE and IgA) are quantitated in BALF and sera (except for serum IgA because cattle have almost no serum IgA) by ELISA against *H. somni* IbpA DR2 purified recombinant protein. Antibodies to IbpA DR2 reacted equally with IbpA DR2 and IbpA DR2H/A in Western blots, with identical patterns of bands (IbpA always appears as several bands in Westerns—10, 100, 102, 103, 105, 106). Therefore, antibodies to IbpA DR2 H/A also react with IbpA DR2 in Westerns. Western blotting studies of selected preimmune sera and BALF, as well as sera and BALF collected during immunization, at challenge and at necropsy are done to compare reactivity with native IbpA (in CCS) and with recombinant IbpA DR2 and DR2 H/A.

Antibody Neutralization Studies.

Figure 4:
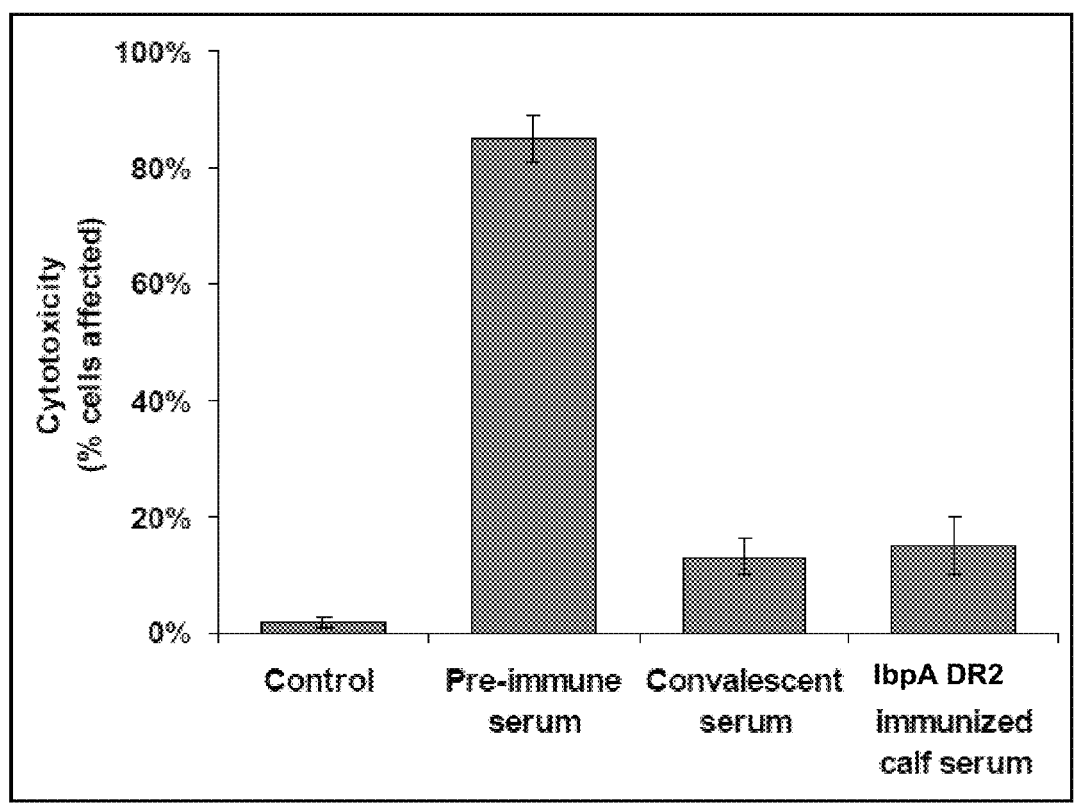
FIG. 4 illustrates antibody neutralization of IbpA DR2 cytotoxicity for BAT2 cells. Note that untreated control cells had very little retraction but cells treated with IbpA DR2 and pre-immune calf serum were nearly all (>80%) retracted. Both convalescent phase serum and serum from IbpA DR2 immunized calves neutralized cytotoxicity (retraction) p<0.05.

Sera from calves immunized with rIbpA DR2 protein neutralized cytotoxicity for BAT2 cells in vitro (FIG. 4). In order to compare the neutralizing ability of antibodies to IbpA DR2 and IbpA DR2 H/A, pre-challenge sera and pre-immune sera from calves immunized systemically with diatoms expressing these antigens are tested in BAT2 cell cytotoxicity assays as in our previous studies. Sera from the previously immunized and protected calves (see FIG. 4 above) are used as positive control serum and pre-immunization sera are used as negative control serum.

Methods:

Power Analysis to Determine Acceptable Numbers of Animals in Each Group:

Power estimates to verify adequate sample size were performed using an online power calculator (StatisticalPower Calculator, DSS research, Fort Worth, Tex., available on the internet at: dssresearch.com/toolkit/spcalc/power_a2.asp) for two-tailed comparisons between two means. In our previous studies of BRSV and *H. somni* synergism, we determined adequate samples sizes. The current experiments with immunization and *H. somni* challenge are similar. Calculations were made using two variables comparing each *H. somni* vaccinated groups with the control group, with 6 calves per group and an alpha value of 0.05:1) Average % of gross lung consolidation. This % in the vaccinated and control groups were estimated at 7±5% and 25±14%, respectively, based on expected values. Power to detect a difference of 18% between the two groups in lung consolidation was 84.3%. 2) Average daily clinical score. The average daily clinical score, based on previous infection studies, was estimated at 50±50 for the vaccinated and 180±100 in the control groups. Statistical power to detect this difference is 81.3%. Six calves per group will used herein because we expect similar types of results as in the synergy study. Two set of controls (4 calves each) with parent intact or sonicated diatoms are included because we expect the same results with both.

Experimental Infection with *H. somni*:

Infection with *H. somni* is performed according to the protocol we have used in our previous studies on synergy of BRSV and *H. somni*. Briefly, a culture of *H. somni* (previously calf passaged strain 2336, vial 738) is grown for 18 hours and sub-cultured onto Columbia blood agar (10% bovine blood) plates. The bacteria are then scraped from the plates and suspended in RPMI 1640 medium to a suspension that gives a turbidity of 75% T at 610 nm. This turbidity represents approximately $10^8$ bacteria/ml. Bacterial numbers are confirmed by plate counts of the inoculum. A final dilution in RPMI 1640 is then made so as to have $10^8$ bacteria in a 10 ml inoculum ($10^7$ bacteria/ml.). Each calf receives the 10 ml inoculum instilled into the trachea at the bronchial bifurcation through a tube inserted through the ventral meatus of the nasal cavity. Calves in groups that do not receive *H. somni* will have 10 ml of sterile RPMI instilled using an identical technique. Bacteria are administered in the morning and the calves are checked approximately 8 hours later for clinical signs.

Monitoring for *H. somni* Shedding: Deep nasal swabs are obtained from the nasal cavity to evaluate *H. somni* shedding. The swab is placed into a tube containing RPMI 1640 for transport to the laboratory within 2 hours. The swab is then streaked onto a Columbia blood agar plate and incubated in a candle jar for 48 hours. Plates are examined for the presence of *H. somni* and number of colonies estimated semi-quantitatively.

Bronchoalveolar Lavage:

Lung lavage is performed using a method that we have previously used successfully (Berghaus, et al., *Vaccine* (2006) 24:6018-6027; Corbeil, et al., *Vet Immunol Immunopathol* (2006) 113:191-199; Gershwin, et al., *Vet Immunol Immunopathol* (2005) 107:119-130). Each sample is cultured for *H. somni*. Cytospin preparations are prepared for IFA examination for the presence of BRSV and for differential cell morphology. The fluid is then centrifuged to remove the cell pellet and the supernatant is stored at −20° C. until assayed for antibody content. The cell pellet is retained at −80° C. for RNA.

Assessment of Clinical Signs:

A clinical sign score is determined each day for each animal after physical examination by a veterinarian (LG) blinded to the treatment group status and scoring of signs using our standard methods (Berghaus, et al., *Vaccine* (2006) 24:6018-6027; Corbeil, et al., *Vet Immunol Immunopathol* (2006) 113:191-199; Gershwin, et al., *Vet Immunol Immunopathol* (2005) 107:119-130). Assignment of points is based on parameters including temperature elevation, spontaneous and induced cough, nasal exudate, lung auscultation, presence of dyspnea, wheezing, anorexia, and depression.

Necropsy Procedure and Pathological Evaluation:

Calves are euthanized with barbiturates, and a necropsy performed on day 28 of the experiment. The entire respiratory tract is removed, and lesions are diagramed on a lung drawing. Areas of atelectasis and consolidation are estimated as a percentage for each lobe and for the entire lung. Following the standard procedure used in our experiments the left lung is removed intact from the left mainstem bronchus and infused via an intra-bronchial catheter with 10% neutral buffered formalin until fully expanded. Samples from the right lung are obtained for culture of aerobic/capnophilic bacteria and for fluorescent antibody examination for infectious bovine rhinotracheitis (IBR/BHV1), bovine virus diarrhea virus (BVD), and BRSV, as well as for BRSV, and *H. somni* immunoperoxidase testing. Routine sampling for histological examination is performed on 14 standard sites in the right and left lung. Additional histological samples are taken from lesions that are present in areas that were not included in the routine samples. All histological samples are labeled as to site and fixed in 10% neutral buffered formalin. Histological examination is performed on sections of the trachea, right main stem bronchus and from lung samples from the right and left apical, middle and caudal lobes.

Statistical Analysis:

To be performed on data obtained from in vivo assays using nonparametric analysis, ANOVA with post-hoc testing. For in vitro assays triplicate assays are used to compare using unpaired student's T test and/or Fisher's exact test. Significance is set at $p<0.05$.

Example 2

Diatom-Based Bovine Respiratory Syncytial Virus
(BRSV)/*Histophilus somni* Vaccines for Bovine
Respiratory Disease Caused by Viral/Bacterial
Synergy BRSV is an immunomodulator. Inactivated, adjuvanted BRSV vaccines induce a Th2 response (Gershwin et al., *Vaccine* (1998) 16:1225-36; Gershwin, et al., *Am J Vet Res*. (2000) 61:291-8; Gershwin, et al., *Vet Immunol Immunopathol*. (2005) 107:119-130; Kalina, et al., *Vaccine* (2004) 22:1465-72; Woolums, et al., *Vaccine*. (1999) 17(11-12): 1293-7). *H. somni* also tends to stimulate excessive IgE antibodies (Gershwin, et al., *Am J Vet Res*. (2000) 61:291-8; Gershwin, et al., *Vet Immunol Immunopathol*. (2005) 107: 119-130; Ruby, et al., *Vet Microbiol* (2000) 76:373-383). Th1 responses are more protective against both BRSV and *H. somni*. CD8 T cells are important in protecting against BRSV (Valarcher, et al., *Vet Res* (2007) 38:153-180) and IgG2 antibodies (characteristic of a Th1 response) are important in protection against *H. somni* infection (Corbeil, et al., *Can J Vet Res* (1997) 61:207-213). Therefore it is important to choose antigens and adjuvants which preferentially stimulate Th1 responses. It is also desirable to choose antigens which do not vary among strains and which do not undergo antigenic variation under immune pressure. From BRSV, protective antigens include the G, F and N proteins. The G protein shows some antigenic variation among field isolates and also some studies suggest that it suppresses antiviral T cell responses (Valarcher, et al., *Vet Res* (2007) 38:153-180). In addition, the G protein has been shown to modulate the immune response towards Th2 (Oshansky, et al., *J Infect Dis*. (2010) 201:1201-7). The F protein is highly conserved among isolates but it suppresses lymphocyte proliferation and decreases effector function of CD8 T cells (Valarcher, et al., *Vet Res* (2007) 38:153-180). The nucleoprotein (N) is highly conserved and not known to be immunosuppressive or immunomodulatory toward an IgE response (Valarcher, et al., *Vet Res* (2007) 38:153-180). In immunization experiments, vaccinia virus vectors expressing F, G or N proteins were all protective but N protein induced the highest IgG2 BRSV antibody responses and BRSV specific lymphocyte proliferative responses (Taylor, et al., *J Gen Virol* (1997) 78:3195-3206). Other studies with N and F protein or DNA vaccines showed protection with the N protein gene but not with the F protein gene. This same DNA vaccine was shown to partially protect infant Rhesus macaques from infection with human RSV (Vaughan, et al., *Vaccine*. (2005) 22:2928-42). Since the N protein is conserved (non-variant), not immunosuppressive and is protective, it finds use for expression as an antigen in a diatom host cell. IbpA DR2/Fic is also conserved and non-variant as determined by PCR and by sequence analysis. It stimulates good IgG2 responses and lower IgE responses than other IbpA subunits (Corbeil, et al., *Vet Immunol Immunopathol* (2006) 113:191-199). We have also shown the IbpA DR2 subunit protects mice (Geertsema, et al., *Vaccine* (2008) 26:4506-4512) and calves against *H. somni* infection. Therefore, this *H. somni* antigen and the BRSV N protein can be used to induce protective Th1 rather than IgE responses.

Overall Experimental Design and Methods:

The overall design is to produce recombinant proteins of BRSV and *H. somni* in diatom host cells for a combined subunit vaccine for comparison with alum adjuvanted killed BRSV and *H. somni* vaccines typical of those inducing high IgE responses. The goal is to induce higher IgG2 and T cell responses and less IgE along with better protection. BRSV N protein alone or with IbpA DR2/Fic can be expressed in diatom host cells employing methodologies described above and herein. For example, BRSV N protein alone or with IbpA DR2/Fic (e.g., as a fusion protein) can be expressed under the control of a promoter from a FCP (fucoxanthin chlorophyll binding protein) or a rpL41(ribosomal protein L41) gene. For cell surface localization, the BRSV N protein alone or with IbpA DR2/Fic, can be fused as a one or more fusion proteins to a frustulin polypeptide, e.g., full-length ε-frustulin. The expression cassette can be cloned into a Gateway vector, as described above, and expressed in diatom host cells. The recombinant proteins expressed in the diatom host cells can be administered to an animal host for induction of an immune response without purification. In varying embodiments, the BRSV N protein alone or with IbpA DR2/Fic is co-expressed or co-administered with an adjuvant.

Experimental Vaccination:

Diatom expressed BRSV/*H. somni* protein vaccines containing at least about 200 µg of each protein are compared with killed alum adjuvanted vaccines used in earlier studies (Berghaus, et al., *Vaccine* (2006) 24:6018-6027) and with an unvaccinated control group. Eighteen 5-6 week old male Holstein calves are purchased from a local dairy as in previous studies (Gershwin, et al., *Vet Immunol Immunopathol*. (2005) 107:119-130; Corbeil, et al., *Vet Immunol Immunopathol* (2006) 113:191-199; Berghaus, et al., *Vaccine* (2006) 24:6018-6027). After initial sample collection (serum samples, bronchioalveolar lavage fluid (BALF) and nasopharyngeal swabs) six animals per group are vaccinated twice (three weeks apart). Sample collection at day −35, −14 and −2 and periodically after infection at Day 0 with BRSV and Day 6 with *H. somni*. Vaccine groups—dual killed vaccine, diatom expressed recombinant protein vaccine (BRSV N protein+*H. somni* IbpA DR2/Fic) or mock vaccine. Calves are infected with BRSV ($5 \times 10^4$ $TCID_{50}$) by aerosol, two weeks after the second vaccination, at day 0 and/or with virulent live *H. somni* strain 2336 ($10^8$/calf) at day 6 as in previous studies (Berghaus, et al., *Vaccine* (2006) 24:6018-6027; Corbeil, et al., *Vet Immunol Immunopathol* (2006) 113:191-199; Gershwin, et al., *Vet Immunol Immunopathol* (2005) 107:119-130). Sample collection and daily clinical scoring is done as in the above studies, with termination at day 28. The experiment is done in two replicates with 3 animals/group in the each replicate (total=6 animals per group).

Immune Response Studies.

Isotypic antibody responses (IgG1, IgG2, IgE and IgA) are quantitated in BALF and sera (without IgA for sera) against BRSV and *H. somni* whole pathogen antigens as well as BRSV N protein or *H. somni* IbpA DR2 proteins. Cytokine proteins in the BALF at selected time points can be assayed by ELISA (e.g., TNFα, IL8, IL6, IL4 and IFN-γ). The Th1 (IFN-γ) and Th2 (IL4) cytokine levels are compared with isotypic antibody results in order to understand immunomodulation by the vaccines.

Intracellular cytokines in CD4 and CD8 T Cells are quantitated by flow cytometry. On days −35, −14, −2, 6, 10, 14, 21, and 28 peripheral blood lymphocytes are obtained from heparinized blood. The ficoll-hypaque separated lymphocytes are enumerated and aliquoted for intracellular staining with commercially available antibodies for: IL-4, IL-2, IFN-γ. These cells are incubated with media alone, N protein, IbpA DR2/Fic, or both. The Golgi-stop method of retaining intracellular cytokines are used prior to staining antibodies to cytokines Surface markers for CD4 and CD8 are evaluated after staining for intracellular cytokines is complete. Additional samples are stained for viability. Multicolor flow cytometry are used.

Power Analysis to Determine Acceptable Numbers of Animals in Each Group:

Power estimates to verify adequate sample size are calculated as under Example 1.

Experimental Infection with BRSV—

A BRSV infection protocol is used as previously established (Gershwin, et al., Vaccine (1998) 16:1225-36; Gershwin, et al., Vet Immunol Immunopathol (2005) 107:119-130). Briefly, a virulent field isolate of BRSV (CA-1) is grown on bovine turbinate cells. The cells are observed daily for cytopathic effect (CPE); when CPE is observed, the virus is harvested by removing the cell supernatant, flash freezing the cells to release intracellular virus, and washing the flask with media. The virus infected media is centrifuged to remove the cell debris and is retained on ice until administration (within 30 minutes) to the calf. A representative sample is withheld and used to for $TCID_{50}$ assay to determine the titer of the virus preparation. The titer of the virus used is usually in the range of $4-5 \times 10^5$ $TCID_{50}$/ml. Calves receive 5 ml of the virus suspension by aerosol via face mask using a DeVilbis nebulizer system.

Experimental Infection with H. somni—

Infection with H. somni is performed according to the protocol described under Example 1.

Monitoring for BRSV and H. somni Shedding.

Deep nasal swabs are obtained from the left (BRSV) and right (H. somni) nasal cavity to evaluate pathogen shedding on days 0-14, and 21 and 28. The BRSV swab is put into 1 ml of EMEM and vigorously stirred to remove cells. The cells are then centrifuged onto slides, fixed and examined for the presence of BRSV using a FITC conjugated anti-RSV. The swabs for H. somni isolation are monitored as described under Example 1.

Bronchoalveolar Lavage.

Lung lavage is performed using a method that we have previously used successfully (McVey, An Hlth Res Rev (2009) 10:165-167). Each sample is cultured for H. somni. Cytospin preparations are prepared for IFA examination for the presence of BRSV and for differential cell morphology. The fluid is then centrifuged to remove the cell pellet and the supernatant is stored at −20° C. until assayed for antibody content. The cell pellet is retained at −80° C. for RNA.

Assessment of Clinical Signs.

A clinical sign score is determined each day for each animal after physical examination by a veterinarian, as described under Example 1.

Necropsy Procedure and Pathological Evaluation—

Calves are euthanized with barbiturates, and a necropsy performed on day 28 of the experiment, as described under Example 1.

Statistical Analysis is performed on data obtained from in vivo assays using nonparametric analysis, ANOVA with post-hoc testing. For in vitro assays triplicate assays are used to compare using unpaired student's T test and/or Fisher's exact test. Significance is set at $p<0.05$.

Example 3

Diatom-Based Enteric Vaccines

Diatom based vaccines constitute a new, transformational idea because these unicellular algae, with biosilica cell walls, are easily grown in water at ambient temperatures, providing low cost in resource-limited settings. The vaccines would be stable without refrigeration and could be lyophilized for dispensing oral vaccines in food or water. Vibrio cholera CTB was expressed in Thalassioira pseudonana for several reasons. CTB acts as an adjuvant for mucosal immunity and sometimes has been used as an antigen, as well, for a successful cholera vaccine in animal models. Hypotheses can be tested in this model and can be translated to use of diatom expressed antigens for oral vaccines against other enteric diseases. Additional V. cholera antigens may be expressed. Subsequent studies focus on other important enteric pathogens, such as Campylobacter jejuni, Salmonella spp, Escherichia coli and its toxins, Giardia and Entamoeba histolytica.

a) Expression of cholera toxin B (CTB) in diatoms. CTB is cloned in a Gateway™ vector developed by us, driven by a highly expressed promoter (rpL41) and fused to frustulin 1 from T. pseudonana. Frustulins are abundant cell surface proteins in diatoms. The recombinant CTB diatoms are microparticles. The diatoms are sonicated to provide nanoparticles having the same organic composition as whole diatom cell walls except for size.

b) Surface expression is confirmed by enzyme-linked immunosorbant assay (ELISA) or immunofluorescence assay (IFA) using rabbit antibody to CTB. Specificity for CTB is determined by Western blotting.

c) Activity of parent diatoms and CTB expressing diatoms is tested in vitro with mouse macrophages by measuring TNFα production by ELISA, as an indication of activation and adjuvant activity.

d) Uptake of parent and CTB diatoms by human intestinal epithelial cells is tested in vitro using polarized cell lines such as Caco-2, HT29 or T84 cells. Diatoms are grown in the presence of rhodamine 123, which fluorescently labels the silica cell walls for examination of uptake by confocal microscopy. Induction of proinflammatory cytokines (e.g., TNFα, IL-6, IL-8) by epithelial cells is done by ELISA to measure activation.

e) The localization of parent and CTB diatoms in the intestine is determined by feeding fluorescent diatoms to mice. In vivo imaging techniques used to localize diatoms. Safety is analyzed be monitoring clinical signs with or without diatom feeding. Inflammation and cellular location of diatoms is determined by histopathology.

f) Immune responses to CTB is monitored in serum and extracted feces by isotype specific ELISA.

CTB/antigen expressing diatoms are further investigated in stimulation of protective serum and intestinal antibody responses in mouse and/or rabbit models for cholera. Microparticles are compared with nanoparticles produced by sonicating CTB expressing diatoms. CTB-expressing diatoms find use in protecting against oral cholera toxin and against V. cholera infection.

Based on the cholera in vitro assays and in vivo models, additional antigens can be expressed, for example antigens that stimulate an immune response against enteric pathogens, e.g., Campylobacter jejuni.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A diatom comprising a nucleic acid encoding an antigen heterologous to the diatom, wherein the antigen is expressed as a fusion protein with a surface-expressed polypeptide endogenous to the diatom selected from a frustulin and p150 cell surface protein, wherein the fusion protein is attached to the surface of the diatom, wherein the diatom is an intact cell.

2. The diatom of claim 1, wherein the antigen is expressed as a fusion protein with a frustulin protein having at least 90% sequence identity to SEQ ID NO:6 or SEQ ID NO:7.

3. The diatom of claim 1, wherein the antigen is expressed under the control of a promoter endogenous to the diatom selected from the group consisting of fucoxanthin chlorophyll binding protein (FCP) promoter and ribosomal protein L41 (rpL41) promoter.

4. The diatom of claim 3, wherein the FCP promoter comprises a nucleic acid sequence having at least 90% sequence identity to SEQ ID NO:1.

5. The diatom of claim 1, wherein the antigen is an antibody or fragment thereof.

6. The diatom of claim 5, wherein the antibody is a transmission blocking antibody, wherein the transmission blocking antibody inhibits the growth and/or replication of an infectious agent.

7. The diatom of claim 5, wherein the antibody is a single domain antibody or a nanobody.

8. The diatom of claim 1, wherein the diatom is a *Thalassiosira pseudonana*.

9. An expression cassette comprising:
i) a promoter selected from the group consisting of fucoxanthin chlorophyll binding protein (FCP) promoter and ribosomal protein L41 (rpL41) promoter; the promoter operably linked to;
ii) a nucleic acid encoding a diatom cell surface polypeptide selected from a frustulin and p150 cell surface protein; the nucleic acid encoding the diatom cell surface polypeptide operably linked to;
iii) a nucleic acid encoding an antigen heterologous to a diatom.

10. The expression cassette of claim 9, wherein the FCP promoter comprises a nucleic acid sequence having at least 90% sequence identity to SEQ ID NO:1.

11. The expression cassette of claim 9, wherein the antigen is expressed as a fusion protein with a frustulin protein having at least 90% sequence identity to SEQ ID NO:6 or SEQ ID NO:7.

12. The expression cassette of claim 9, wherein the antigen is an antibody or fragment thereof.

13. The expression cassette of claim 2, wherein the antibody is a transmission blocking antibody, wherein the transmission blocking antibody inhibits the growth and/or replication of an infectious agent.

14. The expression cassette of claim 12, wherein the antibody is a single domain antibody or a nanobody.

15. A vector or plasmid comprising the expression cassette of claim 9.

16. The vector or plasmid of claim 15, wherein the vector is a plasmid comprising a nucleic acid sequence having at least 90% sequence identity to SEQ ID NO:8.

17. A diatom comprising the expression cassette of claim 9.

18. The diatom of claim 17, wherein the diatom is a *Thalassiosira pseudonana*.

19. A composition comprising a diatom or a population of diatoms of claim 1 and a pharmaceutically acceptable carrier.

20. A method of stimulating an immune response in an animal, comprising administering to the animal a composition of claim 19 in an amount effective to stimulate the immune response in the animal.

21. The method of claim 20, wherein the diatom is administered in the water or food or by aerosol.

22. The method of claim 20, wherein the animal is a mammal.

23. A sonicated diatom particle attached to a fusion protein, the fusion protein comprises an antigen heterologous to the diatom fused to a surface-expressed polypeptide endogenous to the diatom selected from a frustulin and p150 cell surface protein.

24. The sonicated diatom particle of claim 23, wherein the frustulin protein has at least 90% sequence identity to SEQ ID NO:6 or SEQ ID NO:7.

25. The sonicated diatom particle of claim 23, wherein the antigen is an antibody or fragment thereof.

26. The sonicated diatom particle of claim 25, wherein the antibody is a transmission blocking antibody, wherein the transmission blocking antibody inhibits the growth and/or replication of an infectious agent.

27. The sonicated diatom particle of claim 25, wherein the antibody is a single domain antibody or a nanobody.

28. The sonicated diatom particle of claim 23, wherein the diatom particle is from a *Thalassiosira pseudonana*.

29. The sonicated diatom particle of claim 23, wherein the diatom particle is a microparticle or a nanoparticle.

30. A composition comprising a sonicated diatom or a population of sonicated diatom particles of claim 23 and a pharmaceutically acceptable carrier.

31. A method of stimulating an immune response in an animal, comprising administering to the animal a composition of claim 30 in an amount effective to stimulate the immune response in the animal.

32. The method of claim 31, wherein the sonicated diatom particle is administered in the water or food or by aerosol.

33. The method of claim 31, wherein the animal is a mammal.

* * * * *